US009574185B2

(12) United States Patent
Yim et al.

(10) Patent No.: US 9,574,185 B2
(45) Date of Patent: Feb. 21, 2017

(54) COLD-ADAPTED PROTEASE DERIVED FROM *PSEUDOALTEROMONAS ARCTICA* PAMC 21717 AND USES THEREOF

(71) Applicant: KOREA INSTITUTE OF OCEAN SCIENCE & TECHNOLOGY, Gyeonggi-do (KR)

(72) Inventors: Joung Han Yim, Gyeonggi-do (KR); Bon-Hun Koo, Seoul (KR); Chul Soo Shin, Gyeonggi-do (KR); Dockyu Kim, Incheon (KR); Il-Chan Kim, Gyeonggi-do (KR); Se Jong Han, Gyeonggi-do (KR); Jun Hyuck Lee, Incheon (KR); Ha Ju Park, Gyeonggi-do (KR)

(73) Assignee: KOREA INSTITUTE OF OCEAN SCIENCE & TECHNOLOGY, Gyeonggi-Do (KR)

(*) Notice: Subject to any disclaimer, the term of this patent is extended or adjusted under 35 U.S.C. 154(b) by 0 days.

(21) Appl. No.: 14/583,557

(22) Filed: Dec. 26, 2014

(65) Prior Publication Data
US 2016/0083708 A1 Mar. 24, 2016

(30) Foreign Application Priority Data

Sep. 24, 2014 (KR) ........................ 10-2014-0127957

(51) Int. Cl.
*C12N 9/52* (2006.01)
*A01N 63/02* (2006.01)
*C12N 9/14* (2006.01)
*C12N 9/16* (2006.01)
*A01N 37/46* (2006.01)
*A61K 38/48* (2006.01)

(52) U.S. Cl.
CPC .............. *C12N 9/52* (2013.01); *A01N 37/46* (2013.01); *A01N 63/02* (2013.01); *A23L 5/00* (2016.08); *A61K 38/482* (2013.01); *C12N 9/14* (2013.01); *C12N 9/16* (2013.01); *C12Y 304/21* (2013.01); *C07K 2299/00* (2013.01)

(58) Field of Classification Search
None
See application file for complete search history.

(56) References Cited

FOREIGN PATENT DOCUMENTS

WO 2005123911 A2 12/2005
WO 2009021000 A2 2/2009

OTHER PUBLICATIONS

Kundrot, C.E. Which Strategy for a Protein Crystallization Project? Cellular Molecular Life Science. 2004. vol., 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Moon et al., "A synergistic approach to protein crystallization: Combination of a fixed-arm carrier with surface entropy reduction", Protein Science, 2010, 19:901-913.*
McPherson, A. Current Approaches to Macromolecular Crystallization. European Journal of Biochemistry. 1990. vol. 189, pp. 1-23.*
Gupta, R., et al., "Bacterial alkaline proteases: molecular approaches and industrial applications", "Appl Microbiol Biotechnol", Apr. 20, 2002, pp. 15-32, vol. 59.
Haddar, A., et al., "Two detergent stable alkaline serine-proteases from Bacillus mojavensis A21: Purification, characterization and potential application as a laundry detergent additive", "Bioresource Technology", Mar. 9, 2009, pp. 3366-3373, vol. 100.
Huston, A., et al., "Purification, Characterization, and Sequencing of an Extracellular Cold-Active Aminopeptidase Produced by Marine Psychrophile Colwellia psychrerythraea Strain 34H", "Applied and Environmental Microbiology", Jun. 2004, pp. 3321-3328, vol. 70, No. 6.
Kulakova, L., et al., "Cold-Active Serine Alkaline Protease from the Psychrotrophic Bacterium Shewanella Strain Ac10: Gene Cloning and Enzyme Purification and Characterization", "Applied and Environmental Microbiology", Feb. 1999, pp. 611-617, vol. 65, No. 2.
Neumann, E., et al., "Gene transfer into mouse lyoma cells by electroporation in high electric fields", "The EMBO Journal", 1982, pp. 841-845, vol. 1, No. 7.
Co-pending Unpublished U.S. Appl. No. 14/583,564, filed Dec. 26, 2014.
Wang, Q., et al., "Purification and characterization of an extracellular cold-active serine protease from the psychrophilic bacterium *Colwellia* sp. NJ341", "Biotechnology Letters", Aug. 2005, pp. 1195-1198, vol. 27.
Spellman, D., et al., "Proteinase and Exopeptidase Hydrolysis of Whey Protein: Comparison of the TNBS, OPA, and pH Stat Methods for Quantification of Degree of Hydrolysis", "International Dairy Journal", Feb. 22, 2003, pp. 447-453, vol. 13.
Aghajari, N., et al., "Crystal Structures of a Psychrophilic Metalloprotease Reveal New Insights into Catalysis by Cold-Adapted (Continued)

*Primary Examiner* — Suzanne M Noakes
(74) *Attorney, Agent, or Firm* — Hultquist, PLLC; Steven J. Hultquist

(57) ABSTRACT

A cold-adapted protease derived from *Pseudoalteromonas arctica* PAMC 21717 or a recombinant cold-adapted protease obtained by expressing a gene encoding the cold-adapted protease in *E. coli* is described, and more particularly, a crystal of a protease exhibiting activity at low temperatures, a method for crystallizing the protease, a method for preparing the protease, a recombinant microorganism that expresses the protease, a method for preparing the recombinant microorganism, a method for preparing the recombinant protease and the use of the cold-adapted protease. The cold-adapted protease exhibits high activity at low temperatures, and securely maintains its enzymatic activity even in the presence of high pH, various metal ions and surfactants. Thus, it is useful in various industrial applications.

11 Claims, 11 Drawing Sheets

(56) References Cited

OTHER PUBLICATIONS

Proteases", "Proteins: Structure, Function and Genetics", Mar. 1, 2003, pp. 636-647, vol. 50, No. 4.

Almog, O., et al., "The crystal structures of the psychrophilic subtilisin S41 and the mesophilic subtilisin Sph reveal the same calcium-loaded state", "Proteins: Structure, Function and Bioinformatics", Feb. 1, 2009, pp. 489-496, vol. 74, No. 2.

Arnorsdottir, J., et al., "Characterization of a cloned subtilisin-like serine proteinase from a psychrotrophic *Vibrio* species", "European Journal of Biochemistry", Nov. 1, 2002, pp. 5536-5546, vol. 269, No. 22.

Arnorsdottir, J., et al., "Crystal structure of a subtilisin-like serine proteinase from a psychrotrophic *Vibrio* species reveals structural aspects of cold adaptation", "FEBS Journal", Feb. 1, 2005, pp. 832-845, vol. 272, No. 3.

Bian, F., et al., "Genome sequences of six Pseudoalteromonas strains isolated from Arctic sea ice", "Journal of Bacteriology", Feb. 15, 2012, pp. 908-909, vol. 194, No. 4.

Chen, X., et al, "Two different proteases produced by a deep-sea psychtrophic bacterial strain, *Pseudoaltermonas* sp. SM9913", "Marine Biology", Jul. 9, 2003, pp. 989-993, vol. 143.

Cristobal, H., et al., "Diversity of protease-producing marine bacteria from sub-antarctic environments", "Journal of Basic Microbiology", Jun. 9, 2011, pp. 590-600, vol. 51, No. 6.

Dheilly, A., et al., "Antibiofilm activity of the marine bacterium *Pseudoalteromonas* sp. strain 3J6", "Applied and Environmental Microbiology", Jun. 1, 2010, pp. 3452-3461, vol. 76, No. 11.

Dong, D., et al., "Crystallization and preliminary X-ray crystallographic studies of a psychophilic subtilisin-like protease Apa1 from Antarctic *Pseudoalteromonas* sp. strain AS-11", "Acta Crystallogr Sect F Struct Biol Cryst Commun", Mar. 1, 2005, pp. 308-311, vol. 61, Pt 3.

Feller, G., et al., "Psychrophilic enzymes: hot topics in cold adaptation", "Nature reviews Microbiology", Dec. 1, 2003, pp. 200-208, vol. 1, No. 3.

Joshi, S., et al., "Biotechnology of cold-active proteases", "Biology (Basel)", May 3, 2013, pp. 755-783, vol. 2, No. 2.

Kennan, R., et al., "The subtilisin-like protease AprV2 is required for virulence and uses a novel disulphide-tethered exosite to bind substrates", "PLoS Pathogens", Nov. 24, 2010, pp. 1-12, vol. 6, No. 11.

Kuddus, M., et al., "Recent developments in production and biotechnological applications of cold-active microbial proteases", "Critical Reviews in Microbiology", Nov. 1, 2012, pp. 330-338, vol. 38, No. 4.

Park, H., et al., "Identification of proteolytic bacteria from the Arctic Chukchi Sea expedition cruise and characterization of cold-active proteases", "Journal of Microbiology", Aug. 27, 2014, pp. 825-833, vol. 52, No. 10.

Russell, N., "Toward a molecular understanding of cold activity of enzymes from psychrophiles", "Extremophiles", Apr. 1, 2000, pp. 83-90, vol. 4, No. 2.

\* cited by examiner

SEQUENCE LISTING

```
<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: pDOC122-f

<400> SEQUENCE: 1
atgacaacaa gtaaaacttt taaaagatgc gc                                       32

<210> SEQ ID NO 2
<211> LENGTH: 23
<212> TYPE: DNA
<213> ORGANISM: Artificial Sequence
<220> FEATURE:
<223> OTHER INFORMATION: pDOC122-r

<400> SEQUENCE: 2
cacttagcgg acaataccaa ccg                                                 23

<210> SEQ ID NO 3
<211> LENGTH: 26
<212> TYPE: DNA
<213> ORGANISM: Artificial Sequence
<220> FEATURE:
<223> OTHER INFORMATION: pDOC125-f

<400> SEQUENCE: 3
atgcaatcag tttcaagttc aatggc                                              26

<210> SEQ ID NO 4
<211> LENGTH: 23
<212> TYPE: DNA
<213> ORGANISM: Artificial Sequence
<220> FEATURE:
<223> OTHER INFORMATION: pDOC125-r

<400> SEQUENCE: 4
cacttagcgg acaataccaa ccg                                                 23

<210> SEQ ID NO 5
<211> LENGTH: 32
<212> TYPE: DNA
<213> ORGANISM: Artificial Sequence
<220> FEATURE:
<223> OTHER INFORMATION: pDOC128-f

<400> SEQUENCE: 5
atgacaacaa gtaaaacttt taaaagatgc gc                                       32

<210> SEQ ID NO 6
<211> LENGTH: 21
<212> TYPE: DNA
```

```
<213> ORGANISM: Artificial Sequence
<220> FEATURE:
<223> OTHER INFORMATION: pDOC128-r

<400> SEQUENCE: 6
gcagctgttg cagcagcaag t                                                  21

<210> SEQ ID NO 7
<211> LENGTH: 26
<212> TYPE: DNA
<213> ORGANISM: Artificial Sequence
<220> FEATURE:
<223> OTHER INFORMATION: pDOC131-f

<400> SEQUENCE: 7
atgcaatcag tttcaagttc aatggc                                             26

<210> SEQ ID NO 8
<211> LENGTH: 21
<212> TYPE: DNA
<213> ORGANISM: Artificial Sequence
<220> FEATURE:
<223> OTHER INFORMATION: pDOC131-r

<400> SEQUENCE: 8
gcagctgttg cagcagcaag t                                                  21

<210> SEQ ID NO 9
<211> LENGTH: 8
<212> TYPE: PRT
<213> ORGANISM: Artificial Sequence
<220> FEATURE:
<223> OTHER INFORMATION: W-Pro21717 N-terminal sequence

<400> SEQUENCE: 9

Gly Ala Gln Asn Ser Ser Trp His
1               5

<210> SEQ ID NO 10
<211> LENGTH: 303
<212> TYPE: PRT
<213> ORGANISM: Artificial Sequence
<220> FEATURE:
<223> OTHER INFORMATION: cold-adapted protease

<400> SEQUENCE: 10

Ser Thr Pro Asn Asp Pro Arg Phe Asp Gln Trp His Tyr Glu Gln Ala
1               5                   10                  15

Gly Leu Asn Leu Pro Thr Ala Trp Asp Thr Ala Thr Gly Ser Gly Val
            20                  25                  30

Ala Val Leu Asp Thr Gly Tyr Arg Pro His Ala Asp Leu Asn Ala Asn
        35                  40                  45

Ile Leu Pro Gly Tyr Asp Met Ile Ser Asn Leu Ser Val Ala Asn Asp
    50                  55                  60

Gly Arg Asp Ser Asp Ala Arg Asp Pro Gly Asp Ala Val Ala Asn Glu
65                  70                  75                  80

Cys Gly Thr Asn Gly Ala Gln Asn Ser Trp His Gly Thr His Val Ala
                85                  90                  95

Gly Thr Val Ala Val Thr Asn Gly Glu Val Ala Gly Val Ala Tyr
            100                 105                 110

Asn Ala Lys Val Pro Val Arg Val Leu Gly Lys Cys Gly Leu Thr Ser
        115                 120                 125
```

-continued

```
Asp Ile Ala Asp Gly Ile Trp Ala Ser Gly Ser Val Ser Gly Ile Pro
    130             135             140
Ala Asn Ser Asn Pro Ala Asp Val Ile Asn Met Ser Leu Gly Ser Gly
145             150             155             160
Ser Cys Ser Thr Gln Asn Ala Ile Asn Thr Ala Arg Ser Asn Gly Thr
            165             170             175
Val Ile Ala Gly Asn Asp Asn Asp Asn Ser Ala Asn Tyr Asn Pro Gly
            180             185             190
Asn Cys Asn Gly Val Asn Val Gly Ser Val Gly Arg Asn Gly Arg Ala
            195             200             205
Tyr Ser Asn Tyr Gly Ser Asn Ile Asp Val Ala Pro Gly Ala Gln Ser
    210             215             220
Phe Ala Asn Asp Ser Glu Gly Val Leu Ser Thr Tyr Asn Ser Gly Ser
225             230             235             240
Thr Pro Ser Asp Ser Tyr Gly Tyr Ser Gln Gly Thr Ser Met Ala Pro
            245             250             255
His Val Ala Gly Val Ala Leu Ile Lys Gln Ala Lys Pro Asp Ala Thr
            260             265             270
Pro Asp Glu Ile Glu Ser Ile Leu Lys Ser Thr Arg Ser Phe Pro Ala
            275             280             285
Thr Cys Thr Ser Cys Gly Thr Gly Ile Val Asp Ala Val Ala Ser
    290             295             300
```

COLD-ADAPTED PROTEASE DERIVED FROM *PSEUDOALTEROMONAS ARCTICA* PAMC 21717 AND USES THEREOF

CROSS-REFERENCE TO RELATED APPLICATION

This application claims priority under the provisions of 35 USC 119 to Korean Patent Application No. 10-2014-0127957 filed Sep. 24, 2014. The disclosure of Korean Patent Application No. 10-2014-0127957 is hereby incorporated herein by reference, in its entirety, for all purposes.

TECHNICAL FIELD

The present invention relates to a cold-adapted protease derived from *Pseudoalteromonas arctica* PAMC 21717 or a recombinant cold-adapted protease obtained by expressing a gene encoding the cold-adapted protease in *E. coli*, and more particularly, to a crystal of a protease exhibiting activity at low temperatures, a method for crystallizing the protease, a method for preparing the protease, a recombinant microorganism that expresses the protease, a method for preparing the recombinant microorganism, a method for preparing the recombinant protease and the use of the cold-adapted protease.

BACKGROUND ART

Proteases are used in various applications, including pharmaceutical compositions such as digestive enzyme agents for alleviating gastrointestinal disorders, thrombolytic agents, or anti-inflammatory agents, and compositions for clothes, contact lenses or cleaners, as well as cosmetics, leather processing agents, food softeners, meat enhancers, feed of food additives, oil and fat separating agents, wastewater treatment, etc. The utility of enzymes among microbial products is already widely known. Proteases account for the highest percentage (60% or higher) of the industrial enzyme market, and the marketability thereof is more and more increasing.

About 25% of industrial proteases are marketed as detergents, and proteases for detergents are required to have a wide spectrum of substrate specificity capable of degrading food, blood or body fluid components, and an alkaline environment, and should be stable so that they do not lose their surfactant activity and enzymatic activity at high temperatures or low temperatures. In the past, plant-derived proteases were mainly used, but in recent years, microorganisms have been most frequently used to produce proteases.

If proteases are to be used for industrial applications, they are required to be very stable. For example, the activity of most proteins decreases or completely disappears in the presence of surfactants, and for this reason, proteases that are used in detergents are extremely limited. Also, if detergents are used at high concentrations, the activity of proteases contained therein is difficult to expect. In addition, conditions such as exposure to extreme pH, exposure to heavy metals, or the degree of oxidation-reduction, all strongly influence the activity of enzymes, and thus if these conditions are out of suitable ranges, enzymes rapidly lose their activity. For this reason, in order for proteases to be regularly used for industrial applications, the proteases are required to maintain their activity even under extreme and unstable physical and chemical conditions.

Serine-based proteases such as subtilisin have been most widely used in the detergent industry. Such basic proteases securely maintain their activity even under high pH conditions in which a surfactant and an oxidizing agent are present (Gupta et al., *Appl Microbiol Biotechnol*, 59:15-32, 2002; Haddar et al., *Bioresour Technol*, 100:3366-3373, 2009), and thus are useful in various industrial applications.

In recent years, a need for cold-active enzymes has increased. Particularly, low-active proteases have been added to detergents, and maintain their high activity at a laundry temperature of 15° C. or lower.

In documents regarding cold-adapted proteases, reported to date, there are reports of the cloning of serine-based cold-active protease genes derived from the psychrophilic microorganism *Shewanella*, the purification and characterization of enzymes (Kulakova et al., *Appl Environ Microbiol*, 65:611-617, 1999), the purification, characterization and sequencing (Huston et al., *Appl Environ Microbiol*, 70:3321-3328, 2004) of the psychrophilic marine microorganism *Colwellia psychrerythraea*, the purification and characterization of cold-adapted serine-based proteases derived from *Colwellia* sp., (Wang et al., *Biotechnol Lett*, 27:1195-1198, 2005) and the like.

Accordingly, the present inventors have made extensive efforts to develop proteases, which are used in various industrial applications, by using a cold-adapted and basic serine-based protease produced from *Pseudoalteromonas arctica* PAMC 21717 isolated from Antarctic Ocean sediments. As a result, the present inventors have isolated a cold-adapted protease that exhibits enzymatic activity under the conditions of 0 to 60° C. and pH 5.0 to 11.0 and then have identified the crystalline structure of the cold-adapted protease, and have found that the cold-adapted protease exhibits high activity at relatively low temperatures compared to proteases such as subtilisin, thereby completing the present invention.

DISCLOSURE OF INVENTION

It is an object of the present invention to provide a crystal of either a cold-adapted protease derived from *Pseudoalteromonas arctica* PAMC 21717 or a recombinant cold-adapted protease obtained by expressing a gene encoding the cold-adapted protease in *E. coli*, and a method for crystallizing the cold-adapted protease.

Another object of the present invention is to provide a method for preparing the cold-adapted protease.

Still another object of the present invention is to provide an enzyme-producing recombinant microorganism that expresses the cold-adapted protease, and a method for preparing the recombinant microorganism.

Yet another object of the present invention is to provide a method for preparing the cold-adapted protease using the recombinant microorganism.

A further object of the present invention is to provide a disinfectant composition for a surgical or therapeutic device, a detergent composition, a feed additive composition, a food additive composition, and a fiber or leather processing composition, the composition containing the cold-adapted protease as an active ingredient.

To achieve the above objects, the present invention provides a crystal of either a cold-adapted protease derived from *Pseudoalteromonas arctica* PAMC 21717 or a recombinant cold-adapted protease obtained by expressing a gene encoding the cold-adapted protease in *E. coli*, wherein the crystal of the cold-adapted protease has the following characteristics: (i) consisting of a subtilisin-like fold; (ii) having four calcium ions and two disulfide bonds (Cys439-Cys442 and Cys207-Cys254); (iii) forming a three-dimensional structure consists ten α-helices which surround the central 6 β-strands and two β-strands; and (iv) having a structure crystallized with P2₁2₁2₁ space group either unit cell parameters of a=47.9 Å, b=74.6 Å, c=83.0 Å, α=β=γ 90° or 2374 atomic coordinates (including 4 calcium ions) set forth in Table 1.

The present invention also a method for crystallizing a cold-adapted protease derived from *Pseudoalteromonas arctica* PAMC 21717 or a recombinant cold-adapted protease obtained by expressing a gene encoding the cold-adapted protease in *E. coli*, wherein the method comprises crystallizing at 20° C. using a protein solution containing 20 mM Tris-HCl (pH 8.0) and 150 mM NaCl, and a preservative solution containing 0.1 M sodium acetate (pH 4.4) and 3 M sodium chloride.

The present invention also provides a method for preparing a cold-adapted protease, the method comprises: (a) fed-batch-culturing *Pseudoalteromonas arctica* PAMC 21717 in a medium containing skim milk, tryptone, $Fe(C_6H_5O_7)$, NaCl, $MgCl_2$, $Na_2SO_4$, $CaCl_2$, $NaHCO_3$ and KBr, to produce a cold-adapted protease (W-pro21717); and (b) recovering the produced cold-adapted protease.

The present invention also provides an enzyme-producing recombinant microorganism, in which a recombinant vector containing an amplification product obtained by PCR using a set of primers of SEQ ID NOs: 7 and 8 is introduced.

The present invention also provides a method for preparing a cold-adapted protease, the method comprises: (a) culturing the above-described recombinant microorganism in a medium containing glucose, $KH_2PO_4$, $(NH_4)_2PO_4$, citric acid, $MgSO_4 7H_2O$, thiamine, an antibiotic and a trace metal element; (b) expressing a cold-adapted protease in the recombinant microorganism to a pH-stat batch culture while supplying a predetermined amount of a medium containing glucose, a yeast extract, $(NH_4)_2PO_4$, $MgSO_4 7H_2O$ and an antibiotic when the pH and DO of the medium is increased; and (c) recovering the expressed cold-adapted protease.

The present invention also provides a disinfectant composition for a surgical or therapeutic device, the composition containing the cold-adapted protease or a crystal of the cold-adapted protease as an active ingredient.

The present invention also provides a detergent composition containing the cold-adapted protease or a crystal of the cold-adapted protease as an active ingredient.

The present invention also provides a feed additive composition containing the cold-adapted protease or a crystal of the cold-adapted protease as an active ingredient.

The present invention also provides a food additive composition containing the cold-adapted protease or a crystal of the cold-adapted protease as an active ingredient.

The present invention also provides a fiber or leather processing composition containing the cold-adapted protease or a crystal of the cold-adapted protease as an active ingredient.

BEST MODE FOR CARRYING OUT THE INVENTION

Figure 1:
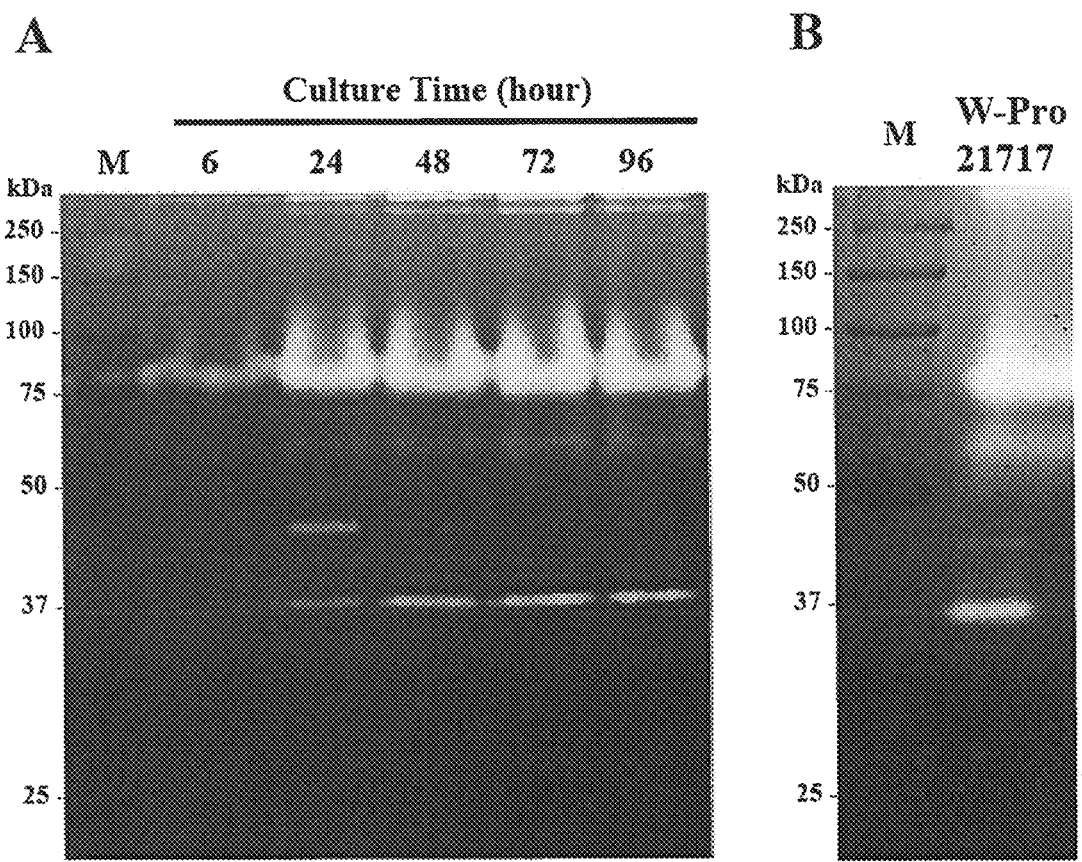
FIG. 1 shows the results of zymogram analysis of a culture of *Pseudoalteromonas arctica* PAMC 21717. (A): time-dependent analysis of the culture by zymogram; and (B) W-Pro21717 partially isolated from a 96-hr culture.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

In the present invention, the three-dimensional crystalline structure and active site of a cold-adapted, basic serine-based protease prepared from *Pseudoalteromonas arctica* PAMC 21717 isolated from Antarctic Ocean sediments were examined, and the characteristics of the protease were analyzed. *Pseudoalteromonas arctica* PAMC 21717 that is used in the present invention was deposited under accession number KCTC 12482BP on Sep. 3, 2013.

In one aspect, the present invention is directed to a crystal of a cold-adapted protease derived from *Pseudoalteromonas arctica* PAMC 21717 or a recombinant cold-adapted protease obtained by expressing a gene encoding the cold-adapted protease in *E. coli*, wherein the crystal of the cold-adapted protease has the following characteristics: (i) consisting of a subtilisin-like fold; (ii) having four calcium ions and two disulfide bonds (Cys439-Cys442 and Cys207-Cys254); (iii) forming a three-dimensional structure consists ten α-helices which surround the central 6 β-strands and two β-strands; and (iv) having a structure crystallized with $P2_12_12_1$ space group either unit cell parameters of a=47.9 Å, b=74.6 Å, c=83.0 Å, α=β=γ 90° or 2374 atomic coordinates (including 4 calcium ions) set forth in Table 1.

In the present invention, a crystal of the protease comprises an enzymatic active site consisting of a catalytic triad of amino acid residues Asp185, His244 and Ser425.

The three-dimensional crystalline structure of the cold-adapted protease of the present invention, including the amino acid sequence SEQ ID NO: 10, can be represented by the atomic coordinates shown in Table 1 below.

TABLE 1

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1 | N | SER | A | 119 | 29.662 | −2.222 | −19.296 | 1.00 | 13.97 |
| ATOM | 2 | CA | SER | A | 119 | 30.116 | −2.772 | −18.080 | 1.00 | 13.32 |
| ATOM | 3 | CB | SER | A | 119 | 30.331 | −1.704 | −17.074 | 1.00 | 17.13 |
| ATOM | 4 | OG | SER | A | 119 | 29.203 | −0.888 | −16.922 | 1.00 | 19.57 |
| ATOM | 5 | C | SER | A | 119 | 29.162 | −3.752 | −17.528 | 1.00 | 12.74 |
| ATOM | 6 | O | SER | A | 119 | 27.947 | −3.671 | −17.841 | 1.00 | 15.90 |
| ATOM | 7 | N | THR | A | 120 | 29.576 | −4.689 | −16.733 | 1.00 | 13.01 |
| ATOM | 8 | CA | THR | A | 120 | 28.740 | −5.705 | −16.131 | 1.00 | 16.10 |
| ATOM | 9 | CB | THR | A | 120 | 29.089 | −7.146 | −16.626 | 1.00 | 22.08 |
| ATOM | 10 | OG1 | THR | A | 120 | 28.606 | −7.278 | −18.004 | 1.00 | 29.55 |
| ATOM | 11 | CG2 | THR | A | 120 | 28.472 | −8.209 | −15.807 | 1.00 | 25.79 |
| ATOM | 12 | C | THR | A | 120 | 28.911 | −5.565 | −14.663 | 1.00 | 14.48 |
| ATOM | 13 | O | THR | A | 120 | 30.046 | −5.623 | −14.148 | 1.00 | 15.53 |
| ATOM | 14 | N | PRO | A | 121 | 27.859 | −5.374 | −13.898 | 1.00 | 11.10 |
| ATOM | 15 | CA | PRO | A | 121 | 28.025 | −5.280 | −12.462 | 1.00 | 11.72 |
| ATOM | 16 | CB | PRO | A | 121 | 26.760 | −4.634 | −12.002 | 1.00 | 13.83 |
| ATOM | 17 | CG | PRO | A | 121 | 25.777 | −5.118 | −12.949 | 1.00 | 13.25 |
| ATOM | 18 | CD | PRO | A | 121 | 26.460 | −5.183 | −14.325 | 1.00 | 12.56 |
| ATOM | 19 | C | PRO | A | 121 | 28.339 | −6.556 | −11.767 | 1.00 | 10.34 |
| ATOM | 20 | O | PRO | A | 121 | 28.139 | −7.601 | −12.301 | 1.00 | 10.98 |
| ATOM | 21 | N | ASN | A | 122 | 28.767 | −6.391 | −10.527 | 1.00 | 10.08 |
| ATOM | 22 | CA | ASN | A | 122 | 29.170 | −7.539 | −9.760 | 1.00 | 10.51 |
| ATOM | 23 | CB | ASN | A | 122 | 30.378 | −7.156 | −8.856 | 1.00 | 11.45 |
| ATOM | 24 | CG | ASN | A | 122 | 29.991 | −6.361 | −7.692 | 1.00 | 11.94 |
| ATOM | 25 | OD1 | ASN | A | 122 | 28.812 | −6.148 | −7.319 | 1.00 | 12.06 |
| ATOM | 26 | ND2 | ASN | A | 122 | 31.000 | −6.035 | −6.884 | 1.00 | 16.58 |
| ATOM | 27 | C | ASN | A | 122 | 28.132 | −8.246 | −8.912 | 1.00 | 10.10 |
| ATOM | 28 | O | ASN | A | 122 | 28.315 | −9.238 | −8.258 | 1.00 | 12.28 |
| ATOM | 29 | N | ASP | A | 123 | 26.863 | −7.783 | −9.066 | 1.00 | 9.30 |
| ATOM | 30 | CA | ASP | A | 123 | 25.823 | −8.343 | −8.254 | 1.00 | 9.23 |
| ATOM | 31 | CB | ASP | A | 123 | 24.538 | −7.490 | −8.474 | 1.00 | 9.04 |
| ATOM | 32 | CG | ASP | A | 123 | 24.792 | −6.042 | −8.214 | 1.00 | 7.86 |
| ATOM | 33 | OD1 | ASP | A | 123 | 25.386 | −5.415 | −9.101 | 1.00 | 8.84 |
| ATOM | 34 | OD2 | ASP | A | 123 | 24.470 | −5.487 | −7.146 | 1.00 | 8.40 |
| ATOM | 35 | C | ASP | A | 123 | 25.609 | −9.820 | −8.560 | 1.00 | 8.58 |
| ATOM | 36 | O | ASP | A | 123 | 25.495 | −10.146 | −9.733 | 1.00 | 9.49 |
| ATOM | 37 | N | PRO | A | 124 | 25.485 | −10.661 | −7.524 | 1.00 | 7.89 |
| ATOM | 38 | CA | PRO | A | 124 | 25.526 | −12.092 | −7.784 | 1.00 | 9.00 |
| ATOM | 39 | CB | PRO | A | 124 | 25.659 | −12.698 | −6.398 | 1.00 | 9.56 |
| ATOM | 40 | CG | PRO | A | 124 | 25.143 | −11.583 | −5.470 | 1.00 | 10.57 |
| ATOM | 41 | CD | PRO | A | 124 | 25.591 | −10.329 | −6.088 | 1.00 | 8.74 |
| ATOM | 42 | C | PRO | A | 124 | 24.335 | −12.604 | −8.533 | 1.00 | 10.01 |
| ATOM | 43 | O | PRO | A | 124 | 24.378 | −13.674 | −9.148 | 1.00 | 12.77 |
| ATOM | 44 | N | ARG | A | 125 | 23.175 | −11.931 | −8.452 | 1.00 | 8.76 |
| ATOM | 45 | CA | ARG | A | 125 | 22.010 | −12.345 | −9.220 | 1.00 | 8.50 |
| ATOM | 46 | CB | ARG | A | 125 | 20.733 | −12.113 | −8.414 | 1.00 | 8.44 |
| ATOM | 47 | CG | ARG | A | 125 | 20.666 | −12.818 | −7.108 | 1.00 | 9.42 |
| ATOM | 48 | CD | ARG | A | 125 | 20.699 | −14.267 | −7.204 | 1.00 | 9.93 |
| ATOM | 49 | NE | ARG | A | 125 | 19.498 | −14.817 | −7.811 | 1.00 | 10.17 |
| ATOM | 50 | CZ | ARG | A | 125 | 18.374 | −15.094 | −7.209 | 1.00 | 10.12 |
| ATOM | 51 | NH1 | ARG | A | 125 | 18.130 | −14.785 | −5.953 | 1.00 | 11.90 |
| ATOM | 52 | NH2 | ARG | A | 125 | 17.366 | −15.651 | −7.925 | 1.00 | 11.95 |
| ATOM | 53 | C | ARG | A | 125 | 21.904 | −11.707 | −10.604 | 1.00 | 7.86 |
| ATOM | 54 | O | ARG | A | 125 | 20.918 | −11.954 | −11.302 | 1.00 | 8.21 |
| ATOM | 55 | N | PHE | A | 126 | 22.827 | −10.872 | −11.028 | 1.00 | 8.60 |
| ATOM | 56 | CA | PHE | A | 126 | 22.801 | −10.249 | −12.361 | 1.00 | 8.84 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 57 | CB | PHE | A | 126 | 24.050 | −9.425 | −12.607 | 1.00 | 9.25 |
| ATOM | 58 | CG | PHE | A | 126 | 24.065 | −8.799 | −13.961 | 1.00 | 9.36 |
| ATOM | 59 | CD1 | PHE | A | 126 | 23.304 | −7.683 | −14.306 | 1.00 | 9.98 |
| ATOM | 60 | CE1 | PHE | A | 126 | 23.363 | −7.209 | −15.599 | 1.00 | 11.58 |
| ATOM | 61 | CZ | PHE | A | 126 | 24.153 | −7.848 | −16.535 | 1.00 | 11.96 |
| ATOM | 62 | CE2 | PHE | A | 126 | 24.880 | −8.914 | −16.188 | 1.00 | 14.57 |
| ATOM | 63 | CD2 | PHE | A | 126 | 24.843 | −9.393 | −14.935 | 1.00 | 13.51 |
| ATOM | 64 | C | PHE | A | 126 | 22.612 | −11.267 | −13.439 | 1.00 | 9.49 |
| ATOM | 65 | O | PHE | A | 126 | 21.837 | −11.052 | −14.352 | 1.00 | 8.19 |
| ATOM | 66 | N | ASP | A | 127 | 23.307 | −12.413 | −13.390 | 1.00 | 9.86 |
| ATOM | 67 | CA | ASP | A | 127 | 23.174 | −13.341 | −14.446 | 1.00 | 10.89 |
| ATOM | 68 | CB | ASP | A | 127 | 24.174 | −14.556 | −14.268 | 1.00 | 15.11 |
| ATOM | 69 | CG | ASP | A | 127 | 25.579 | −14.187 | −14.653 | 1.00 | 22.69 |
| ATOM | 70 | OD1 | ASP | A | 127 | 25.873 | −13.082 | −15.210 | 1.00 | 22.53 |
| ATOM | 71 | OD2 | ASP | A | 127 | 26.444 | −15.024 | −14.308 | 1.00 | 26.82 |
| ATOM | 72 | C | ASP | A | 127 | 21.766 | −13.924 | −14.575 | 1.00 | 9.48 |
| ATOM | 73 | O | ASP | A | 127 | 21.349 | −14.326 | −15.672 | 1.00 | 11.55 |
| ATOM | 74 | N | ASP | A | 128 | 20.999 | −13.981 | −13.480 | 1.00 | 8.00 |
| ATOM | 75 | CA | ASP | A | 128 | 19.615 | −14.385 | −13.521 | 1.00 | 8.20 |
| ATOM | 76 | CB | ASP | A | 128 | 19.094 | −14.733 | −12.101 | 1.00 | 8.81 |
| ATOM | 77 | CG | ASP | A | 128 | 19.722 | −15.981 | −11.478 | 1.00 | 10.78 |
| ATOM | 78 | OD1 | ASP | A | 128 | 20.059 | −16.855 | −12.295 | 1.00 | 12.48 |
| ATOM | 79 | OD2 | ASP | A | 128 | 19.896 | −15.999 | −10.251 | 1.00 | 14.01 |
| ATOM | 80 | C | ASP | A | 128 | 18.689 | −13.291 | −14.160 | 1.00 | 7.71 |
| ATOM | 81 | O | ASP | A | 128 | 17.593 | −13.630 | −14.571 | 1.00 | 7.83 |
| ATOM | 82 | N | GLN | A | 129 | 19.199 | −12.074 | −14.240 | 1.00 | 6.43 |
| ATOM | 83 | CA | GLN | A | 129 | 18.416 | −10.955 | −14.789 | 1.00 | 6.39 |
| ATOM | 84 | CB | GLN | A | 129 | 18.811 | −9.648 | −14.078 | 1.00 | 6.11 |
| ATOM | 85 | CG | GLN | A | 129 | 18.425 | −9.676 | −12.616 | 1.00 | 6.68 |
| ATOM | 86 | CD | GLN | A | 129 | 18.695 | −8.400 | −11.926 | 1.00 | 6.03 |
| ATOM | 87 | OE1 | GLN | A | 129 | 19.840 | −7.979 | −11.719 | 1.00 | 6.44 |
| ATOM | 88 | NE2 | GLN | A | 129 | 17.604 | −7.700 | −11.561 | 1.00 | 6.15 |
| ATOM | 89 | C | GLN | A | 129 | 18.653 | −10.892 | −16.296 | 1.00 | 5.72 |
| ATOM | 90 | O | GLN | A | 129 | 19.160 | −9.980 | −16.866 | 1.00 | 6.33 |
| ATOM | 91 | N | TRP | A | 130 | 18.126 | −11.965 | −16.962 | 1.00 | 6.05 |
| ATOM | 92 | CA | TRP | A | 130 | 18.247 | −12.126 | −18.417 | 1.00 | 6.09 |
| ATOM | 93 | CB | TRP | A | 130 | 17.480 | −13.366 | −18.886 | 1.00 | 5.99 |
| ATOM | 94 | CG | TRP | A | 130 | 16.035 | −13.384 | −18.514 | 1.00 | 5.87 |
| ATOM | 95 | CD1 | TRP | A | 130 | 15.458 | −13.937 | −17.452 | 1.00 | 5.96 |
| ATOM | 96 | NE1 | TRP | A | 130 | 14.116 | −13.655 | −17.416 | 1.00 | 5.57 |
| ATOM | 97 | CE2 | TRP | A | 130 | 13.789 | −12.902 | −18.504 | 1.00 | 5.98 |
| ATOM | 98 | CD2 | TRP | A | 130 | 14.953 | −12.717 | −19.236 | 1.00 | 5.87 |
| ATOM | 99 | CE3 | TRP | A | 130 | 14.861 | −12.000 | −20.434 | 1.00 | 5.98 |
| ATOM | 100 | CZ3 | TRP | A | 130 | 13.643 | −11.463 | −20.799 | 1.00 | 6.46 |
| ATOM | 101 | CH2 | TRP | A | 130 | 12.511 | −11.651 | −20.066 | 1.00 | 6.18 |
| ATOM | 102 | CZ2 | TRP | A | 130 | 12.532 | −12.356 | −18.896 | 1.00 | 5.90 |
| ATOM | 103 | C | TRP | A | 130 | 17.767 | −10.899 | −19.186 | 1.00 | 5.42 |
| ATOM | 104 | O | TRP | A | 130 | 18.228 | −10.555 | −20.278 | 1.00 | 6.46 |
| ATOM | 105 | N | HIS | A | 131 | 16.741 | −10.283 | −18.564 | 1.00 | 4.95 |
| ATOM | 106 | CA | HIS | A | 131 | 16.069 | −9.153 | −19.107 | 1.00 | 5.15 |
| ATOM | 107 | CB | HIS | A | 131 | 14.772 | −8.891 | −18.342 | 1.00 | 5.21 |
| ATOM | 108 | CG | HIS | A | 131 | 14.906 | −9.045 | −16.875 | 1.00 | 4.87 |
| ATOM | 109 | ND1 | HIS | A | 131 | 15.205 | −7.983 | −16.052 | 1.00 | 4.65 |
| ATOM | 110 | CE1 | HIS | A | 131 | 15.363 | −8.469 | −14.813 | 1.00 | 4.50 |
| ATOM | 111 | NE2 | HIS | A | 131 | 15.151 | −9.755 | −14.766 | 1.00 | 5.16 |
| ATOM | 112 | CD2 | HIS | A | 131 | 14.872 | −10.155 | −16.055 | 1.00 | 5.36 |
| ATOM | 113 | C | HIS | A | 131 | 16.929 | −7.890 | −19.263 | 1.00 | 5.25 |
| ATOM | 114 | O | HIS | A | 131 | 16.562 | −6.955 | −19.943 | 1.00 | 5.30 |
| ATOM | 115 | N | TYR | A | 132 | 18.095 | −7.854 | −18.637 | 1.00 | 5.21 |
| ATOM | 116 | CA | TYR | A | 132 | 19.044 | −6.791 | −18.804 | 1.00 | 5.49 |
| ATOM | 117 | CB | TYR | A | 132 | 19.803 | −6.562 | −17.500 | 1.00 | 5.82 |
| ATOM | 118 | CG | TYR | A | 132 | 18.993 | −6.055 | −16.284 | 1.00 | 5.64 |
| ATOM | 119 | CD1 | TYR | A | 132 | 17.693 | −5.548 | −16.424 | 1.00 | 5.42 |
| ATOM | 120 | CE1 | TYR | A | 132 | 17.045 | −5.089 | −15.305 | 1.00 | 5.41 |
| ATOM | 121 | CZ | TYR | A | 132 | 17.649 | −5.123 | −14.072 | 1.00 | 5.62 |
| ATOM | 122 | OH | TYR | A | 132 | 16.948 | −4.640 | −12.949 | 1.00 | 5.68 |
| ATOM | 123 | CE2 | TYR | A | 132 | 18.910 | −5.660 | −13.936 | 1.00 | 6.31 |
| ATOM | 124 | CD2 | TYR | A | 132 | 19.563 | −6.124 | −15.033 | 1.00 | 6.18 |
| ATOM | 125 | C | TYR | A | 132 | 20.044 | −6.965 | −19.907 | 1.00 | 6.62 |
| ATOM | 126 | O | TYR | A | 132 | 20.582 | −5.969 | −20.367 | 1.00 | 7.65 |
| ATOM | 127 | N | TYR | A | 133 | 20.283 | −8.213 | −20.307 | 1.00 | 7.67 |
| ATOM | 128 | CA | TYR | A | 133 | 21.479 | −8.416 | −21.169 | 1.00 | 8.37 |
| ATOM | 129 | CB | TYR | A | 133 | 22.705 | −8.809 | −20.299 | 1.00 | 8.45 |
| ATOM | 130 | CG | TYR | A | 133 | 22.630 | −10.151 | −19.668 | 1.00 | 8.83 |
| ATOM | 131 | CD1 | TYR | A | 133 | 23.098 | −11.270 | −20.341 | 1.00 | 10.06 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 132 | CE1 | TYR | A | 133 | 23.071 | −12.473 | −19.825 | 1.00 | 9.95 |
| ATOM | 133 | CZ | TYR | A | 133 | 22.501 | −12.738 | −18.554 | 1.00 | 9.62 |
| ATOM | 134 | OH | TYR | A | 133 | 22.403 | −13.985 | −18.058 | 1.00 | 10.83 |
| ATOM | 135 | CE2 | TYR | A | 133 | 22.009 | −11.572 | −17.816 | 1.00 | 8.72 |
| ATOM | 136 | CD2 | TYR | A | 133 | 22.115 | −10.371 | −18.399 | 1.00 | 8.80 |
| ATOM | 137 | C | TYR | A | 133 | 21.329 | −9.511 | −22.209 | 1.00 | 9.19 |
| ATOM | 138 | O | TYR | A | 133 | 22.199 | −9.523 | −23.145 | 1.00 | 9.96 |
| ATOM | 139 | N | GLU | A | 134 | 20.391 | −10.422 | −22.157 | 1.00 | 8.11 |
| ATOM | 140 | CA | GLU | A | 134 | 20.365 | −11.521 | −23.238 | 1.00 | 7.08 |
| ATOM | 141 | CB | GLU | A | 134 | 19.391 | −12.595 | −22.845 | 1.00 | 8.11 |
| ATOM | 142 | CG | GLU | A | 134 | 19.934 | −13.532 | −21.869 | 1.00 | 8.82 |
| ATOM | 143 | CD | GLU | A | 134 | 19.116 | −14.781 | −21.637 | 1.00 | 9.85 |
| ATOM | 144 | OE1 | GLU | A | 134 | 17.957 | −14.861 | −22.076 | 1.00 | 8.68 |
| ATOM | 145 | OE2 | GLU | A | 134 | 19.616 | −15.714 | −20.952 | 1.00 | 11.89 |
| ATOM | 146 | C | GLU | A | 134 | 19.953 | −10.899 | −24.550 | 1.00 | 8.65 |
| ATOM | 147 | O | GLU | A | 134 | 19.203 | −9.935 | −24.656 | 1.00 | 8.62 |
| ATOM | 148 | N | GLN | A | 135 | 20.450 | −11.509 | −25.671 | 1.00 | 9.63 |
| ATOM | 149 | CA | GLN | A | 135 | 20.189 | −10.943 | −26.968 | 1.00 | 10.15 |
| ATOM | 150 | CB | GLN | A | 135 | 21.054 | −11.685 | −28.032 | 1.00 | 12.60 |
| ATOM | 151 | CG | GLN | A | 135 | 22.542 | −11.350 | −27.805 | 1.00 | 18.13 |
| ATOM | 152 | CD | GLN | A | 135 | 22.879 | −9.873 | −27.878 | 1.00 | 26.31 |
| ATOM | 153 | OE1 | GLN | A | 135 | 23.520 | −9.267 | −26.969 | 1.00 | 26.28 |
| ATOM | 154 | NE2 | GLN | A | 135 | 22.435 | −9.267 | −28.962 | 1.00 | 27.49 |
| ATOM | 155 | C | GLN | A | 135 | 18.693 | −10.990 | −27.366 | 1.00 | 8.55 |
| ATOM | 156 | O | GLN | A | 135 | 18.198 | −10.067 | −27.967 | 1.00 | 10.28 |
| ATOM | 157 | N | ALA | A | 136 | 18.019 | −12.059 | −27.081 | 1.00 | 8.00 |
| ATOM | 158 | CA | ALA | A | 136 | 16.653 | −12.189 | −27.590 | 1.00 | 7.69 |
| ATOM | 159 | CB | ALA | A | 136 | 16.153 | −13.621 | −27.496 | 1.00 | 9.15 |
| ATOM | 160 | C | ALA | A | 136 | 15.701 | −11.229 | −26.878 | 1.00 | 7.63 |
| ATOM | 161 | O | ALA | A | 136 | 14.955 | −10.490 | −27.577 | 1.00 | 7.99 |
| ATOM | 162 | N | GLY | A | 137 | 15.668 | −11.243 | −25.574 | 1.00 | 7.71 |
| ATOM | 163 | CA | GLY | A | 137 | 14.631 | −10.510 | −24.800 | 1.00 | 7.92 |
| ATOM | 164 | C | GLY | A | 137 | 15.204 | −9.425 | −23.890 | 1.00 | 7.52 |
| ATOM | 165 | O | GLY | A | 137 | 14.391 | −8.776 | −23.200 | 1.00 | 8.16 |
| ATOM | 166 | N | GLY | A | 138 | 16.490 | −9.148 | −23.899 | 1.00 | 5.93 |
| ATOM | 167 | CA | GLY | A | 138 | 17.042 | −8.195 | −22.980 | 1.00 | 6.11 |
| ATOM | 168 | C | GLY | A | 138 | 17.106 | −6.795 | −23.466 | 1.00 | 6.67 |
| ATOM | 169 | O | GLY | A | 138 | 16.886 | −6.459 | −24.627 | 1.00 | 6.87 |
| ATOM | 170 | N | LEU | A | 139 | 17.411 | −5.885 | −22.510 | 1.00 | 6.36 |
| ATOM | 171 | CA | LEU | A | 139 | 17.382 | −4.450 | −22.709 | 1.00 | 6.71 |
| ATOM | 172 | CB | LEU | A | 139 | 16.980 | −3.756 | −21.396 | 1.00 | 6.50 |
| ATOM | 173 | CG | LEU | A | 139 | 16.164 | −2.485 | −21.503 | 1.00 | 6.37 |
| ATOM | 174 | CD1 | LEU | A | 139 | 14.747 | −2.724 | −21.977 | 1.00 | 7.38 |
| ATOM | 175 | CD2 | LEU | A | 139 | 16.209 | −1.738 | −20.179 | 1.00 | 7.55 |
| ATOM | 176 | C | LEU | A | 139 | 18.666 | −3.828 | −23.247 | 1.00 | 6.39 |
| ATOM | 177 | O | LEU | A | 139 | 18.747 | −2.612 | −23.425 | 1.00 | 6.92 |
| ATOM | 178 | N | ASN | A | 140 | 19.711 | −4.644 | −23.442 | 1.00 | 7.10 |
| ATOM | 179 | CA | ASN | A | 140 | 20.991 | −4.183 | −23.965 | 1.00 | 7.46 |
| ATOM | 180 | CB | ASN | A | 140 | 20.855 | −3.698 | −25.435 | 1.00 | 8.40 |
| ATOM | 181 | CG | ASN | A | 140 | 22.156 | −3.735 | −26.199 | 1.00 | 8.55 |
| ATOM | 182 | OD1 | ASN | A | 140 | 23.057 | −4.554 | −25.874 | 1.00 | 12.09 |
| ATOM | 183 | ND2 | ASN | A | 140 | 22.273 | −2.863 | −27.147 | 1.00 | 9.75 |
| ATOM | 184 | C | ASN | A | 140 | 21.621 | −3.140 | −23.075 | 1.00 | 7.14 |
| ATOM | 185 | O | ASN | A | 140 | 22.116 | −2.130 | −23.565 | 1.00 | 8.27 |
| ATOM | 186 | N | LEU | A | 141 | 21.622 | −3.431 | −21.771 | 1.00 | 6.74 |
| ATOM | 187 | CA | LEU | A | 141 | 22.118 | −2.479 | −20.756 | 1.00 | 6.84 |
| ATOM | 188 | CB | LEU | A | 141 | 21.472 | −2.767 | −19.455 | 1.00 | 6.87 |
| ATOM | 189 | CG | LEU | A | 141 | 20.085 | −2.141 | −19.336 | 1.00 | 6.24 |
| ATOM | 190 | CD1 | LEU | A | 141 | 19.255 | −2.811 | −18.259 | 1.00 | 6.64 |
| ATOM | 191 | CD2 | LEU | A | 141 | 20.188 | −0.624 | −19.106 | 1.00 | 6.68 |
| ATOM | 192 | C | LEU | A | 141 | 23.649 | −2.416 | −20.632 | 1.00 | 7.84 |
| ATOM | 193 | O | LEU | A | 141 | 24.143 | −1.318 | −20.401 | 1.00 | 8.32 |
| ATOM | 194 | N | PRO | A | 142 | 24.408 | −3.537 | −20.688 | 1.00 | 7.52 |
| ATOM | 195 | CA | PRO | A | 142 | 25.845 | −3.365 | −20.360 | 1.00 | 7.97 |
| ATOM | 196 | CB | PRO | A | 142 | 26.378 | −4.793 | −20.623 | 1.00 | 9.69 |
| ATOM | 197 | CG | PRO | A | 142 | 25.239 | −5.692 | −20.199 | 1.00 | 9.00 |
| ATOM | 198 | CD | PRO | A | 142 | 24.013 | −4.948 | −20.773 | 1.00 | 8.29 |
| ATOM | 199 | C | PRO | A | 142 | 26.525 | −2.304 | −21.176 | 1.00 | 8.88 |
| ATOM | 200 | O | PRO | A | 142 | 27.301 | −1.479 | −20.549 | 1.00 | 9.95 |
| ATOM | 201 | N | THR | A | 143 | 26.301 | −2.181 | −22.438 | 1.00 | 9.83 |
| ATOM | 202 | CA | THR | A | 143 | 26.899 | −1.154 | −23.210 | 1.00 | 10.77 |
| ATOM | 203 | CB | THR | A | 143 | 26.687 | −1.432 | −24.765 | 1.00 | 14.94 |
| ATOM | 204 | OG1 | THR | A | 143 | 27.409 | −2.654 | −24.983 | 1.00 | 21.55 |
| ATOM | 205 | CG2 | THR | A | 143 | 27.216 | −0.226 | −25.618 | 1.00 | 16.90 |
| ATOM | 206 | C | THR | A | 143 | 26.403 | 0.221 | −22.865 | 1.00 | 10.24 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 207 | O | THR | A | 143 | 27.100 | 1.234 | −22.849 | 1.00 | 10.72 |
| ATOM | 208 | N | ALA | A | 144 | 25.073 | 0.324 | −22.537 | 1.00 | 8.50 |
| ATOM | 209 | CA | ALA | A | 144 | 24.550 | 1.598 | −22.122 | 1.00 | 8.05 |
| ATOM | 210 | CB | ALA | A | 144 | 23.035 | 1.470 | −21.898 | 1.00 | 7.44 |
| ATOM | 211 | C | ALA | A | 144 | 25.237 | 2.144 | −20.866 | 1.00 | 7.32 |
| ATOM | 212 | O | ALA | A | 144 | 25.521 | 3.361 | −20.786 | 1.00 | 7.84 |
| ATOM | 213 | N | TRP | A | 145 | 25.455 | 1.256 | −19.926 | 1.00 | 7.73 |
| ATOM | 214 | CA | TRP | A | 145 | 26.081 | 1.627 | −18.629 | 1.00 | 7.48 |
| ATOM | 215 | CB | TRP | A | 145 | 26.021 | 0.462 | −17.729 | 1.00 | 6.84 |
| ATOM | 216 | CG | TRP | A | 145 | 24.613 | 0.115 | −17.183 | 1.00 | 6.67 |
| ATOM | 217 | CD1 | TRP | A | 145 | 23.595 | 0.983 | −16.893 | 1.00 | 6.81 |
| ATOM | 218 | NE1 | TRP | A | 145 | 22.583 | 0.308 | −16.369 | 1.00 | 6.25 |
| ATOM | 219 | CE2 | TRP | A | 145 | 22.856 | −1.019 | −16.269 | 1.00 | 6.87 |
| ATOM | 220 | CD2 | TRP | A | 145 | 24.178 | −1.164 | −16.783 | 1.00 | 6.25 |
| ATOM | 221 | CE3 | TRP | A | 145 | 24.731 | −2.467 | −16.817 | 1.00 | 7.18 |
| ATOM | 222 | CZ3 | TRP | A | 145 | 24.046 | −3.500 | −16.388 | 1.00 | 8.07 |
| ATOM | 223 | CH2 | TRP | A | 145 | 22.690 | −3.309 | −15.862 | 1.00 | 9.20 |
| ATOM | 224 | CZ2 | TRP | A | 145 | 22.167 | −2.079 | −15.751 | 1.00 | 7.47 |
| ATOM | 225 | C | TRP | A | 145 | 27.517 | 2.122 | −18.805 | 1.00 | 8.30 |
| ATOM | 226 | O | TRP | A | 145 | 27.986 | 2.809 | −17.866 | 1.00 | 9.06 |
| ATOM | 227 | N | ASP | A | 146 | 28.195 | 1.887 | −19.921 | 1.00 | 9.00 |
| ATOM | 228 | CA | ASP | A | 146 | 29.496 | 2.522 | −20.187 | 1.00 | 9.41 |
| ATOM | 229 | CB | ASP | A | 146 | 30.070 | 1.930 | −21.484 | 1.00 | 9.73 |
| ATOM | 230 | CG | ASP | A | 146 | 30.506 | 0.542 | −21.315 | 1.00 | 11.08 |
| ATOM | 231 | OD1 | ASP | A | 146 | 30.815 | 0.077 | −20.211 | 1.00 | 13.32 |
| ATOM | 232 | OD2 | ASP | A | 146 | 30.435 | −0.198 | −22.373 | 1.00 | 15.55 |
| ATOM | 233 | C | ASP | A | 146 | 29.360 | 4.003 | −20.245 | 1.00 | 12.39 |
| ATOM | 234 | O | ASP | A | 146 | 30.387 | 4.736 | −20.091 | 1.00 | 13.71 |
| ATOM | 235 | N | THR | A | 147 | 28.180 | 4.585 | −20.570 | 1.00 | 11.95 |
| ATOM | 236 | CA | THR | A | 147 | 27.963 | 6.012 | −20.807 | 1.00 | 13.21 |
| ATOM | 237 | CB | THR | A | 147 | 27.273 | 6.162 | −22.303 | 1.00 | 12.96 |
| ATOM | 238 | OG1 | THR | A | 147 | 28.267 | 5.662 | −23.258 | 1.00 | 24.83 |
| ATOM | 239 | CG2 | THR | A | 147 | 27.031 | 7.563 | −22.606 | 1.00 | 21.42 |
| ATOM | 240 | C | THR | A | 147 | 27.015 | 6.650 | −19.796 | 1.00 | 10.15 |
| ATOM | 241 | O | THR | A | 147 | 27.076 | 7.814 | −19.455 | 1.00 | 10.91 |
| ATOM | 242 | N | ALA | A | 148 | 25.948 | 5.897 | −19.361 | 1.00 | 8.46 |
| ATOM | 243 | CA | ALA | A | 148 | 24.923 | 6.494 | −18.501 | 1.00 | 8.41 |
| ATOM | 244 | CB | ALA | A | 148 | 23.760 | 7.022 | −19.329 | 1.00 | 9.12 |
| ATOM | 245 | C | ALA | A | 148 | 24.422 | 5.417 | −17.548 | 1.00 | 7.39 |
| ATOM | 246 | O | ALA | A | 148 | 24.166 | 4.293 | −17.935 | 1.00 | 7.98 |
| ATOM | 247 | N | THR | A | 149 | 24.113 | 5.880 | −16.348 | 1.00 | 7.48 |
| ATOM | 248 | CA | THR | A | 149 | 23.594 | 5.028 | −15.231 | 1.00 | 7.88 |
| ATOM | 249 | CB | THR | A | 149 | 24.690 | 4.681 | −14.254 | 1.00 | 8.71 |
| ATOM | 250 | OG1 | THR | A | 149 | 25.259 | 5.926 | −13.759 | 1.00 | 9.67 |
| ATOM | 251 | CG2 | THR | A | 149 | 25.759 | 3.827 | −14.939 | 1.00 | 9.70 |
| ATOM | 252 | C | THR | A | 149 | 22.418 | 5.693 | −14.478 | 1.00 | 6.60 |
| ATOM | 253 | O | THR | A | 149 | 21.920 | 5.103 | −13.521 | 1.00 | 7.10 |
| ATOM | 254 | N | GLY | A | 150 | 22.030 | 6.873 | −14.891 | 1.00 | 7.48 |
| ATOM | 255 | CA | GLY | A | 150 | 20.979 | 7.631 | −14.186 | 1.00 | 7.06 |
| ATOM | 256 | C | GLY | A | 150 | 21.390 | 8.566 | −13.157 | 1.00 | 7.91 |
| ATOM | 257 | O | GLY | A | 150 | 20.572 | 9.141 | −12.468 | 1.00 | 7.26 |
| ATOM | 258 | N | SER | A | 151 | 22.723 | 8.812 | −13.050 | 1.00 | 8.63 |
| ATOM | 259 | CA | SER | A | 151 | 23.218 | 9.771 | −12.004 | 1.00 | 8.89 |
| ATOM | 260 | CB | SER | A | 151 | 24.681 | 10.023 | −12.257 | 1.00 | 12.29 |
| ATOM | 261 | OG | SER | A | 151 | 25.413 | 8.877 | −12.137 | 1.00 | 18.84 |
| ATOM | 262 | C | SER | A | 151 | 22.547 | 11.127 | −12.114 | 1.00 | 8.29 |
| ATOM | 263 | O | SER | A | 151 | 22.452 | 11.690 | −13.199 | 1.00 | 9.10 |
| ATOM | 264 | N | GLY | A | 152 | 21.990 | 11.609 | −10.979 | 1.00 | 9.13 |
| ATOM | 265 | CA | GLY | A | 152 | 21.363 | 12.902 | −10.954 | 1.00 | 9.18 |
| ATOM | 266 | C | GLY | A | 152 | 19.882 | 12.926 | −11.330 | 1.00 | 10.01 |
| ATOM | 267 | O | GLY | A | 152 | 19.272 | 14.021 | −11.318 | 1.00 | 13.79 |
| ATOM | 268 | N | VAL | A | 153 | 19.349 | 11.792 | −11.704 | 1.00 | 7.27 |
| ATOM | 269 | CA | VAL | A | 153 | 17.959 | 11.716 | −12.202 | 1.00 | 6.62 |
| ATOM | 270 | CB | VAL | A | 153 | 17.957 | 10.865 | −13.499 | 1.00 | 6.53 |
| ATOM | 271 | CG1 | VAL | A | 153 | 16.564 | 10.809 | −14.055 | 1.00 | 6.48 |
| ATOM | 272 | CG2 | VAL | A | 153 | 18.898 | 11.454 | −14.525 | 1.00 | 7.05 |
| ATOM | 273 | C | VAL | A | 153 | 17.081 | 11.105 | −11.134 | 1.00 | 5.94 |
| ATOM | 274 | O | VAL | A | 153 | 17.521 | 10.270 | −10.339 | 1.00 | 6.77 |
| ATOM | 275 | N | VAL | A | 154 | 15.818 | 11.578 | −11.092 | 1.00 | 6.25 |
| ATOM | 276 | CA | VAL | A | 154 | 14.821 | 11.139 | −10.143 | 1.00 | 5.63 |
| ATOM | 277 | CB | VAL | A | 154 | 14.333 | 12.307 | −9.267 | 1.00 | 6.01 |
| ATOM | 278 | CG1 | VAL | A | 154 | 13.200 | 11.879 | −8.345 | 1.00 | 6.81 |
| ATOM | 279 | CG2 | VAL | A | 154 | 15.484 | 12.865 | −8.462 | 1.00 | 7.80 |
| ATOM | 280 | C | VAL | A | 154 | 13.658 | 10.463 | −10.874 | 1.00 | 5.23 |
| ATOM | 281 | O | VAL | A | 154 | 13.100 | 11.060 | −11.821 | 1.00 | 6.11 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 282 | N | VAL | A | 155 | 13.339 | 9.260 | −10.425 | 1.00 | 5.35 |
| ATOM | 283 | CA | VAL | A | 155 | 12.200 | 8.499 | −10.938 | 1.00 | 4.93 |
| ATOM | 284 | CB | VAL | A | 155 | 12.638 | 7.114 | −11.529 | 1.00 | 4.95 |
| ATOM | 285 | CG1 | VAL | A | 155 | 11.422 | 6.374 | −12.101 | 1.00 | 5.12 |
| ATOM | 286 | CG2 | VAL | A | 155 | 13.742 | 7.265 | −12.562 | 1.00 | 5.75 |
| ATOM | 287 | C | VAL | A | 155 | 11.196 | 8.336 | −9.878 | 1.00 | 4.39 |
| ATOM | 288 | O | VAL | A | 155 | 11.490 | 7.763 | −8.814 | 1.00 | 5.65 |
| ATOM | 289 | N | ALA | A | 156 | 9.953 | 8.791 | −10.097 | 1.00 | 4.41 |
| ATOM | 290 | CA | ALA | A | 156 | 8.840 | 8.527 | −9.147 | 1.00 | 4.84 |
| ATOM | 291 | CB | ALA | A | 156 | 7.903 | 9.733 | −9.116 | 1.00 | 5.28 |
| ATOM | 292 | C | ALA | A | 156 | 8.167 | 7.230 | −9.548 | 1.00 | 4.82 |
| ATOM | 293 | O | ALA | A | 156 | 7.791 | 7.055 | −10.697 | 1.00 | 6.06 |
| ATOM | 294 | N | VAL | A | 157 | 8.000 | 6.341 | −8.591 | 1.00 | 4.18 |
| ATOM | 295 | CA | VAL | A | 157 | 7.340 | 5.029 | −8.780 | 1.00 | 4.79 |
| ATOM | 296 | CB | VAL | A | 157 | 8.208 | 3.888 | −8.288 | 1.00 | 5.10 |
| ATOM | 297 | CG1 | VAL | A | 157 | 7.441 | 2.614 | −8.261 | 1.00 | 5.83 |
| ATOM | 298 | CG2 | VAL | A | 157 | 9.456 | 3.788 | −9.128 | 1.00 | 5.17 |
| ATOM | 299 | C | VAL | A | 157 | 6.017 | 5.108 | −8.084 | 1.00 | 4.51 |
| ATOM | 300 | O | VAL | A | 157 | 5.972 | 5.181 | −6.840 | 1.00 | 4.98 |
| ATOM | 301 | N | LEU | A | 158 | 4.918 | 5.155 | −8.848 | 1.00 | 4.40 |
| ATOM | 302 | CA | LEU | A | 158 | 3.559 | 5.297 | −8.329 | 1.00 | 4.68 |
| ATOM | 303 | CB | LEU | A | 158 | 2.714 | 6.194 | −9.247 | 1.00 | 5.68 |
| ATOM | 304 | CG | LEU | A | 158 | 2.828 | 7.695 | −9.027 | 1.00 | 6.39 |
| ATOM | 305 | CD1 | LEU | A | 158 | 4.251 | 8.181 | −9.264 | 1.00 | 6.73 |
| ATOM | 306 | CD2 | LEU | A | 158 | 1.889 | 8.435 | −9.973 | 1.00 | 7.00 |
| ATOM | 307 | C | LEU | A | 158 | 2.989 | 3.925 | −8.212 | 1.00 | 4.90 |
| ATOM | 308 | O | LEU | A | 158 | 2.713 | 3.294 | −9.249 | 1.00 | 5.24 |
| ATOM | 309 | N | ASP | A | 159 | 2.855 | 3.386 | −7.008 | 1.00 | 5.11 |
| ATOM | 310 | CA | ASP | A | 159 | 2.662 | 1.949 | −6.851 | 1.00 | 5.57 |
| ATOM | 311 | CB | ASP | A | 159 | 3.981 | 1.213 | −7.238 | 1.00 | 5.88 |
| ATOM | 312 | CG | ASP | A | 159 | 3.761 | −0.070 | −7.839 | 1.00 | 7.36 |
| ATOM | 313 | OD1 | ASP | A | 159 | 3.235 | −0.982 | −7.184 | 1.00 | 7.67 |
| ATOM | 314 | OD2 | ASP | A | 159 | 4.146 | −0.313 | −8.995 | 1.00 | 8.72 |
| ATOM | 315 | C | ASP | A | 159 | 2.136 | 1.689 | −5.475 | 1.00 | 5.20 |
| ATOM | 316 | O | ASP | A | 159 | 1.513 | 2.554 | −4.799 | 1.00 | 5.18 |
| ATOM | 317 | N | THR | A | 160 | 2.429 | 0.477 | −4.959 | 1.00 | 4.95 |
| ATOM | 318 | CA | THR | A | 160 | 1.925 | 0.033 | −3.650 | 1.00 | 5.28 |
| ATOM | 319 | CB | THR | A | 160 | 1.822 | −1.517 | −3.571 | 1.00 | 5.73 |
| ATOM | 320 | OG1 | THR | A | 160 | 3.187 | −2.060 | −3.602 | 1.00 | 6.05 |
| ATOM | 321 | CG2 | THR | A | 160 | 1.042 | −2.101 | −4.719 | 1.00 | 6.49 |
| ATOM | 322 | C | THR | A | 160 | 2.739 | 0.549 | −2.473 | 1.00 | 5.53 |
| ATOM | 323 | O | THR | A | 160 | 2.405 | 0.243 | −1.335 | 1.00 | 6.23 |
| ATOM | 324 | N | GLY | A | 161 | 3.789 | 1.313 | −2.745 | 1.00 | 5.28 |
| ATOM | 325 | CA | GLY | A | 161 | 4.774 | 1.664 | −1.762 | 1.00 | 5.79 |
| ATOM | 326 | C | GLY | A | 161 | 5.983 | 0.811 | −1.821 | 1.00 | 5.26 |
| ATOM | 327 | O | GLY | A | 161 | 6.169 | 0.052 | −2.800 | 1.00 | 6.39 |
| ATOM | 328 | N | TYR | A | 162 | 6.844 | 0.848 | −0.827 | 1.00 | 5.56 |
| ATOM | 329 | CA | TYR | A | 162 | 8.097 | 0.075 | −0.835 | 1.00 | 5.56 |
| ATOM | 330 | CB | TYR | A | 162 | 9.265 | 0.926 | −1.314 | 1.00 | 6.51 |
| ATOM | 331 | CG | TYR | A | 162 | 9.733 | 1.923 | −0.293 | 1.00 | 6.58 |
| ATOM | 332 | CD1 | TYR | A | 162 | 9.012 | 3.044 | 0.058 | 1.00 | 6.65 |
| ATOM | 333 | CE1 | TYR | A | 162 | 9.405 | 3.876 | 1.035 | 1.00 | 7.04 |
| ATOM | 334 | CZ | TYR | A | 162 | 10.553 | 3.647 | 1.718 | 1.00 | 7.73 |
| ATOM | 335 | OH | TYR | A | 162 | 10.955 | 4.541 | 2.705 | 1.00 | 10.14 |
| ATOM | 336 | CE2 | TYR | A | 162 | 11.315 | 2.597 | 1.409 | 1.00 | 7.11 |
| ATOM | 337 | CD2 | TYR | A | 162 | 10.919 | 1.754 | 0.418 | 1.00 | 7.03 |
| ATOM | 338 | C | TYR | A | 162 | 8.391 | −0.502 | 0.557 | 1.00 | 5.64 |
| ATOM | 339 | O | TYR | A | 162 | 7.876 | 0.032 | 1.557 | 1.00 | 5.57 |
| ATOM | 340 | N | ARG | A | 163 | 9.228 | −1.532 | 0.581 | 1.00 | 5.90 |
| ATOM | 341 | CA | ARG | A | 163 | 9.928 | −1.887 | 1.825 | 1.00 | 7.08 |
| ATOM | 342 | CB | ARG | A | 163 | 9.820 | −3.355 | 2.128 | 1.00 | 7.63 |
| ATOM | 343 | CG | ARG | A | 163 | 8.436 | −3.879 | 2.345 | 1.00 | 7.54 |
| ATOM | 344 | CD | ARG | A | 163 | 7.603 | −3.123 | 3.314 | 1.00 | 7.64 |
| ATOM | 345 | NE | ARG | A | 163 | 8.278 | −2.861 | 4.582 | 1.00 | 6.89 |
| ATOM | 346 | CZ | ARG | A | 163 | 7.794 | −2.034 | 5.522 | 1.00 | 7.32 |
| ATOM | 347 | NH1 | ARG | A | 163 | 8.544 | −1.769 | 6.574 | 1.00 | 7.85 |
| ATOM | 348 | NH2 | ARG | A | 163 | 6.649 | −1.487 | 5.354 | 1.00 | 7.79 |
| ATOM | 349 | C | ARG | A | 163 | 11.367 | −1.478 | 1.684 | 1.00 | 7.26 |
| ATOM | 350 | O | ARG | A | 163 | 11.938 | −1.468 | 0.556 | 1.00 | 6.77 |
| ATOM | 351 | N | PRO | A | 164 | 12.034 | −1.113 | 2.782 | 1.00 | 7.12 |
| ATOM | 352 | CA | PRO | A | 164 | 13.416 | −0.633 | 2.751 | 1.00 | 7.02 |
| ATOM | 353 | CB | PRO | A | 164 | 13.555 | 0.093 | 4.102 | 1.00 | 7.65 |
| ATOM | 354 | CG | PRO | A | 164 | 12.750 | −0.758 | 4.978 | 1.00 | 7.06 |
| ATOM | 355 | CD | PRO | A | 164 | 11.498 | −1.079 | 4.178 | 1.00 | 6.95 |
| ATOM | 356 | C | PRO | A | 164 | 14.427 | −1.764 | 2.598 | 1.00 | 7.37 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 357 | O | PRO | A | 164 | 15.363 | −1.954 | 3.411 | 1.00 | 7.96 |
| ATOM | 358 | N | HIS | A | 165 | 14.290 | −2.481 | 1.522 | 1.00 | 6.81 |
| ATOM | 359 | CA | HIS | A | 165 | 15.125 | −3.673 | 1.223 | 1.00 | 6.19 |
| ATOM | 360 | CB | HIS | A | 165 | 14.679 | −4.200 | −0.176 | 1.00 | 6.54 |
| ATOM | 361 | CG | HIS | A | 165 | 15.271 | −5.517 | −0.551 | 1.00 | 6.60 |
| ATOM | 362 | ND1 | HIS | A | 165 | 16.618 | −5.748 | −0.705 | 1.00 | 6.75 |
| ATOM | 363 | CE1 | HIS | A | 165 | 16.771 | −7.001 | −1.106 | 1.00 | 6.97 |
| ATOM | 364 | NE2 | HIS | A | 165 | 15.569 | −7.536 | −1.252 | 1.00 | 7.18 |
| ATOM | 365 | CD2 | HIS | A | 165 | 14.625 | −6.634 | −0.908 | 1.00 | 6.70 |
| ATOM | 366 | C | HIS | A | 165 | 16.567 | −3.227 | 1.250 | 1.00 | 6.19 |
| ATOM | 367 | O | HIS | A | 165 | 16.940 | −2.172 | 0.713 | 1.00 | 6.52 |
| ATOM | 368 | N | ALA | A | 166 | 17.412 | −4.085 | 1.794 | 1.00 | 6.05 |
| ATOM | 369 | CA | ALA | A | 166 | 18.841 | −3.807 | 1.833 | 1.00 | 6.22 |
| ATOM | 370 | CB | ALA | A | 166 | 19.614 | −4.979 | 2.497 | 1.00 | 7.60 |
| ATOM | 371 | C | ALA | A | 166 | 19.509 | −3.517 | 0.535 | 1.00 | 6.60 |
| ATOM | 372 | O | ALA | A | 166 | 20.508 | −2.802 | 0.426 | 1.00 | 7.57 |
| ATOM | 373 | N | ASP | A | 167 | 18.901 | −4.071 | −0.574 | 1.00 | 6.35 |
| ATOM | 374 | CA | ASP | A | 167 | 19.455 | −3.860 | −1.928 | 1.00 | 6.24 |
| ATOM | 375 | CB | ASP | A | 167 | 19.486 | −5.159 | −2.748 | 1.00 | 6.79 |
| ATOM | 376 | CG | ASP | A | 167 | 20.595 | −5.255 | −3.726 | 1.00 | 7.36 |
| ATOM | 377 | OD1 | ASP | A | 167 | 21.695 | −4.689 | −3.476 | 1.00 | 7.55 |
| ATOM | 378 | OD2 | ASP | A | 167 | 20.397 | −5.910 | −4.814 | 1.00 | 6.66 |
| ATOM | 379 | C | ASP | A | 167 | 18.764 | −2.761 | −2.723 | 1.00 | 6.29 |
| ATOM | 380 | O | ASP | A | 167 | 18.869 | −2.673 | −3.912 | 1.00 | 6.98 |
| ATOM | 381 | N | LEU | A | 168 | 17.996 | −1.941 | −1.964 | 1.00 | 6.39 |
| ATOM | 382 | CA | LEU | A | 168 | 17.204 | −0.839 | −2.585 | 1.00 | 6.26 |
| ATOM | 383 | CB | LEU | A | 168 | 15.713 | −1.293 | −2.633 | 1.00 | 7.18 |
| ATOM | 384 | CG | LEU | A | 168 | 14.749 | −0.313 | −3.306 | 1.00 | 8.10 |
| ATOM | 385 | CD1 | LEU | A | 168 | 15.153 | 0.006 | −4.742 | 1.00 | 9.20 |
| ATOM | 386 | CD2 | LEU | A | 168 | 13.363 | −0.861 | −3.191 | 1.00 | 9.23 |
| ATOM | 387 | C | LEU | A | 168 | 17.343 | 0.471 | −1.818 | 1.00 | 6.50 |
| ATOM | 388 | O | LEU | A | 168 | 17.319 | 1.541 | −2.420 | 1.00 | 6.32 |
| ATOM | 389 | N | ASN | A | 169 | 17.295 | 0.404 | −0.483 | 1.00 | 6.84 |
| ATOM | 390 | CA | ASN | A | 169 | 16.980 | 1.614 | 0.302 | 1.00 | 7.08 |
| ATOM | 391 | CB | ASN | A | 169 | 16.843 | 1.239 | 1.785 | 1.00 | 8.36 |
| ATOM | 392 | CG | ASN | A | 169 | 16.147 | 2.245 | 2.526 | 1.00 | 10.04 |
| ATOM | 393 | OD1 | ASN | A | 169 | 16.751 | 2.855 | 3.514 | 1.00 | 16.72 |
| ATOM | 394 | ND2 | ASN | A | 169 | 14.976 | 2.518 | 2.202 | 1.00 | 9.54 |
| ATOM | 395 | C | ASN | A | 169 | 17.940 | 2.752 | 0.095 | 1.00 | 7.21 |
| ATOM | 396 | O | ASN | A | 169 | 17.519 | 3.903 | 0.194 | 1.00 | 7.74 |
| ATOM | 397 | N | ALA | A | 170 | 19.192 | 2.492 | −0.164 | 1.00 | 6.89 |
| ATOM | 398 | CA | ALA | A | 170 | 20.094 | 3.618 | −0.395 | 1.00 | 8.20 |
| ATOM | 399 | CB | ALA | A | 170 | 21.530 | 3.198 | −0.592 | 1.00 | 9.33 |
| ATOM | 400 | C | ALA | A | 170 | 19.713 | 4.518 | −1.538 | 1.00 | 8.07 |
| ATOM | 401 | O | ALA | A | 170 | 20.153 | 5.646 | −1.671 | 1.00 | 9.94 |
| ATOM | 402 | N | ASN | A | 171 | 18.914 | 3.932 | −2.526 | 1.00 | 6.67 |
| ATOM | 403 | CA | ASN | A | 171 | 18.440 | 4.703 | −3.667 | 1.00 | 6.60 |
| ATOM | 404 | CB | ASN | A | 171 | 18.581 | 3.863 | −4.942 | 1.00 | 6.96 |
| ATOM | 405 | CG | ASN | A | 171 | 19.974 | 3.734 | −5.420 | 1.00 | 8.99 |
| ATOM | 406 | OD1 | ASN | A | 171 | 20.875 | 4.433 | −4.889 | 1.00 | 10.77 |
| ATOM | 407 | ND2 | ASN | A | 171 | 20.206 | 2.852 | −6.354 | 1.00 | 9.61 |
| ATOM | 408 | C | ASN | A | 171 | 17.060 | 5.200 | −3.518 | 1.00 | 6.97 |
| ATOM | 409 | O | ASN | A | 171 | 16.472 | 5.735 | −4.503 | 1.00 | 7.86 |
| ATOM | 410 | N | ILE | A | 172 | 16.454 | 5.153 | −2.355 | 1.00 | 6.72 |
| ATOM | 411 | CA | ILE | A | 172 | 15.100 | 5.676 | −2.059 | 1.00 | 7.31 |
| ATOM | 412 | CB | ILE | A | 172 | 14.353 | 4.688 | −1.150 | 1.00 | 7.92 |
| ATOM | 413 | CG1 | ILE | A | 172 | 14.097 | 3.383 | −1.802 | 1.00 | 8.61 |
| ATOM | 414 | CD1 | ILE | A | 172 | 13.079 | 3.404 | −2.877 | 1.00 | 12.01 |
| ATOM | 415 | CG2 | ILE | A | 172 | 13.083 | 5.316 | −0.552 | 1.00 | 9.61 |
| ATOM | 416 | C | ILE | A | 172 | 15.181 | 7.056 | −1.448 | 1.00 | 8.27 |
| ATOM | 417 | O | ILE | A | 172 | 15.975 | 7.253 | −0.495 | 1.00 | 11.02 |
| ATOM | 418 | N | LEU | A | 173 | 14.429 | 7.979 | −1.935 | 1.00 | 7.10 |
| ATOM | 419 | CA | LEU | A | 173 | 14.229 | 9.322 | −1.412 | 1.00 | 7.53 |
| ATOM | 420 | CB | LEU | A | 173 | 14.191 | 10.326 | −2.555 | 1.00 | 8.24 |
| ATOM | 421 | CG | LEU | A | 173 | 15.519 | 10.597 | −3.225 | 1.00 | 9.19 |
| ATOM | 422 | CD1 | LEU | A | 173 | 15.282 | 11.380 | −4.501 | 1.00 | 10.78 |
| ATOM | 423 | CD2 | LEU | A | 173 | 16.407 | 11.388 | −2.226 | 1.00 | 11.16 |
| ATOM | 424 | C | LEU | A | 173 | 12.932 | 9.370 | −0.651 | 1.00 | 7.76 |
| ATOM | 425 | O | LEU | A | 173 | 12.056 | 8.522 | −0.801 | 1.00 | 7.69 |
| ATOM | 426 | N | PRO | A | 174 | 12.694 | 10.390 | 0.186 | 1.00 | 7.85 |
| ATOM | 427 | CA | PRO | A | 174 | 11.417 | 10.584 | 0.764 | 1.00 | 7.82 |
| ATOM | 428 | CB | PRO | A | 174 | 11.532 | 11.980 | 1.473 | 1.00 | 9.30 |
| ATOM | 429 | CG | PRO | A | 174 | 12.984 | 12.061 | 1.802 | 1.00 | 10.51 |
| ATOM | 430 | CD | PRO | A | 174 | 13.661 | 11.416 | 0.611 | 1.00 | 8.84 |
| ATOM | 431 | C | PRO | A | 174 | 10.333 | 10.696 | −0.307 | 1.00 | 7.30 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 432 | O | PRO | A | 174 | 10.553 | 11.260 | −1.381 | 1.00 | 7.76 |
| ATOM | 433 | N | GLY | A | 175 | 9.154 | 10.200 | 0.001 | 1.00 | 6.79 |
| ATOM | 434 | CA | GLY | A | 175 | 7.996 | 10.210 | −0.914 | 1.00 | 6.26 |
| ATOM | 435 | C | GLY | A | 175 | 6.765 | 10.639 | −0.273 | 1.00 | 5.54 |
| ATOM | 436 | O | GLY | A | 175 | 6.762 | 11.489 | 0.638 | 1.00 | 7.38 |
| ATOM | 437 | N | TYR | A | 176 | 5.644 | 10.116 | −0.721 | 1.00 | 5.71 |
| ATOM | 438 | CA | TYR | A | 176 | 4.359 | 10.473 | −0.119 | 1.00 | 5.79 |
| ATOM | 439 | CB | TYR | A | 176 | 3.806 | 11.798 | −0.712 | 1.00 | 6.83 |
| ATOM | 440 | CG | TYR | A | 176 | 3.016 | 12.598 | 0.351 | 1.00 | 7.97 |
| ATOM | 441 | CD1 | TYR | A | 176 | 3.687 | 13.341 | 1.283 | 1.00 | 8.82 |
| ATOM | 442 | CE1 | TYR | A | 176 | 3.066 | 13.964 | 2.339 | 1.00 | 10.20 |
| ATOM | 443 | CZ | TYR | A | 176 | 1.819 | 13.810 | 2.453 | 1.00 | 10.76 |
| ATOM | 444 | OH | TYR | A | 176 | 1.202 | 14.472 | 3.554 | 1.00 | 18.66 |
| ATOM | 445 | CE2 | TYR | A | 176 | 1.005 | 13.174 | 1.617 | 1.00 | 10.48 |
| ATOM | 446 | CD2 | TYR | A | 176 | 1.627 | 12.474 | 0.495 | 1.00 | 9.61 |
| ATOM | 447 | C | TYR | A | 176 | 3.338 | 9.404 | −0.355 | 1.00 | 5.80 |
| ATOM | 448 | O | TYR | A | 176 | 3.436 | 8.664 | −1.367 | 1.00 | 6.30 |
| ATOM | 449 | N | ASP | A | 177 | 2.389 | 9.249 | 0.547 | 1.00 | 5.45 |
| ATOM | 450 | CA | ASP | A | 177 | 1.336 | 8.285 | 0.504 | 1.00 | 5.69 |
| ATOM | 451 | CB | ASP | A | 177 | 1.344 | 7.460 | 1.813 | 1.00 | 5.95 |
| ATOM | 452 | CG | ASP | A | 177 | 0.375 | 6.348 | 1.824 | 1.00 | 5.42 |
| ATOM | 453 | OD1 | ASP | A | 177 | −0.630 | 6.289 | 1.123 | 1.00 | 6.78 |
| ATOM | 454 | OD2 | ASP | A | 177 | 0.612 | 5.414 | 2.691 | 1.00 | 6.08 |
| ATOM | 455 | C | ASP | A | 177 | 0.048 | 8.992 | 0.265 | 1.00 | 6.83 |
| ATOM | 456 | O | ASP | A | 177 | −0.480 | 9.725 | 1.129 | 1.00 | 6.64 |
| ATOM | 457 | N | MET | A | 178 | −0.490 | 8.846 | −0.959 | 1.00 | 6.59 |
| ATOM | 458 | CA | MET | A | 178 | −1.678 | 9.512 | −1.408 | 1.00 | 7.10 |
| ATOM | 459 | CB | MET | A | 178 | −1.605 | 9.706 | −2.908 | 1.00 | 8.66 |
| ATOM | 460 | CG | MET | A | 178 | −0.513 | 10.596 | −3.376 | 1.00 | 12.57 |
| ATOM | 461 | SD | MET | A | 178 | −0.880 | 12.356 | −2.735 | 1.00 | 14.68 |
| ATOM | 462 | CE | MET | A | 178 | 0.703 | 13.091 | −3.292 | 1.00 | 16.71 |
| ATOM | 463 | C | MET | A | 178 | −2.923 | 8.804 | −1.129 | 1.00 | 7.38 |
| ATOM | 464 | O | MET | A | 178 | −4.036 | 9.257 | −1.524 | 1.00 | 7.66 |
| ATOM | 465 | N | ILE | A | 179 | −2.905 | 7.638 | −0.488 | 1.00 | 6.89 |
| ATOM | 466 | CA | ILE | A | 179 | −4.128 | 6.845 | −0.312 | 1.00 | 6.94 |
| ATOM | 467 | CB | ILE | A | 179 | −3.868 | 5.388 | 0.004 | 1.00 | 6.92 |
| ATOM | 468 | CG1 | ILE | A | 179 | −3.000 | 4.760 | −1.050 | 1.00 | 7.39 |
| ATOM | 469 | CD1 | ILE | A | 179 | −2.557 | 3.390 | −0.662 | 1.00 | 7.15 |
| ATOM | 470 | CG2 | ILE | A | 179 | −5.221 | 4.677 | 0.138 | 1.00 | 6.97 |
| ATOM | 471 | C | ILE | A | 179 | −5.058 | 7.480 | 0.768 | 1.00 | 8.71 |
| ATOM | 472 | O | ILE | A | 179 | −4.673 | 7.648 | 1.923 | 1.00 | 8.31 |
| ATOM | 473 | N | SER | A | 180 | −6.237 | 7.910 | 0.285 | 1.00 | 8.81 |
| ATOM | 474 | CA | SER | A | 180 | −7.198 | 8.630 | 1.181 | 1.00 | 10.10 |
| ATOM | 475 | CB | SER | A | 180 | −8.028 | 9.621 | 0.281 | 1.00 | 12.44 |
| ATOM | 476 | OG | SER | A | 180 | −7.273 | 10.522 | −0.445 | 1.00 | 15.19 |
| ATOM | 477 | C | SER | A | 180 | −8.111 | 7.675 | 1.930 | 1.00 | 11.84 |
| ATOM | 478 | O | SER | A | 180 | −8.470 | 7.985 | 3.113 | 1.00 | 15.18 |
| ATOM | 479 | N | ASN | A | 181 | −8.479 | 6.536 | 1.365 | 1.00 | 10.16 |
| ATOM | 480 | CA | ASN | A | 181 | −9.420 | 5.595 | 2.008 | 1.00 | 10.79 |
| ATOM | 481 | CB | ASN | A | 181 | −10.070 | 4.827 | 0.890 | 1.00 | 13.53 |
| ATOM | 482 | CG | ASN | A | 181 | −11.030 | 3.766 | 1.345 | 1.00 | 17.13 |
| ATOM | 483 | OD1 | ASN | A | 181 | −12.160 | 3.727 | 0.835 | 1.00 | 27.54 |
| ATOM | 484 | ND2 | ASN | A | 181 | −10.644 | 2.874 | 2.148 | 1.00 | 15.26 |
| ATOM | 485 | C | ASN | A | 181 | −8.698 | 4.766 | 3.032 | 1.00 | 12.42 |
| ATOM | 486 | O | ASN | A | 181 | −7.657 | 4.115 | 2.672 | 1.00 | 10.80 |
| ATOM | 487 | N | LEU | A | 182 | −9.080 | 4.817 | 4.282 | 1.00 | 12.94 |
| ATOM | 488 | CA | LEU | A | 182 | −8.359 | 4.163 | 5.341 | 1.00 | 13.82 |
| ATOM | 489 | CB | LEU | A | 182 | −9.001 | 4.520 | 6.725 | 1.00 | 17.63 |
| ATOM | 490 | CG | LEU | A | 182 | −8.244 | 5.772 | 7.282 | 1.00 | 21.27 |
| ATOM | 491 | CD1 | LEU | A | 182 | −8.515 | 7.063 | 6.546 | 1.00 | 22.77 |
| ATOM | 492 | CD2 | LEU | A | 182 | −8.530 | 6.004 | 8.771 | 1.00 | 25.97 |
| ATOM | 493 | C | LEU | A | 182 | −8.309 | 2.666 | 5.160 | 1.00 | 12.47 |
| ATOM | 494 | O | LEU | A | 182 | −7.285 | 2.066 | 5.509 | 1.00 | 11.86 |
| ATOM | 495 | N | SER | A | 183 | −9.370 | 2.062 | 4.649 | 1.00 | 13.51 |
| ATOM | 496 | CA | SER | A | 183 | −9.408 | 0.626 | 4.481 | 1.00 | 14.42 |
| ATOM | 497 | CB | SER | A | 183 | −10.801 | 0.147 | 4.016 | 1.00 | 18.23 |
| ATOM | 498 | OG | SER | A | 183 | −11.693 | 0.448 | 5.055 | 1.00 | 27.95 |
| ATOM | 499 | C | SER | A | 183 | −8.358 | 0.210 | 3.421 | 1.00 | 14.48 |
| ATOM | 500 | O | SER | A | 183 | −7.677 | −0.816 | 3.541 | 1.00 | 14.34 |
| ATOM | 501 | N | VAL | A | 184 | −8.254 | 0.962 | 2.340 | 1.00 | 10.65 |
| ATOM | 502 | CA | VAL | A | 184 | −7.299 | 0.682 | 1.274 | 1.00 | 9.80 |
| ATOM | 503 | CB | VAL | A | 184 | −7.563 | 1.548 | 0.050 | 1.00 | 9.12 |
| ATOM | 504 | CG1 | VAL | A | 184 | −6.513 | 1.370 | −0.987 | 1.00 | 9.92 |
| ATOM | 505 | CG2 | VAL | A | 184 | −8.959 | 1.230 | −0.529 | 1.00 | 10.32 |
| ATOM | 506 | C | VAL | A | 184 | −5.892 | 0.959 | 1.838 | 1.00 | 9.37 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 507 | O | VAL | A | 184 | −4.947 | 0.163 | 1.614 | 1.00 | 8.64 |
| ATOM | 508 | N | ALA | A | 185 | −5.717 | 2.035 | 2.560 | 1.00 | 7.74 |
| ATOM | 509 | CA | ALA | A | 185 | −4.409 | 2.496 | 3.014 | 1.00 | 8.40 |
| ATOM | 510 | CB | ALA | A | 185 | −4.518 | 3.782 | 3.769 | 1.00 | 8.61 |
| ATOM | 511 | C | ALA | A | 185 | −3.765 | 1.462 | 3.951 | 1.00 | 7.36 |
| ATOM | 512 | O | ALA | A | 185 | −2.561 | 1.236 | 3.898 | 1.00 | 8.04 |
| ATOM | 513 | N | ASN | A | 186 | −4.512 | 0.866 | 4.888 | 1.00 | 7.38 |
| ATOM | 514 | CA | ASN | A | 186 | −4.053 | −0.202 | 5.727 | 1.00 | 7.56 |
| ATOM | 515 | CB | ASN | A | 186 | −3.698 | −1.446 | 4.911 | 1.00 | 8.71 |
| ATOM | 516 | CG | ASN | A | 186 | −3.419 | −2.663 | 5.748 | 1.00 | 9.43 |
| ATOM | 517 | OD1 | ASN | A | 186 | −4.042 | −2.869 | 6.806 | 1.00 | 11.20 |
| ATOM | 518 | ND2 | ASN | A | 186 | −2.466 | −3.475 | 5.363 | 1.00 | 9.33 |
| ATOM | 519 | C | ASN | A | 186 | −2.870 | 0.273 | 6.514 | 1.00 | 7.70 |
| ATOM | 520 | O | ASN | A | 186 | −1.983 | −0.556 | 6.813 | 1.00 | 8.52 |
| ATOM | 521 | N | ASP | A | 187 | −2.829 | 1.517 | 6.960 | 1.00 | 7.97 |
| ATOM | 522 | CA | ASP | A | 187 | −1.704 | 2.049 | 7.738 | 1.00 | 8.33 |
| ATOM | 523 | CB | ASP | A | 187 | −0.717 | 2.777 | 6.809 | 1.00 | 7.56 |
| ATOM | 524 | CG | ASP | A | 187 | −1.272 | 4.015 | 6.197 | 1.00 | 8.27 |
| ATOM | 525 | OD1 | ASP | A | 187 | −2.468 | 4.348 | 6.451 | 1.00 | 7.87 |
| ATOM | 526 | OD2 | ASP | A | 187 | −0.487 | 4.741 | 5.479 | 1.00 | 7.37 |
| ATOM | 527 | C | ASP | A | 187 | −2.160 | 2.986 | 8.860 | 1.00 | 8.94 |
| ATOM | 528 | O | ASP | A | 187 | −1.344 | 3.636 | 9.461 | 1.00 | 11.36 |
| ATOM | 529 | N | GLY | A | 188 | −3.443 | 3.017 | 9.114 | 1.00 | 10.87 |
| ATOM | 530 | CA | GLY | A | 188 | −3.977 | 3.736 | 10.284 | 1.00 | 12.33 |
| ATOM | 531 | C | GLY | A | 188 | −4.503 | 5.108 | 9.968 | 1.00 | 13.89 |
| ATOM | 532 | O | GLY | A | 188 | −5.087 | 5.774 | 10.892 | 1.00 | 15.82 |
| ATOM | 533 | N | GLY | A | 189 | −4.443 | 5.647 | 8.757 | 1.00 | 10.60 |
| ATOM | 534 | CA | GLY | A | 189 | −4.950 | 6.944 | 8.448 | 1.00 | 11.77 |
| ATOM | 535 | C | GLY | A | 189 | −4.862 | 7.217 | 6.985 | 1.00 | 9.51 |
| ATOM | 536 | O | GLY | A | 189 | −4.467 | 6.390 | 6.148 | 1.00 | 8.77 |
| ATOM | 537 | N | GLY | A | 190 | −5.336 | 8.378 | 6.634 | 1.00 | 9.97 |
| ATOM | 538 | CA | GLY | A | 190 | −5.334 | 8.901 | 5.280 | 1.00 | 9.16 |
| ATOM | 539 | C | GLY | A | 190 | −4.024 | 9.320 | 4.775 | 1.00 | 8.98 |
| ATOM | 540 | O | GLY | A | 190 | −2.971 | 8.745 | 5.127 | 1.00 | 8.01 |
| ATOM | 541 | N | ARG | A | 191 | −3.972 | 10.327 | 3.952 | 1.00 | 7.94 |
| ATOM | 542 | CA | ARG | A | 191 | −2.731 | 10.738 | 3.314 | 1.00 | 8.02 |
| ATOM | 543 | CB | ARG | A | 191 | −2.963 | 11.871 | 2.266 | 1.00 | 8.51 |
| ATOM | 544 | CG | ARG | A | 191 | −3.877 | 11.432 | 1.136 | 1.00 | 7.74 |
| ATOM | 545 | CD | ARG | A | 191 | −3.902 | 12.559 | 0.083 | 1.00 | 8.51 |
| ATOM | 546 | NE | ARG | A | 191 | −4.599 | 12.102 | −1.104 | 1.00 | 8.28 |
| ATOM | 547 | CZ | ARG | A | 191 | −4.911 | 12.871 | −2.147 | 1.00 | 8.35 |
| ATOM | 548 | NH1 | ARG | A | 191 | −4.629 | 14.149 | −2.127 | 1.00 | 9.98 |
| ATOM | 549 | NH2 | ARG | A | 191 | −5.409 | 12.285 | −3.169 | 1.00 | 9.09 |
| ATOM | 550 | C | ARG | A | 191 | −1.657 | 11.008 | 4.308 | 1.00 | 8.04 |
| ATOM | 551 | O | ARG | A | 191 | −1.896 | 11.619 | 5.349 | 1.00 | 9.64 |
| ATOM | 552 | N | ASP | A | 192 | −0.430 | 10.636 | 4.004 | 1.00 | 7.25 |
| ATOM | 553 | CA | ASP | A | 192 | 0.640 | 10.768 | 4.962 | 1.00 | 6.35 |
| ATOM | 554 | CB | ASP | A | 192 | 0.574 | 9.701 | 6.044 | 1.00 | 6.88 |
| ATOM | 555 | CG | ASP | A | 192 | 0.876 | 8.291 | 5.513 | 1.00 | 6.77 |
| ATOM | 556 | OD1 | ASP | A | 192 | 2.096 | 7.958 | 5.536 | 1.00 | 8.59 |
| ATOM | 557 | OD2 | ASP | A | 192 | −0.003 | 7.556 | 5.101 | 1.00 | 6.72 |
| ATOM | 558 | C | ASP | A | 192 | 1.979 | 10.728 | 4.306 | 1.00 | 7.55 |
| ATOM | 559 | O | ASP | A | 192 | 2.092 | 10.273 | 3.133 | 1.00 | 7.78 |
| ATOM | 560 | N | SER | A | 193 | 3.053 | 11.101 | 4.960 | 1.00 | 6.92 |
| ATOM | 561 | CA | SER | A | 193 | 4.348 | 11.212 | 4.348 | 1.00 | 7.50 |
| ATOM | 562 | CB | SER | A | 193 | 5.240 | 12.283 | 4.984 | 1.00 | 9.40 |
| ATOM | 563 | OG | SER | A | 193 | 5.563 | 11.849 | 6.268 | 1.00 | 13.98 |
| ATOM | 564 | C | SER | A | 193 | 5.146 | 9.884 | 4.222 | 1.00 | 8.09 |
| ATOM | 565 | O | SER | A | 193 | 6.210 | 9.953 | 3.632 | 1.00 | 10.63 |
| ATOM | 566 | N | ASP | A | 194 | 4.610 | 8.792 | 4.779 | 1.00 | 6.40 |
| ATOM | 567 | CA | ASP | A | 194 | 5.391 | 7.522 | 4.747 | 1.00 | 6.88 |
| ATOM | 568 | CB | ASP | A | 194 | 5.285 | 6.892 | 6.135 | 1.00 | 7.25 |
| ATOM | 569 | CG | ASP | A | 194 | 6.120 | 5.683 | 6.255 | 1.00 | 10.11 |
| ATOM | 570 | OD1 | ASP | A | 194 | 6.667 | 5.164 | 5.277 | 1.00 | 8.47 |
| ATOM | 571 | OD2 | ASP | A | 194 | 6.331 | 5.187 | 7.397 | 1.00 | 10.52 |
| ATOM | 572 | C | ASP | A | 194 | 4.790 | 6.635 | 3.662 | 1.00 | 6.07 |
| ATOM | 573 | O | ASP | A | 194 | 3.717 | 6.058 | 3.799 | 1.00 | 6.06 |
| ATOM | 574 | N | ALA | A | 195 | 5.547 | 6.457 | 2.575 | 1.00 | 5.69 |
| ATOM | 575 | CA | ALA | A | 195 | 5.146 | 5.690 | 1.413 | 1.00 | 5.95 |
| ATOM | 576 | CB | ALA | A | 195 | 5.736 | 6.331 | 0.154 | 1.00 | 6.97 |
| ATOM | 577 | C | ALA | A | 195 | 5.528 | 4.270 | 1.505 | 1.00 | 5.77 |
| ATOM | 578 | O | ALA | A | 195 | 5.492 | 3.503 | 0.525 | 1.00 | 6.21 |
| ATOM | 579 | N | ARG | A | 196 | 5.943 | 3.757 | 2.686 | 1.00 | 5.76 |
| ATOM | 580 | CA | ARG | A | 196 | 6.167 | 2.338 | 2.814 | 1.00 | 5.39 |
| ATOM | 581 | CB | ARG | A | 196 | 6.839 | 2.012 | 4.156 | 1.00 | 5.31 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 582 | CG | ARG | A | 196 | 8.262 | 2.402 | 4.193 | 1.00 | 5.59 |
| ATOM | 583 | CD | ARG | A | 196 | 8.965 | 2.196 | 5.509 | 1.00 | 6.11 |
| ATOM | 584 | NE | ARG | A | 196 | 10.318 | 2.671 | 5.486 | 1.00 | 5.99 |
| ATOM | 585 | CZ | ARG | A | 196 | 11.291 | 2.307 | 6.362 | 1.00 | 6.28 |
| ATOM | 586 | NH1 | ARG | A | 196 | 11.064 | 1.394 | 7.261 | 1.00 | 6.70 |
| ATOM | 587 | NH2 | ARG | A | 196 | 12.480 | 2.848 | 6.217 | 1.00 | 6.61 |
| ATOM | 588 | C | ARG | A | 196 | 4.923 | 1.534 | 2.624 | 1.00 | 5.46 |
| ATOM | 589 | O | ARG | A | 196 | 3.805 | 1.989 | 2.885 | 1.00 | 6.75 |
| ATOM | 590 | N | ASP | A | 197 | 5.087 | 0.312 | 2.118 | 1.00 | 5.18 |
| ATOM | 591 | CA | ASP | A | 197 | 4.000 | −0.590 | 1.838 | 1.00 | 5.46 |
| ATOM | 592 | CB | ASP | A | 197 | 4.408 | −1.513 | 0.700 | 1.00 | 5.77 |
| ATOM | 593 | CG | ASP | A | 197 | 3.339 | −2.365 | 0.133 | 1.00 | 5.07 |
| ATOM | 594 | OD1 | ASP | A | 197 | 2.233 | −2.457 | 0.741 | 1.00 | 5.88 |
| ATOM | 595 | OD2 | ASP | A | 197 | 3.582 | −3.024 | −0.908 | 1.00 | 6.33 |
| ATOM | 596 | C | ASP | A | 197 | 3.705 | −1.415 | 3.064 | 1.00 | 5.80 |
| ATOM | 597 | O | ASP | A | 197 | 4.553 | −2.239 | 3.480 | 1.00 | 6.13 |
| ATOM | 598 | N | PRO | A | 198 | 2.518 | −1.280 | 3.680 | 1.00 | 5.31 |
| ATOM | 599 | CA | PRO | A | 198 | 2.163 | −2.136 | 4.851 | 1.00 | 5.77 |
| ATOM | 600 | CB | PRO | A | 198 | 1.021 | −1.371 | 5.461 | 1.00 | 6.08 |
| ATOM | 601 | CG | PRO | A | 198 | 0.279 | −0.730 | 4.269 | 1.00 | 6.18 |
| ATOM | 602 | CD | PRO | A | 198 | 1.414 | −0.399 | 3.318 | 1.00 | 5.79 |
| ATOM | 603 | C | PRO | A | 198 | 1.790 | −3.489 | 4.470 | 1.00 | 6.13 |
| ATOM | 604 | O | PRO | A | 198 | 1.582 | −4.338 | 5.376 | 1.00 | 7.38 |
| ATOM | 605 | N | GLY | A | 199 | 1.609 | −3.797 | 3.209 | 1.00 | 6.60 |
| ATOM | 606 | CA | GLY | A | 199 | 1.085 | −4.986 | 2.654 | 1.00 | 7.51 |
| ATOM | 607 | C | GLY | A | 199 | −0.337 | −4.863 | 2.155 | 1.00 | 7.67 |
| ATOM | 608 | O | GLY | A | 199 | −1.180 | −4.373 | 2.888 | 1.00 | 10.17 |
| ATOM | 609 | N | ASP | A | 200 | −0.567 | −5.331 | 0.955 | 1.00 | 6.97 |
| ATOM | 610 | CA | ASP | A | 200 | −1.900 | −5.225 | 0.292 | 1.00 | 7.36 |
| ATOM | 611 | CB | ASP | A | 200 | −1.784 | −4.531 | −1.074 | 1.00 | 7.25 |
| ATOM | 612 | CG | ASP | A | 200 | −1.028 | −5.342 | −2.048 | 1.00 | 8.64 |
| ATOM | 613 | OD1 | ASP | A | 200 | −0.670 | −6.493 | −1.749 | 1.00 | 9.82 |
| ATOM | 614 | OD2 | ASP | A | 200 | −0.707 | −4.901 | −3.160 | 1.00 | 9.41 |
| ATOM | 615 | C | ASP | A | 200 | −2.657 | −6.522 | 0.241 | 1.00 | 7.77 |
| ATOM | 616 | O | ASP | A | 200 | −3.644 | −6.653 | −0.499 | 1.00 | 8.52 |
| ATOM | 617 | N | ALA | A | 201 | −2.262 | −7.494 | 1.053 | 1.00 | 6.72 |
| ATOM | 618 | CA | ALA | A | 201 | −3.000 | −8.739 | 1.185 | 1.00 | 6.99 |
| ATOM | 619 | CB | ALA | A | 201 | −2.428 | −9.661 | 2.301 | 1.00 | 6.57 |
| ATOM | 620 | C | ALA | A | 201 | −4.438 | −8.465 | 1.529 | 1.00 | 7.55 |
| ATOM | 621 | O | ALA | A | 201 | −4.767 | −7.591 | 2.280 | 1.00 | 8.42 |
| ATOM | 622 | N | VAL | A | 202 | −5.295 | −9.319 | 0.903 | 1.00 | 8.04 |
| ATOM | 623 | CA | VAL | A | 202 | −6.745 | −9.245 | 1.124 | 1.00 | 9.48 |
| ATOM | 624 | CB | VAL | A | 202 | −7.487 | −8.565 | −0.054 | 1.00 | 10.37 |
| ATOM | 625 | CG1 | VAL | A | 202 | −7.252 | −7.081 | −0.044 | 1.00 | 10.28 |
| ATOM | 626 | CG2 | VAL | A | 202 | −7.166 | −9.182 | −1.337 | 1.00 | 11.04 |
| ATOM | 627 | C | VAL | A | 202 | −7.286 | −10.665 | 1.405 | 1.00 | 10.19 |
| ATOM | 628 | O | VAL | A | 202 | −6.903 | −11.630 | 0.831 | 1.00 | 10.72 |
| ATOM | 629 | N | ALA | A | 203 | −8.337 | −10.618 | 2.201 | 1.00 | 11.68 |
| ATOM | 630 | CA | ALA | A | 203 | −9.123 | −11.870 | 2.504 | 1.00 | 13.91 |
| ATOM | 631 | CB | ALA | A | 203 | −9.788 | −11.667 | 3.795 | 1.00 | 14.90 |
| ATOM | 632 | C | ALA | A | 203 | −10.113 | −12.092 | 1.404 | 1.00 | 15.33 |
| ATOM | 633 | O | ALA | A | 203 | −10.431 | −11.146 | 0.645 | 1.00 | 14.65 |
| ATOM | 634 | N | ALA | A | 204 | −10.636 | −13.337 | 1.318 | 1.00 | 17.00 |
| ATOM | 635 | CA | ALA | A | 204 | −11.659 | −13.634 | 0.314 | 1.00 | 18.07 |
| ATOM | 636 | CB | ALA | A | 204 | −12.202 | −15.055 | 0.542 | 1.00 | 19.01 |
| ATOM | 637 | C | ALA | A | 204 | −12.852 | −12.673 | 0.458 | 1.00 | 17.51 |
| ATOM | 638 | O | ALA | A | 204 | −13.241 | −12.292 | 1.578 | 1.00 | 16.85 |
| ATOM | 639 | N | ASN | A | 205 | −13.256 | −12.133 | −0.672 | 1.00 | 17.92 |
| ATOM | 640 | CA | ASN | A | 205 | −14.397 | −11.176 | −0.702 | 1.00 | 18.82 |
| ATOM | 641 | CB | ASN | A | 205 | −15.666 | −11.822 | −0.062 | 1.00 | 19.75 |
| ATOM | 642 | CG | ASN | A | 205 | −16.040 | −13.085 | −0.737 | 1.00 | 24.23 |
| ATOM | 643 | OD1 | ASN | A | 205 | −16.045 | −13.123 | −1.928 | 1.00 | 21.45 |
| ATOM | 644 | ND2 | ASN | A | 205 | −16.239 | −14.161 | 0.021 | 1.00 | 27.35 |
| ATOM | 645 | C | ASN | A | 205 | −14.207 | −9.833 | −0.064 | 1.00 | 19.17 |
| ATOM | 646 | O | ASN | A | 205 | −15.084 | −8.968 | −0.061 | 1.00 | 19.44 |
| ATOM | 647 | N | GLU | A | 206 | −12.964 | −9.512 | 0.331 | 1.00 | 14.83 |
| ATOM | 648 | CA | GLU | A | 206 | −12.724 | −8.217 | 0.903 | 1.00 | 16.36 |
| ATOM | 649 | CB | GLU | A | 206 | −11.320 | −8.148 | 1.583 | 1.00 | 17.79 |
| ATOM | 650 | CG | GLU | A | 206 | −11.096 | −6.977 | 2.445 | 1.00 | 19.23 |
| ATOM | 651 | CD | GLU | A | 206 | −9.922 | −7.194 | 3.442 | 1.00 | 19.08 |
| ATOM | 652 | OE1 | GLU | A | 206 | −9.146 | −8.178 | 3.344 | 1.00 | 17.16 |
| ATOM | 653 | OE2 | GLU | A | 206 | −9.844 | −6.347 | 4.381 | 1.00 | 21.73 |
| ATOM | 654 | C | GLU | A | 206 | −12.902 | −7.125 | −0.125 | 1.00 | 15.26 |
| ATOM | 655 | O | GLU | A | 206 | −13.222 | −5.958 | 0.248 | 1.00 | 19.72 |
| ATOM | 656 | N | CYS | A | 207 | −12.633 | −7.385 | −1.359 | 1.00 | 14.23 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 657 | CA | CYS | A | 207 | −12.683 | −6.387 | −2.452 | 1.00 | 16.42 |
| ATOM | 658 | CB | CYS | A | 207 | −11.485 | −6.583 | −3.314 | 1.00 | 14.78 |
| ATOM | 659 | SG | CYS | A | 207 | −9.906 | −6.463 | −2.453 | 1.00 | 14.96 |
| ATOM | 660 | C | CYS | A | 207 | −13.972 | −6.570 | −3.315 | 1.00 | 21.52 |
| ATOM | 661 | O | CYS | A | 207 | −14.048 | −6.068 | −4.447 | 1.00 | 23.46 |
| ATOM | 662 | N | GLY | A | 208 | −14.827 | −7.409 | −2.785 | 1.00 | 20.98 |
| ATOM | 663 | CA | GLY | A | 208 | −16.064 | −7.795 | −3.503 | 1.00 | 23.51 |
| ATOM | 664 | C | GLY | A | 208 | −16.257 | −9.282 | −3.548 | 1.00 | 19.51 |
| ATOM | 665 | O | GLY | A | 208 | −16.884 | −9.794 | −2.668 | 1.00 | 23.61 |
| ATOM | 666 | N | THR | A | 209 | −15.779 | −9.922 | −4.613 | 1.00 | 20.09 |
| ATOM | 667 | CA | THR | A | 209 | −15.871 | −11.408 | −4.777 | 1.00 | 19.12 |
| ATOM | 668 | CB | THR | A | 209 | −16.798 | −11.765 | −5.955 | 1.00 | 24.34 |
| ATOM | 669 | OG1 | THR | A | 209 | −16.213 | −11.246 | −7.137 | 1.00 | 30.57 |
| ATOM | 670 | CG2 | THR | A | 209 | −18.218 | −11.124 | −5.747 | 1.00 | 25.63 |
| ATOM | 671 | C | THR | A | 209 | −14.552 | −12.122 | −4.996 | 1.00 | 23.27 |
| ATOM | 672 | O | THR | A | 209 | −14.493 | −13.270 | −5.387 | 1.00 | 22.39 |
| ATOM | 673 | N | ASN | A | 210 | −13.479 | −11.425 | −4.709 | 1.00 | 20.50 |
| ATOM | 674 | CA | ASN | A | 210 | −12.114 | −12.007 | −4.882 | 1.00 | 17.96 |
| ATOM | 675 | CB | ASN | A | 210 | −11.111 | −10.875 | −4.568 | 1.00 | 17.15 |
| ATOM | 676 | CG | ASN | A | 210 | −11.211 | −10.379 | −3.163 | 1.00 | 16.88 |
| ATOM | 677 | OD1 | ASN | A | 210 | −12.138 | −9.682 | −2.754 | 1.00 | 17.67 |
| ATOM | 678 | ND2 | ASN | A | 210 | −10.232 | −10.704 | −2.312 | 1.00 | 13.84 |
| ATOM | 679 | C | ASN | A | 210 | −11.820 | −13.197 | −3.975 | 1.00 | 14.40 |
| ATOM | 680 | O | ASN | A | 210 | −12.290 | −13.338 | −2.911 | 1.00 | 15.29 |
| ATOM | 681 | N | GLY | A | 211 | −10.912 | −14.015 | −4.490 | 1.00 | 15.74 |
| ATOM | 682 | CA | GLY | A | 211 | −10.299 | −14.941 | −3.541 | 1.00 | 15.89 |
| ATOM | 683 | C | GLY | A | 211 | −9.224 | −14.257 | −2.694 | 1.00 | 14.31 |
| ATOM | 684 | O | GLY | A | 211 | −8.755 | −13.134 | −3.020 | 1.00 | 14.67 |
| ATOM | 685 | N | ALA | A | 212 | −8.816 | −14.955 | −1.685 | 1.00 | 15.00 |
| ATOM | 686 | CA | ALA | A | 212 | −7.728 | −14.439 | −0.816 | 1.00 | 13.95 |
| ATOM | 687 | CB | ALA | A | 212 | −7.520 | −15.357 | 0.424 | 1.00 | 15.40 |
| ATOM | 688 | C | ALA | A | 212 | −6.458 | −14.293 | −1.643 | 1.00 | 13.20 |
| ATOM | 689 | O | ALA | A | 212 | −6.124 | −15.003 | −2.532 | 1.00 | 14.94 |
| ATOM | 690 | N | GLN | A | 213 | −5.735 | −13.194 | −1.352 | 1.00 | 11.58 |
| ATOM | 691 | CA | GLN | A | 213 | −4.457 | −12.917 | −2.032 | 1.00 | 11.58 |
| ATOM | 692 | CB | GLN | A | 213 | −4.595 | −11.746 | −3.048 | 1.00 | 13.40 |
| ATOM | 693 | CG | GLN | A | 213 | −5.640 | −12.012 | −4.165 | 1.00 | 19.00 |
| ATOM | 694 | CD | GLN | A | 213 | −6.120 | −10.737 | −4.871 | 1.00 | 28.51 |
| ATOM | 695 | OE1 | GLN | A | 213 | −7.232 | −10.715 | −5.495 | 1.00 | 35.94 |
| ATOM | 696 | NE2 | GLN | A | 213 | −5.326 | −9.665 | −4.774 | 1.00 | 31.68 |
| ATOM | 697 | C | GLN | A | 213 | −3.441 | −12.455 | −0.982 | 1.00 | 9.38 |
| ATOM | 698 | O | GLN | A | 213 | −3.725 | −11.654 | −0.142 | 1.00 | 9.82 |
| ATOM | 699 | N | ASN | A | 214 | −2.241 | −12.987 | −1.144 | 1.00 | 9.02 |
| ATOM | 700 | CA | ASN | A | 214 | −1.097 | −12.488 | −0.371 | 1.00 | 8.55 |
| ATOM | 701 | CB | ASN | A | 214 | 0.047 | −13.471 | −0.498 | 1.00 | 10.57 |
| ATOM | 702 | CG | ASN | A | 214 | −0.168 | −14.783 | 0.282 | 1.00 | 13.11 |
| ATOM | 703 | OD1 | ASN | A | 214 | −1.064 | −14.893 | 1.082 | 1.00 | 14.30 |
| ATOM | 704 | ND2 | ASN | A | 214 | 0.800 | −15.668 | 0.170 | 1.00 | 19.85 |
| ATOM | 705 | C | ASN | A | 214 | −0.644 | −11.131 | −0.827 | 1.00 | 8.60 |
| ATOM | 706 | O | ASN | A | 214 | −1.024 | −10.651 | −1.908 | 1.00 | 9.05 |
| ATOM | 707 | N | SER | A | 215 | 0.153 | −10.480 | −0.011 | 1.00 | 7.14 |
| ATOM | 708 | CA | SER | A | 215 | 0.694 | −9.161 | −0.414 | 1.00 | 6.34 |
| ATOM | 709 | CB | SER | A | 215 | 1.466 | −8.613 | 0.781 | 1.00 | 6.38 |
| ATOM | 710 | OG | SER | A | 215 | 0.623 | −8.244 | 1.836 | 1.00 | 6.35 |
| ATOM | 711 | C | SER | A | 215 | 1.546 | −9.291 | −1.627 | 1.00 | 6.25 |
| ATOM | 712 | O | SER | A | 215 | 2.313 | −10.176 | −1.822 | 1.00 | 8.61 |
| ATOM | 713 | N | SER | A | 216 | 1.400 | −8.279 | −2.471 | 1.00 | 6.13 |
| ATOM | 714 | CA | SER | A | 216 | 2.097 | −8.231 | −3.739 | 1.00 | 6.79 |
| ATOM | 715 | CB | SER | A | 216 | 1.371 | −7.282 | −4.750 | 1.00 | 6.97 |
| ATOM | 716 | OG | SER | A | 216 | 1.442 | −5.968 | −4.357 | 1.00 | 7.26 |
| ATOM | 717 | C | SER | A | 216 | 3.543 | −7.770 | −3.669 | 1.00 | 6.04 |
| ATOM | 718 | O | SER | A | 216 | 4.379 | −8.114 | −4.478 | 1.00 | 7.48 |
| ATOM | 719 | N | TRP | A | 217 | 3.808 | −6.888 | −2.701 | 1.00 | 5.46 |
| ATOM | 720 | CA | TRP | A | 217 | 5.102 | −6.148 | −2.674 | 1.00 | 5.91 |
| ATOM | 721 | CB | TRP | A | 217 | 6.241 | −6.987 | −2.081 | 1.00 | 5.66 |
| ATOM | 722 | CG | TRP | A | 217 | 5.823 | −7.650 | −0.842 | 1.00 | 5.49 |
| ATOM | 723 | CD1 | TRP | A | 217 | 5.701 | −9.013 | −0.611 | 1.00 | 6.05 |
| ATOM | 724 | NE1 | TRP | A | 217 | 5.212 | −9.248 | 0.655 | 1.00 | 6.18 |
| ATOM | 725 | CE2 | TRP | A | 217 | 5.004 | −8.053 | 1.291 | 1.00 | 5.67 |
| ATOM | 726 | CD2 | TRP | A | 217 | 5.367 | −7.023 | 0.361 | 1.00 | 5.54 |
| ATOM | 727 | CE3 | TRP | A | 217 | 5.273 | −5.695 | 0.832 | 1.00 | 6.38 |
| ATOM | 728 | CZ3 | TRP | A | 217 | 4.697 | −5.422 | 2.015 | 1.00 | 6.55 |
| ATOM | 729 | CH2 | TRP | A | 217 | 4.307 | −6.472 | 2.894 | 1.00 | 6.64 |
| ATOM | 730 | CZ2 | TRP | A | 217 | 4.459 | −7.750 | 2.537 | 1.00 | 6.04 |
| ATOM | 731 | C | TRP | A | 217 | 5.460 | −5.597 | −4.032 | 1.00 | 5.23 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 732 | O | TRP | A | 217 | 6.610 | −5.453 | −4.397 | 1.00 | 5.68 |
| ATOM | 733 | N | HIS | A | 218 | 4.391 | −5.150 | −4.783 | 1.00 | 5.88 |
| ATOM | 734 | CA | HIS | A | 218 | 4.590 | −4.827 | −6.170 | 1.00 | 5.91 |
| ATOM | 735 | CB | HIS | A | 218 | 3.157 | −4.608 | −6.769 | 1.00 | 6.76 |
| ATOM | 736 | CG | HIS | A | 218 | 3.130 | −4.410 | −8.217 | 1.00 | 6.64 |
| ATOM | 737 | ND1 | HIS | A | 218 | 3.128 | −3.185 | −8.796 | 1.00 | 8.19 |
| ATOM | 738 | CE1 | HIS | A | 218 | 2.891 | −3.302 | −10.068 | 1.00 | 8.67 |
| ATOM | 739 | NE2 | HIS | A | 218 | 2.770 | −4.530 | −10.362 | 1.00 | 10.03 |
| ATOM | 740 | CD2 | HIS | A | 218 | 2.906 | −5.295 | −9.229 | 1.00 | 8.13 |
| ATOM | 741 | C | HIS | A | 218 | 5.521 | −3.631 | −6.340 | 1.00 | 4.77 |
| ATOM | 742 | O | HIS | A | 218 | 6.390 | −3.636 | −7.225 | 1.00 | 4.97 |
| ATOM | 743 | N | GLY | A | 219 | 5.312 | −2.618 | −5.508 | 1.00 | 4.47 |
| ATOM | 744 | CA | GLY | A | 219 | 6.144 | −1.458 | −5.636 | 1.00 | 4.95 |
| ATOM | 745 | C | GLY | A | 219 | 7.618 | −1.640 | −5.271 | 1.00 | 4.49 |
| ATOM | 746 | O | GLY | A | 219 | 8.464 | −0.930 | −5.806 | 1.00 | 4.95 |
| ATOM | 747 | N | THR | A | 220 | 7.918 | −2.630 | −4.448 | 1.00 | 4.97 |
| ATOM | 748 | CA | THR | A | 220 | 9.303 | −2.943 | −4.105 | 1.00 | 4.75 |
| ATOM | 749 | CB | THR | A | 220 | 9.300 | −3.873 | −2.911 | 1.00 | 5.04 |
| ATOM | 750 | OG1 | THR | A | 220 | 8.735 | −3.195 | −1.748 | 1.00 | 5.77 |
| ATOM | 751 | CG2 | THR | A | 220 | 10.720 | −4.341 | −2.527 | 1.00 | 5.11 |
| ATOM | 752 | C | THR | A | 220 | 10.003 | −3.622 | −5.272 | 1.00 | 4.30 |
| ATOM | 753 | O | THR | A | 220 | 11.116 | −3.311 | −5.610 | 1.00 | 5.06 |
| ATOM | 754 | N | HIS | A | 221 | 9.239 | −4.476 | −5.991 | 1.00 | 4.45 |
| ATOM | 755 | CA | HIS | A | 221 | 9.742 | −5.148 | −7.185 | 1.00 | 4.74 |
| ATOM | 756 | CB | HIS | A | 221 | 8.789 | −6.261 | −7.559 | 1.00 | 4.67 |
| ATOM | 757 | CG | HIS | A | 221 | 9.317 | −7.267 | −8.524 | 1.00 | 4.91 |
| ATOM | 758 | ND1 | HIS | A | 221 | 9.419 | −7.038 | −9.851 | 1.00 | 5.30 |
| ATOM | 759 | CE1 | HIS | A | 221 | 9.994 | −8.088 | −10.423 | 1.00 | 5.39 |
| ATOM | 760 | NE2 | HIS | A | 221 | 10.201 | −8.989 | −9.492 | 1.00 | 5.46 |
| ATOM | 761 | CD2 | HIS | A | 221 | 9.810 | −8.491 | −8.295 | 1.00 | 5.51 |
| ATOM | 762 | C | HIS | A | 221 | 10.010 | −4.157 | −8.282 | 1.00 | 4.16 |
| ATOM | 763 | O | HIS | A | 221 | 11.088 | −4.055 | −8.878 | 1.00 | 4.36 |
| ATOM | 764 | N | VAL | A | 222 | 9.014 | −3.312 | −8.566 | 1.00 | 4.32 |
| ATOM | 765 | CA | VAL | A | 222 | 9.131 | −2.278 | −9.616 | 1.00 | 4.14 |
| ATOM | 766 | CB | VAL | A | 222 | 7.751 | −1.568 | −9.769 | 1.00 | 4.18 |
| ATOM | 767 | CG1 | VAL | A | 222 | 7.870 | −0.344 | −10.631 | 1.00 | 4.46 |
| ATOM | 768 | CG2 | VAL | A | 222 | 6.734 | −2.503 | −10.345 | 1.00 | 4.63 |
| ATOM | 769 | C | VAL | A | 222 | 10.238 | −1.307 | −9.292 | 1.00 | 3.91 |
| ATOM | 770 | O | VAL | A | 222 | 11.050 | −0.965 | −10.166 | 1.00 | 4.33 |
| ATOM | 771 | N | ALA | A | 223 | 10.296 | −0.808 | −8.057 | 1.00 | 4.38 |
| ATOM | 772 | CA | ALA | A | 223 | 11.374 | 0.117 | −7.729 | 1.00 | 4.85 |
| ATOM | 773 | CB | ALA | A | 223 | 11.208 | 0.687 | −6.315 | 1.00 | 5.91 |
| ATOM | 774 | C | ALA | A | 223 | 12.759 | −0.494 | −7.922 | 1.00 | 4.94 |
| ATOM | 775 | O | ALA | A | 223 | 13.680 | 0.242 | −8.289 | 1.00 | 5.10 |
| ATOM | 776 | N | GLY | A | 224 | 12.897 | −1.778 | −7.563 | 1.00 | 4.62 |
| ATOM | 777 | CA | GLY | A | 224 | 14.195 | −2.422 | −7.784 | 1.00 | 4.77 |
| ATOM | 778 | C | GLY | A | 224 | 14.589 | −2.549 | −9.243 | 1.00 | 4.86 |
| ATOM | 779 | O | GLY | A | 224 | 15.779 | −2.438 | −9.565 | 1.00 | 5.03 |
| ATOM | 780 | N | THR | A | 225 | 13.586 | −2.731 | −10.149 | 1.00 | 4.29 |
| ATOM | 781 | CA | THR | A | 225 | 13.961 | −2.742 | −11.536 | 1.00 | 4.60 |
| ATOM | 782 | CB | THR | A | 225 | 12.741 | −3.163 | −12.433 | 1.00 | 4.81 |
| ATOM | 783 | OG1 | THR | A | 225 | 12.367 | −4.489 | −11.995 | 1.00 | 5.17 |
| ATOM | 784 | CG2 | THR | A | 225 | 13.039 | −3.100 | −13.848 | 1.00 | 4.90 |
| ATOM | 785 | C | THR | A | 225 | 14.464 | −1.374 | −11.957 | 1.00 | 5.08 |
| ATOM | 786 | O | THR | A | 225 | 15.437 | −1.262 | −12.711 | 1.00 | 5.31 |
| ATOM | 787 | N | VAL | A | 226 | 13.827 | −0.323 | −11.449 | 1.00 | 4.57 |
| ATOM | 788 | CA | VAL | A | 226 | 14.330 | 1.029 | −11.809 | 1.00 | 4.72 |
| ATOM | 789 | CB | VAL | A | 226 | 13.383 | 2.137 | −11.308 | 1.00 | 4.59 |
| ATOM | 790 | CG1 | VAL | A | 226 | 13.975 | 3.517 | −11.600 | 1.00 | 5.81 |
| ATOM | 791 | CG2 | VAL | A | 226 | 11.983 | 1.939 | −11.936 | 1.00 | 4.58 |
| ATOM | 792 | C | VAL | A | 226 | 15.710 | 1.305 | −11.229 | 1.00 | 4.90 |
| ATOM | 793 | O | VAL | A | 226 | 16.605 | 1.780 | −11.968 | 1.00 | 6.04 |
| ATOM | 794 | N | ALA | A | 227 | 15.945 | 0.990 | −9.969 | 1.00 | 5.55 |
| ATOM | 795 | CA | ALA | A | 227 | 17.134 | 1.499 | −9.290 | 1.00 | 5.21 |
| ATOM | 796 | CB | ALA | A | 227 | 16.935 | 2.957 | −8.911 | 1.00 | 6.76 |
| ATOM | 797 | C | ALA | A | 227 | 17.574 | 0.635 | −8.072 | 1.00 | 5.23 |
| ATOM | 798 | O | ALA | A | 227 | 18.111 | 1.202 | −7.102 | 1.00 | 6.20 |
| ATOM | 799 | N | ALA | A | 228 | 17.555 | −0.681 | −8.147 | 1.00 | 4.90 |
| ATOM | 800 | CA | ALA | A | 228 | 18.229 | −1.491 | −7.130 | 1.00 | 5.55 |
| ATOM | 801 | CB | ALA | A | 228 | 18.192 | −2.954 | −7.426 | 1.00 | 5.94 |
| ATOM | 802 | C | ALA | A | 228 | 19.693 | −1.021 | −7.093 | 1.00 | 6.47 |
| ATOM | 803 | O | ALA | A | 228 | 20.330 | −0.670 | −8.057 | 1.00 | 6.25 |
| ATOM | 804 | N | VAL | A | 229 | 20.218 | −1.123 | −5.852 | 1.00 | 6.64 |
| ATOM | 805 | CA | VAL | A | 229 | 21.624 | −0.770 | −5.586 | 1.00 | 7.17 |
| ATOM | 806 | CB | VAL | A | 229 | 21.870 | −0.723 | −4.112 | 1.00 | 7.60 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 807 | CG1 | VAL | A | 229 | 23.399 | −0.422 | −3.881 | 1.00 | 9.16 |
| ATOM | 808 | CG2 | VAL | A | 229 | 21.013 | 0.294 | −3.335 | 1.00 | 7.45 |
| ATOM | 809 | C | VAL | A | 229 | 22.522 | −1.777 | −6.292 | 1.00 | 6.02 |
| ATOM | 810 | O | VAL | A | 229 | 22.329 | −2.973 | −6.121 | 1.00 | 6.69 |
| ATOM | 811 | N | THR | A | 230 | 23.410 | −1.307 | −7.115 | 1.00 | 6.10 |
| ATOM | 812 | CA | THR | A | 230 | 24.166 | −2.102 | −8.045 | 1.00 | 7.34 |
| ATOM | 813 | CB | THR | A | 230 | 23.812 | −1.660 | −9.452 | 1.00 | 6.87 |
| ATOM | 814 | OG1 | THR | A | 230 | 22.398 | −1.910 | −9.610 | 1.00 | 7.41 |
| ATOM | 815 | CG2 | THR | A | 230 | 24.510 | −2.400 | −10.534 | 1.00 | 7.60 |
| ATOM | 816 | C | THR | A | 230 | 25.685 | −1.964 | −7.702 | 1.00 | 8.01 |
| ATOM | 817 | O | THR | A | 230 | 26.137 | −0.947 | −7.210 | 1.00 | 9.48 |
| ATOM | 818 | N | ASN | A | 231 | 26.388 | −3.043 | −8.058 | 1.00 | 8.75 |
| ATOM | 819 | CA | ASN | A | 231 | 27.866 | −3.114 | −7.787 | 1.00 | 10.63 |
| ATOM | 820 | CB | ASN | A | 231 | 28.624 | −1.998 | −8.483 | 1.00 | 11.86 |
| ATOM | 821 | CG | ASN | A | 231 | 28.911 | −2.370 | −9.833 | 1.00 | 15.66 |
| ATOM | 822 | OD1 | ASN | A | 231 | 29.324 | −3.518 | −10.096 | 1.00 | 19.43 |
| ATOM | 823 | ND2 | ASN | A | 231 | 28.782 | −1.396 | −10.709 | 1.00 | 18.84 |
| ATOM | 824 | C | ASN | A | 231 | 28.129 | −3.131 | −6.373 | 1.00 | 12.07 |
| ATOM | 825 | O | ASN | A | 231 | 29.251 | −2.726 | −5.961 | 1.00 | 14.30 |
| ATOM | 826 | N | ASN | A | 232 | 27.231 | −3.601 | −5.538 | 1.00 | 8.94 |
| ATOM | 827 | CA | ASN | A | 232 | 27.419 | −3.765 | −4.096 | 1.00 | 9.39 |
| ATOM | 828 | CB | ASN | A | 232 | 26.302 | −3.087 | −3.269 | 1.00 | 9.14 |
| ATOM | 829 | CG | ASN | A | 232 | 24.936 | −3.758 | −3.486 | 1.00 | 7.37 |
| ATOM | 830 | OD1 | ASN | A | 232 | 24.722 | −4.465 | −4.495 | 1.00 | 8.78 |
| ATOM | 831 | ND2 | ASN | A | 232 | 24.059 | −3.607 | −2.538 | 1.00 | 8.00 |
| ATOM | 832 | C | ASN | A | 232 | 27.652 | −5.202 | −3.670 | 1.00 | 8.81 |
| ATOM | 833 | O | ASN | A | 232 | 27.538 | −5.537 | −2.506 | 1.00 | 10.78 |
| ATOM | 834 | N | GLY | A | 233 | 27.871 | −6.098 | −4.632 | 1.00 | 9.35 |
| ATOM | 835 | CA | GLY | A | 233 | 28.127 | −7.448 | −4.304 | 1.00 | 10.02 |
| ATOM | 836 | C | GLY | A | 233 | 27.087 | −8.256 | −3.714 | 1.00 | 10.05 |
| ATOM | 837 | O | GLY | A | 233 | 27.269 | −9.339 | −3.113 | 1.00 | 12.28 |
| ATOM | 838 | N | GLU | A | 234 | 25.813 | −7.749 | −3.841 | 1.00 | 10.22 |
| ATOM | 839 | CA | GLU | A | 234 | 24.679 | −8.288 | −3.156 | 1.00 | 10.60 |
| ATOM | 840 | CB | GLU | A | 234 | 24.302 | −7.434 | −1.923 | 1.00 | 13.14 |
| ATOM | 841 | CG | GLU | A | 234 | 23.161 | −7.904 | −1.128 | 1.00 | 15.74 |
| ATOM | 842 | CD | GLU | A | 234 | 22.913 | −7.005 | 0.140 | 1.00 | 18.30 |
| ATOM | 843 | OE1 | GLU | A | 234 | 21.922 | −7.310 | 0.863 | 1.00 | 19.80 |
| ATOM | 844 | OE2 | GLU | A | 234 | 23.733 | −6.063 | 0.356 | 1.00 | 20.57 |
| ATOM | 845 | C | GLU | A | 234 | 23.447 | −8.305 | −4.109 | 1.00 | 8.14 |
| ATOM | 846 | O | GLU | A | 234 | 23.282 | −7.327 | −4.814 | 1.00 | 8.02 |
| ATOM | 847 | N | GLY | A | 235 | 22.679 | −9.335 | −4.106 | 1.00 | 7.54 |
| ATOM | 848 | CA | GLY | A | 235 | 21.354 | −9.286 | −4.757 | 1.00 | 7.74 |
| ATOM | 849 | C | GLY | A | 235 | 21.495 | −9.012 | −6.228 | 1.00 | 7.31 |
| ATOM | 850 | O | GLY | A | 235 | 22.250 | −9.618 | −7.007 | 1.00 | 7.35 |
| ATOM | 851 | N | VAL | A | 236 | 20.648 | −8.080 | −6.681 | 1.00 | 6.74 |
| ATOM | 852 | CA | VAL | A | 236 | 20.372 | −7.701 | −8.072 | 1.00 | 6.15 |
| ATOM | 853 | CB | VAL | A | 236 | 18.806 | −7.744 | −8.309 | 1.00 | 6.57 |
| ATOM | 854 | CG1 | VAL | A | 236 | 18.238 | −9.127 | −8.145 | 1.00 | 7.27 |
| ATOM | 855 | CG2 | VAL | A | 236 | 18.126 | −6.754 | −7.397 | 1.00 | 6.46 |
| ATOM | 856 | C | VAL | A | 236 | 20.946 | −6.398 | −8.534 | 1.00 | 5.64 |
| ATOM | 857 | O | VAL | A | 236 | 21.523 | −5.647 | −7.663 | 1.00 | 6.39 |
| ATOM | 858 | N | ALA | A | 237 | 20.770 | −6.064 | −9.815 | 1.00 | 5.71 |
| ATOM | 859 | CA | ALA | A | 237 | 21.051 | −4.773 | −10.332 | 1.00 | 5.75 |
| ATOM | 860 | CB | ALA | A | 237 | 22.013 | −4.879 | −11.501 | 1.00 | 7.74 |
| ATOM | 861 | C | ALA | A | 237 | 19.775 | −4.055 | −10.737 | 1.00 | 6.15 |
| ATOM | 862 | O | ALA | A | 237 | 18.715 | −4.672 | −10.840 | 1.00 | 6.36 |
| ATOM | 863 | N | GLY | A | 238 | 19.908 | −2.747 | −10.899 | 1.00 | 5.24 |
| ATOM | 864 | CA | GLY | A | 238 | 18.806 | −1.887 | −11.354 | 1.00 | 5.24 |
| ATOM | 865 | C | GLY | A | 238 | 19.161 | −1.313 | −12.698 | 1.00 | 5.44 |
| ATOM | 866 | O | GLY | A | 238 | 20.319 | −1.162 | −13.094 | 1.00 | 6.90 |
| ATOM | 867 | N | VAL | A | 239 | 18.159 | −0.906 | −13.500 | 1.00 | 5.05 |
| ATOM | 868 | CA | VAL | A | 239 | 18.389 | −0.348 | −14.831 | 1.00 | 5.73 |
| ATOM | 869 | CB | VAL | A | 239 | 17.035 | −0.260 | −15.579 | 1.00 | 5.25 |
| ATOM | 870 | CG1 | VAL | A | 239 | 17.203 | 0.460 | −16.909 | 1.00 | 5.92 |
| ATOM | 871 | CG2 | VAL | A | 239 | 16.449 | −1.641 | −15.779 | 1.00 | 5.74 |
| ATOM | 872 | C | VAL | A | 239 | 19.085 | 0.968 | −14.764 | 1.00 | 5.55 |
| ATOM | 873 | O | VAL | A | 239 | 20.015 | 1.221 | −15.543 | 1.00 | 6.81 |
| ATOM | 874 | N | ALA | A | 240 | 18.580 | 1.874 | −13.929 | 1.00 | 5.48 |
| ATOM | 875 | CA | ALA | A | 240 | 19.144 | 3.205 | −13.737 | 1.00 | 6.06 |
| ATOM | 876 | CB | ALA | A | 240 | 18.146 | 4.300 | −14.029 | 1.00 | 6.87 |
| ATOM | 877 | C | ALA | A | 240 | 19.676 | 3.268 | −12.321 | 1.00 | 5.93 |
| ATOM | 878 | O | ALA | A | 240 | 19.190 | 4.006 | −11.481 | 1.00 | 6.15 |
| ATOM | 879 | N | TYR | A | 241 | 20.769 | 2.516 | −12.067 | 1.00 | 6.17 |
| ATOM | 880 | CA | TYR | A | 241 | 21.204 | 2.225 | −10.719 | 1.00 | 6.10 |
| ATOM | 881 | CB | TYR | A | 241 | 22.053 | 0.970 | −10.673 | 1.00 | 6.60 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 882 | CG | TYR | A | 241 | 23.276 | 0.981 | −11.532 | 1.00 | 7.15 |
| ATOM | 883 | CD1 | TYR | A | 241 | 24.442 | 1.663 | −11.121 | 1.00 | 8.13 |
| ATOM | 884 | CE1 | TYR | A | 241 | 25.635 | 1.581 | −11.866 | 1.00 | 8.02 |
| ATOM | 885 | CZ | TYR | A | 241 | 25.628 | 0.836 | −12.976 | 1.00 | 8.52 |
| ATOM | 886 | OH | TYR | A | 241 | 26.797 | 0.672 | −13.728 | 1.00 | 10.69 |
| ATOM | 887 | CE2 | TYR | A | 241 | 24.492 | 0.212 | −13.433 | 1.00 | 8.91 |
| ATOM | 888 | CD2 | TYR | A | 241 | 23.349 | 0.278 | −12.677 | 1.00 | 7.50 |
| ATOM | 889 | C | TYR | A | 241 | 21.880 | 3.389 | −9.996 | 1.00 | 6.07 |
| ATOM | 890 | O | TYR | A | 241 | 22.047 | 3.288 | −8.742 | 1.00 | 6.86 |
| ATOM | 891 | N | ASN | A | 242 | 22.190 | 4.459 | −10.689 | 1.00 | 6.15 |
| ATOM | 892 | CA | ASN | A | 242 | 22.674 | 5.696 | −9.982 | 1.00 | 7.26 |
| ATOM | 893 | CB | ASN | A | 242 | 23.967 | 6.190 | −10.612 | 1.00 | 7.71 |
| ATOM | 894 | CG | ASN | A | 242 | 25.166 | 5.397 | −10.213 | 1.00 | 8.57 |
| ATOM | 895 | OD1 | ASN | A | 242 | 25.253 | 4.843 | −9.135 | 1.00 | 10.45 |
| ATOM | 896 | ND2 | ASN | A | 242 | 26.039 | 5.196 | −11.172 | 1.00 | 9.24 |
| ATOM | 897 | C | ASN | A | 242 | 21.623 | 6.772 | −9.950 | 1.00 | 7.31 |
| ATOM | 898 | O | ASN | A | 242 | 21.867 | 7.848 | −9.450 | 1.00 | 8.52 |
| ATOM | 899 | N | ALA | A | 243 | 20.370 | 6.473 | −10.424 | 1.00 | 6.93 |
| ATOM | 900 | CA | ALA | A | 243 | 19.236 | 7.348 | −10.188 | 1.00 | 6.35 |
| ATOM | 901 | CB | ALA | A | 243 | 18.137 | 7.068 | −11.186 | 1.00 | 6.56 |
| ATOM | 902 | C | ALA | A | 243 | 18.768 | 7.155 | −8.768 | 1.00 | 7.21 |
| ATOM | 903 | O | ALA | A | 243 | 19.207 | 6.285 | −8.035 | 1.00 | 7.50 |
| ATOM | 904 | N | LYS | A | 244 | 17.778 | 7.930 | −8.366 | 1.00 | 6.74 |
| ATOM | 905 | CA | LYS | A | 244 | 17.078 | 7.768 | −7.108 | 1.00 | 7.56 |
| ATOM | 906 | CB | LYS | A | 244 | 17.296 | 8.944 | −6.165 | 1.00 | 10.32 |
| ATOM | 907 | CG | LYS | A | 244 | 18.718 | 9.160 | −5.833 | 1.00 | 13.60 |
| ATOM | 908 | CD | LYS | A | 244 | 19.279 | 8.077 | −4.980 | 1.00 | 17.31 |
| ATOM | 909 | CE | LYS | A | 244 | 20.665 | 8.533 | −4.375 | 1.00 | 25.46 |
| ATOM | 910 | NZ | LYS | A | 244 | 21.456 | 7.272 | −4.249 | 1.00 | 33.20 |
| ATOM | 911 | C | LYS | A | 244 | 15.568 | 7.660 | −7.355 | 1.00 | 6.32 |
| ATOM | 912 | O | LYS | A | 244 | 15.065 | 8.258 | −8.371 | 1.00 | 6.92 |
| ATOM | 913 | N | VAL | A | 245 | 14.894 | 6.901 | −6.522 | 1.00 | 5.87 |
| ATOM | 914 | CA | VAL | A | 245 | 13.451 | 6.669 | −6.613 | 1.00 | 6.25 |
| ATOM | 915 | CB | VAL | A | 245 | 13.129 | 5.203 | −6.562 | 1.00 | 6.74 |
| ATOM | 916 | CG1 | VAL | A | 245 | 11.625 | 4.919 | −6.341 | 1.00 | 6.97 |
| ATOM | 917 | CG2 | VAL | A | 245 | 13.567 | 4.515 | −7.826 | 1.00 | 7.77 |
| ATOM | 918 | C | VAL | A | 245 | 12.704 | 7.407 | −5.537 | 1.00 | 6.74 |
| ATOM | 919 | O | VAL | A | 245 | 13.060 | 7.304 | −4.350 | 1.00 | 6.32 |
| ATOM | 920 | N | VAL | A | 246 | 11.691 | 8.148 | −5.974 | 1.00 | 5.40 |
| ATOM | 921 | CA | VAL | A | 246 | 10.702 | 8.735 | −5.028 | 1.00 | 5.84 |
| ATOM | 922 | CB | VAL | A | 246 | 10.276 | 10.136 | −5.427 | 1.00 | 5.85 |
| ATOM | 923 | CG1 | VAL | A | 246 | 9.120 | 10.656 | −4.638 | 1.00 | 6.06 |
| ATOM | 924 | CG2 | VAL | A | 246 | 11.456 | 11.072 | −5.307 | 1.00 | 6.78 |
| ATOM | 925 | C | VAL | A | 246 | 9.522 | 7.797 | −5.036 | 1.00 | 5.38 |
| ATOM | 926 | O | VAL | A | 246 | 8.811 | 7.636 | −6.059 | 1.00 | 5.68 |
| ATOM | 927 | N | PRO | A | 247 | 9.212 | 7.128 | −3.950 | 1.00 | 5.41 |
| ATOM | 928 | CA | PRO | A | 247 | 8.066 | 6.263 | −3.851 | 1.00 | 5.68 |
| ATOM | 929 | CB | PRO | A | 247 | 8.388 | 5.348 | −2.669 | 1.00 | 6.41 |
| ATOM | 930 | CG | PRO | A | 247 | 9.232 | 6.241 | −1.764 | 1.00 | 6.73 |
| ATOM | 931 | CD | PRO | A | 247 | 10.017 | 7.145 | −2.677 | 1.00 | 6.06 |
| ATOM | 932 | C | PRO | A | 247 | 6.803 | 7.032 | −3.600 | 1.00 | 4.78 |
| ATOM | 933 | O | PRO | A | 247 | 6.749 | 7.810 | −2.669 | 1.00 | 5.49 |
| ATOM | 934 | N | VAL | A | 248 | 5.816 | 6.898 | −4.473 | 1.00 | 5.14 |
| ATOM | 935 | CA | VAL | A | 248 | 4.527 | 7.567 | −4.336 | 1.00 | 5.39 |
| ATOM | 936 | CB | VAL | A | 248 | 4.259 | 8.530 | −5.503 | 1.00 | 5.52 |
| ATOM | 937 | CG1 | VAL | A | 248 | 2.982 | 9.311 | −5.251 | 1.00 | 6.62 |
| ATOM | 938 | CG2 | VAL | A | 248 | 5.411 | 9.466 | −5.697 | 1.00 | 6.19 |
| ATOM | 939 | C | VAL | A | 248 | 3.529 | 6.498 | −4.189 | 1.00 | 5.25 |
| ATOM | 940 | O | VAL | A | 248 | 3.206 | 5.770 | −5.143 | 1.00 | 6.04 |
| ATOM | 941 | N | ARG | A | 249 | 3.022 | 6.306 | −2.961 | 1.00 | 5.06 |
| ATOM | 942 | CA | ARG | A | 249 | 2.142 | 5.228 | −2.653 | 1.00 | 5.32 |
| ATOM | 943 | CB | ARG | A | 249 | 2.250 | 4.745 | −1.198 | 1.00 | 5.83 |
| ATOM | 944 | CG | ARG | A | 249 | 1.282 | 3.682 | −0.862 | 1.00 | 5.96 |
| ATOM | 945 | CD | ARG | A | 249 | 1.664 | 2.996 | 0.449 | 1.00 | 5.65 |
| ATOM | 946 | NE | ARG | A | 249 | 0.755 | 1.895 | 0.658 | 1.00 | 5.98 |
| ATOM | 947 | CZ | ARG | A | 249 | −0.264 | 1.790 | 1.514 | 1.00 | 5.77 |
| ATOM | 948 | NH1 | ARG | A | 249 | −0.504 | 2.756 | 2.365 | 1.00 | 7.32 |
| ATOM | 949 | NH2 | ARG | A | 249 | −1.049 | 0.742 | 1.494 | 1.00 | 6.35 |
| ATOM | 950 | C | ARG | A | 249 | 0.710 | 5.615 | −3.046 | 1.00 | 5.14 |
| ATOM | 951 | O | ARG | A | 249 | 0.134 | 6.509 | −2.438 | 1.00 | 5.55 |
| ATOM | 952 | N | VAL | A | 250 | 0.153 | 4.900 | −4.011 | 1.00 | 5.71 |
| ATOM | 953 | CA | VAL | A | 250 | −1.186 | 5.154 | −4.506 | 1.00 | 5.93 |
| ATOM | 954 | CB | VAL | A | 250 | −1.143 | 5.824 | −5.910 | 1.00 | 6.23 |
| ATOM | 955 | CG1 | VAL | A | 250 | −0.352 | 7.153 | −5.896 | 1.00 | 6.88 |
| ATOM | 956 | CG2 | VAL | A | 250 | −0.590 | 4.890 | −6.965 | 1.00 | 5.83 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 957 | C | VAL | A | 250 | −2.050 | 3.943 | −4.545 | 1.00 | 6.27 |
| ATOM | 958 | O | VAL | A | 250 | −3.280 | 4.094 | −4.753 | 1.00 | 6.95 |
| ATOM | 959 | N | LEU | A | 251 | −1.527 | 2.764 | −4.292 | 1.00 | 5.77 |
| ATOM | 960 | CA | LEU | A | 251 | −2.250 | 1.475 | −4.325 | 1.00 | 6.61 |
| ATOM | 961 | CB | LEU | A | 251 | −1.692 | 0.533 | −5.378 | 1.00 | 7.12 |
| ATOM | 962 | CG | LEU | A | 251 | −1.510 | 1.066 | −6.805 | 1.00 | 7.36 |
| ATOM | 963 | CD1 | LEU | A | 251 | −0.864 | 0.008 | −7.698 | 1.00 | 8.31 |
| ATOM | 964 | CD2 | LEU | A | 251 | −2.866 | 1.499 | −7.390 | 1.00 | 10.10 |
| ATOM | 965 | C | LEU | A | 251 | −2.116 | 0.786 | −2.982 | 1.00 | 6.74 |
| ATOM | 966 | O | LEU | A | 251 | −1.023 | 0.703 | −2.413 | 1.00 | 6.44 |
| ATOM | 967 | N | GLY | A | 252 | −3.245 | 0.314 | −2.478 | 1.00 | 7.06 |
| ATOM | 968 | CA | GLY | A | 252 | −3.321 | −0.484 | −1.271 | 1.00 | 6.95 |
| ATOM | 969 | C | GLY | A | 252 | −4.178 | −1.666 | −1.401 | 1.00 | 6.86 |
| ATOM | 970 | O | GLY | A | 252 | −4.266 | −2.329 | −2.458 | 1.00 | 7.08 |
| ATOM | 971 | N | LYS | A | 253 | −4.880 | −2.019 | −0.300 | 1.00 | 7.18 |
| ATOM | 972 | CA | LYS | A | 253 | −5.773 | −3.205 | −0.394 | 1.00 | 8.36 |
| ATOM | 973 | CB | LYS | A | 253 | −6.380 | −3.473 | 0.962 | 1.00 | 9.35 |
| ATOM | 974 | CG | LYS | A | 253 | −5.361 | −3.949 | 2.003 | 1.00 | 9.58 |
| ATOM | 975 | CD | LYS | A | 253 | −5.917 | −4.004 | 3.419 | 1.00 | 11.68 |
| ATOM | 976 | CE | LYS | A | 253 | −6.982 | −5.042 | 3.527 | 1.00 | 13.74 |
| ATOM | 977 | NZ | LYS | A | 253 | −7.499 | −5.202 | 4.949 | 1.00 | 15.16 |
| ATOM | 978 | C | LYS | A | 253 | −6.914 | −2.975 | −1.384 | 1.00 | 7.99 |
| ATOM | 979 | O | LYS | A | 253 | −7.608 | −1.933 | −1.254 | 1.00 | 10.37 |
| ATOM | 980 | N | CYS | A | 254 | −7.024 | −3.862 | −2.323 | 1.00 | 9.18 |
| ATOM | 981 | CA | CYS | A | 254 | −8.081 | −3.798 | −3.389 | 1.00 | 10.97 |
| ATOM | 982 | CB | CYS | A | 254 | −9.488 | −3.453 | −2.857 | 1.00 | 12.26 |
| ATOM | 983 | SG | CYS | A | 254 | −9.985 | −4.581 | −1.550 | 1.00 | 14.67 |
| ATOM | 984 | C | CYS | A | 254 | −7.700 | −2.814 | −4.479 | 1.00 | 12.69 |
| ATOM | 985 | O | CYS | A | 254 | −8.509 | −2.689 | −5.457 | 1.00 | 16.80 |
| ATOM | 986 | N | GLY | A | 255 | −6.527 | −2.197 | −4.499 | 1.00 | 9.49 |
| ATOM | 987 | CA | GLY | A | 255 | −6.099 | −1.337 | −5.592 | 1.00 | 10.14 |
| ATOM | 988 | C | GLY | A | 255 | −6.025 | 0.075 | −5.130 | 1.00 | 9.93 |
| ATOM | 989 | O | GLY | A | 255 | −5.648 | 0.412 | −4.033 | 1.00 | 8.93 |
| ATOM | 990 | N | GLY | A | 256 | −6.324 | 1.050 | −6.063 | 1.00 | 9.91 |
| ATOM | 991 | CA | GLY | A | 256 | −6.245 | 2.465 | −5.832 | 1.00 | 9.93 |
| ATOM | 992 | C | GLY | A | 256 | −7.328 | 3.265 | −6.502 | 1.00 | 10.09 |
| ATOM | 993 | O | GLY | A | 256 | −7.936 | 2.762 | −7.443 | 1.00 | 13.46 |
| ATOM | 994 | N | LEU | A | 257 | −7.527 | 4.414 | −5.955 | 1.00 | 9.25 |
| ATOM | 995 | CA | LEU | A | 257 | −8.531 | 5.361 | −6.468 | 1.00 | 8.95 |
| ATOM | 996 | CB | LEU | A | 257 | −8.953 | 6.221 | −5.334 | 1.00 | 12.19 |
| ATOM | 997 | CG | LEU | A | 257 | −10.129 | 7.202 | −5.512 | 1.00 | 18.10 |
| ATOM | 998 | CD1 | LEU | A | 257 | −11.412 | 6.505 | −6.019 | 1.00 | 21.85 |
| ATOM | 999 | CD2 | LEU | A | 257 | −10.460 | 7.968 | −4.192 | 1.00 | 22.02 |
| ATOM | 1000 | C | LEU | A | 257 | −7.926 | 6.243 | −7.558 | 1.00 | 8.83 |
| ATOM | 1001 | O | LEU | A | 257 | −6.841 | 6.820 | −7.352 | 1.00 | 8.21 |
| ATOM | 1002 | N | THR | A | 258 | −8.652 | 6.417 | −8.641 | 1.00 | 9.81 |
| ATOM | 1003 | CA | THR | A | 258 | −8.236 | 7.302 | −9.716 | 1.00 | 10.64 |
| ATOM | 1004 | CB | THR | A | 258 | −9.387 | 7.434 | −10.785 | 1.00 | 12.32 |
| ATOM | 1005 | OG1 | THR | A | 258 | −9.677 | 6.104 | −11.189 | 1.00 | 17.49 |
| ATOM | 1006 | CG2 | THR | A | 258 | −8.946 | 8.382 | −11.935 | 1.00 | 14.19 |
| ATOM | 1007 | C | THR | A | 258 | −7.790 | 8.649 | −9.218 | 1.00 | 9.03 |
| ATOM | 1008 | O | THR | A | 258 | −6.715 | 9.187 | −9.662 | 1.00 | 8.12 |
| ATOM | 1009 | N | SER | A | 259 | −8.480 | 9.287 | −8.299 | 1.00 | 9.39 |
| ATOM | 1010 | CA | SER | A | 259 | −8.152 | 10.570 | −7.861 | 1.00 | 10.48 |
| ATOM | 1011 | CB | SER | A | 259 | −9.314 | 11.279 | −7.102 | 1.00 | 14.15 |
| ATOM | 1012 | OG | SER | A | 259 | −9.714 | 10.414 | −6.132 | 1.00 | 16.77 |
| ATOM | 1013 | C | SER | A | 259 | −6.844 | 10.661 | −7.010 | 1.00 | 9.02 |
| ATOM | 1014 | O | SER | A | 259 | −6.121 | 11.639 | −7.080 | 1.00 | 10.05 |
| ATOM | 1015 | N | ASP | A | 260 | −6.604 | 9.566 | −6.243 | 1.00 | 8.17 |
| ATOM | 1016 | CA | ASP | A | 260 | −5.349 | 9.490 | −5.520 | 1.00 | 7.71 |
| ATOM | 1017 | CB | ASP | A | 260 | −5.378 | 8.342 | −4.527 | 1.00 | 7.43 |
| ATOM | 1018 | CG | ASP | A | 260 | −6.327 | 8.541 | −3.335 | 1.00 | 8.37 |
| ATOM | 1019 | OD1 | ASP | A | 260 | −6.692 | 9.689 | −3.015 | 1.00 | 9.60 |
| ATOM | 1020 | OD2 | ASP | A | 260 | −6.535 | 7.526 | −2.645 | 1.00 | 8.36 |
| ATOM | 1021 | C | ASP | A | 260 | −4.182 | 9.290 | −6.488 | 1.00 | 6.53 |
| ATOM | 1022 | O | ASP | A | 260 | −3.109 | 9.899 | −6.285 | 1.00 | 7.09 |
| ATOM | 1023 | N | ILE | A | 261 | −4.336 | 8.449 | −7.464 | 1.00 | 6.25 |
| ATOM | 1024 | CA | ILE | A | 261 | −3.303 | 8.244 | −8.489 | 1.00 | 6.08 |
| ATOM | 1025 | CB | ILE | A | 261 | −3.704 | 7.131 | −9.455 | 1.00 | 6.71 |
| ATOM | 1026 | CG1 | ILE | A | 261 | −3.840 | 5.824 | −8.664 | 1.00 | 6.87 |
| ATOM | 1027 | CD1 | ILE | A | 261 | −4.616 | 4.751 | −9.389 | 1.00 | 8.00 |
| ATOM | 1028 | CG2 | ILE | A | 261 | −2.734 | 7.056 | −10.585 | 1.00 | 7.12 |
| ATOM | 1029 | C | ILE | A | 261 | −2.984 | 9.544 | −9.180 | 1.00 | 6.73 |
| ATOM | 1030 | O | ILE | A | 261 | −1.813 | 9.895 | −9.401 | 1.00 | 6.78 |
| ATOM | 1031 | N | ALA | A | 262 | −4.016 | 10.288 | −9.542 | 1.00 | 6.85 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1032 | CA | ALA | A | 262 | −3.826 | 11.564 | −10.259 | 1.00 | 6.67 |
| ATOM | 1033 | CB | ALA | A | 262 | −5.174 | 12.082 | −10.732 | 1.00 | 8.05 |
| ATOM | 1034 | C | ALA | A | 262 | −3.107 | 12.575 | −9.408 | 1.00 | 6.45 |
| ATOM | 1035 | O | ALA | A | 262 | −2.175 | 13.253 | −9.874 | 1.00 | 6.76 |
| ATOM | 1036 | N | ASP | A | 263 | −3.450 | 12.694 | −8.123 | 1.00 | 6.58 |
| ATOM | 1037 | CA | ASP | A | 263 | −2.701 | 13.562 | −7.228 | 1.00 | 6.94 |
| ATOM | 1038 | CB | ASP | A | 263 | −3.420 | 13.706 | −5.908 | 1.00 | 8.02 |
| ATOM | 1039 | CG | ASP | A | 263 | −4.623 | 14.581 | −5.966 | 1.00 | 8.36 |
| ATOM | 1040 | OD1 | ASP | A | 263 | −4.750 | 15.377 | −6.937 | 1.00 | 10.85 |
| ATOM | 1041 | OD2 | ASP | A | 263 | −5.415 | 14.551 | −5.005 | 1.00 | 9.59 |
| ATOM | 1042 | C | ASP | A | 263 | −1.229 | 13.139 | −7.063 | 1.00 | 6.95 |
| ATOM | 1043 | O | ASP | A | 263 | −0.307 | 13.932 | −6.949 | 1.00 | 6.77 |
| ATOM | 1044 | N | GLY | A | 264 | −1.038 | 11.793 | −7.106 | 1.00 | 5.92 |
| ATOM | 1045 | CA | GLY | A | 264 | 0.317 | 11.300 | −7.125 | 1.00 | 5.79 |
| ATOM | 1046 | C | GLY | A | 264 | 1.169 | 11.740 | −8.312 | 1.00 | 5.75 |
| ATOM | 1047 | O | GLY | A | 264 | 2.314 | 12.095 | −8.173 | 1.00 | 6.19 |
| ATOM | 1048 | N | ILE | A | 265 | 0.509 | 11.693 | −9.486 | 1.00 | 5.47 |
| ATOM | 1049 | CA | ILE | A | 265 | 1.179 | 12.139 | −10.729 | 1.00 | 5.79 |
| ATOM | 1050 | CB | ILE | A | 265 | 0.250 | 11.968 | −11.930 | 1.00 | 5.68 |
| ATOM | 1051 | CG1 | ILE | A | 265 | −0.031 | 10.446 | −12.213 | 1.00 | 6.12 |
| ATOM | 1052 | CD1 | ILE | A | 265 | −1.150 | 10.186 | −13.166 | 1.00 | 6.43 |
| ATOM | 1053 | CG2 | ILE | A | 265 | 0.761 | 12.678 | −13.144 | 1.00 | 5.98 |
| ATOM | 1054 | C | ILE | A | 265 | 1.550 | 13.628 | −10.605 | 1.00 | 6.09 |
| ATOM | 1055 | O | ILE | A | 265 | 2.697 | 14.018 | −10.840 | 1.00 | 6.12 |
| ATOM | 1056 | N | ILE | A | 266 | 0.580 | 14.410 | −10.163 | 1.00 | 5.82 |
| ATOM | 1057 | CA | ILE | A | 266 | 0.848 | 15.876 | −9.992 | 1.00 | 6.32 |
| ATOM | 1058 | CB | ILE | A | 266 | −0.452 | 16.574 | −9.515 | 1.00 | 6.83 |
| ATOM | 1059 | CG1 | ILE | A | 266 | −1.523 | 16.502 | −10.585 | 1.00 | 7.13 |
| ATOM | 1060 | CD1 | ILE | A | 266 | −2.888 | 16.779 | −10.035 | 1.00 | 8.04 |
| ATOM | 1061 | CG2 | ILE | A | 266 | −0.152 | 18.054 | −9.109 | 1.00 | 7.65 |
| ATOM | 1062 | C | ILE | A | 266 | 2.019 | 16.137 | −9.023 | 1.00 | 6.10 |
| ATOM | 1063 | O | ILE | A | 266 | 2.986 | 16.814 | −9.370 | 1.00 | 6.21 |
| ATOM | 1064 | N | TRP | A | 267 | 1.896 | 15.533 | −7.838 | 1.00 | 5.45 |
| ATOM | 1065 | CA | TRP | A | 267 | 2.916 | 15.792 | −6.811 | 1.00 | 6.03 |
| ATOM | 1066 | CB | TRP | A | 267 | 2.433 | 15.143 | −5.472 | 1.00 | 6.31 |
| ATOM | 1067 | CG | TRP | A | 267 | 3.353 | 15.405 | −4.313 | 1.00 | 6.84 |
| ATOM | 1068 | CD1 | TRP | A | 267 | 3.368 | 16.549 | −3.498 | 1.00 | 7.96 |
| ATOM | 1069 | NE1 | TRP | A | 267 | 4.337 | 16.395 | −2.573 | 1.00 | 9.06 |
| ATOM | 1070 | CE2 | TRP | A | 267 | 5.048 | 15.255 | −2.758 | 1.00 | 7.31 |
| ATOM | 1071 | CD2 | TRP | A | 267 | 4.424 | 14.590 | −3.844 | 1.00 | 7.20 |
| ATOM | 1072 | CE3 | TRP | A | 267 | 4.960 | 13.358 | −4.257 | 1.00 | 7.18 |
| ATOM | 1073 | CZ3 | TRP | A | 267 | 6.030 | 12.865 | −3.566 | 1.00 | 7.97 |
| ATOM | 1074 | CH2 | TRP | A | 267 | 6.602 | 13.549 | −2.484 | 1.00 | 7.66 |
| ATOM | 1075 | CZ2 | TRP | A | 267 | 6.089 | 14.687 | −2.055 | 1.00 | 8.56 |
| ATOM | 1076 | C | TRP | A | 267 | 4.290 | 15.297 | −7.237 | 1.00 | 6.14 |
| ATOM | 1077 | O | TRP | A | 267 | 5.319 | 15.894 | −6.963 | 1.00 | 7.03 |
| ATOM | 1078 | N | ALA | A | 268 | 4.324 | 14.095 | −7.849 | 1.00 | 5.33 |
| ATOM | 1079 | CA | ALA | A | 268 | 5.563 | 13.481 | −8.266 | 1.00 | 5.53 |
| ATOM | 1080 | CB | ALA | A | 268 | 5.316 | 12.200 | −9.003 | 1.00 | 5.81 |
| ATOM | 1081 | C | ALA | A | 268 | 6.324 | 14.384 | −9.196 | 1.00 | 5.99 |
| ATOM | 1082 | O | ALA | A | 268 | 7.562 | 14.427 | −9.189 | 1.00 | 6.17 |
| ATOM | 1083 | N | SER | A | 269 | 5.587 | 15.152 | −10.034 | 1.00 | 5.83 |
| ATOM | 1084 | CA | SER | A | 269 | 6.202 | 16.072 | −10.995 | 1.00 | 6.89 |
| ATOM | 1085 | CB | SER | A | 269 | 5.235 | 16.305 | −12.143 | 1.00 | 6.90 |
| ATOM | 1086 | OG | SER | A | 269 | 4.220 | 17.243 | −11.857 | 1.00 | 7.31 |
| ATOM | 1087 | C | SER | A | 269 | 6.648 | 17.405 | −10.385 | 1.00 | 8.30 |
| ATOM | 1088 | O | SER | A | 269 | 7.193 | 18.222 | −11.158 | 1.00 | 9.78 |
| ATOM | 1089 | N | GLY | A | 270 | 6.303 | 17.649 | −9.143 | 1.00 | 7.39 |
| ATOM | 1090 | CA | GLY | A | 270 | 6.600 | 18.935 | −8.507 | 1.00 | 8.65 |
| ATOM | 1091 | C | GLY | A | 270 | 5.433 | 19.840 | −8.555 | 1.00 | 10.47 |
| ATOM | 1092 | 0 | GLY | A | 270 | 5.574 | 21.082 | −8.253 | 1.00 | 11.96 |
| ATOM | 1093 | N | GLY | A | 271 | 4.254 | 19.401 | −8.916 | 1.00 | 9.96 |
| ATOM | 1094 | CA | GLY | A | 271 | 3.096 | 20.224 | −8.826 | 1.00 | 9.95 |
| ATOM | 1095 | C | GLY | A | 271 | 2.500 | 20.223 | −7.462 | 1.00 | 11.79 |
| ATOM | 1096 | O | GLY | A | 271 | 2.798 | 19.395 | −6.600 | 1.00 | 13.48 |
| ATOM | 1097 | N | SER | A | 272 | 1.552 | 21.106 | −7.238 | 1.00 | 13.99 |
| ATOM | 1098 | CA | SER | A | 272 | 0.959 | 21.296 | −5.925 | 1.00 | 14.15 |
| ATOM | 1099 | CB | SER | A | 272 | 0.788 | 22.819 | −5.639 | 1.00 | 17.92 |
| ATOM | 1100 | OG | SER | A | 272 | 0.229 | 23.073 | −4.325 | 1.00 | 26.73 |
| ATOM | 1101 | C | SER | A | 272 | −0.358 | 20.554 | −5.773 | 1.00 | 13.01 |
| ATOM | 1102 | O | SER | A | 272 | −1.188 | 20.583 | −6.699 | 1.00 | 15.70 |
| ATOM | 1103 | N | VAL | A | 273 | −0.539 | 19.909 | −4.610 | 1.00 | 10.80 |
| ATOM | 1104 | CA | VAL | A | 273 | −1.756 | 19.215 | −4.237 | 1.00 | 11.04 |
| ATOM | 1105 | CB | VAL | A | 273 | −1.535 | 17.679 | −4.149 | 1.00 | 10.96 |
| ATOM | 1106 | CG1 | VAL | A | 273 | −2.728 | 16.946 | −3.608 | 1.00 | 11.20 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1107 | CG2 | VAL | A | 273 | −1.057 | 17.164 | −5.507 | 1.00 | 11.40 |
| ATOM | 1108 | C | VAL | A | 273 | −2.130 | 19.836 | −2.918 | 1.00 | 12.31 |
| ATOM | 1109 | O | VAL | A | 273 | −1.372 | 19.902 | −1.983 | 1.00 | 11.77 |
| ATOM | 1110 | N | SER | A | 274 | −3.409 | 20.202 | −2.826 | 1.00 | 14.45 |
| ATOM | 1111 | CA | SER | A | 274 | −3.909 | 20.763 | −1.522 | 1.00 | 15.38 |
| ATOM | 1112 | CB | SER | A | 274 | −5.406 | 20.989 | −1.732 | 1.00 | 15.81 |
| ATOM | 1113 | OG | SER | A | 274 | −5.696 | 21.991 | −2.743 | 1.00 | 26.14 |
| ATOM | 1114 | C | SER | A | 274 | −3.710 | 19.802 | −0.331 | 1.00 | 13.55 |
| ATOM | 1115 | O | SER | A | 274 | −3.930 | 18.639 | −0.589 | 1.00 | 21.53 |
| ATOM | 1116 | N | GLY | A | 275 | −3.094 | 20.354 | 0.717 | 1.00 | 18.38 |
| ATOM | 1117 | CA | GLY | A | 275 | −2.880 | 19.649 | 1.986 | 1.00 | 17.94 |
| ATOM | 1118 | C | GLY | A | 275 | −1.596 | 18.853 | 1.990 | 1.00 | 19.27 |
| ATOM | 1119 | O | GLY | A | 275 | −1.263 | 18.225 | 2.966 | 1.00 | 23.01 |
| ATOM | 1120 | N | ILE | A | 276 | −0.790 | 18.940 | 0.942 | 1.00 | 14.27 |
| ATOM | 1121 | CA | ILE | A | 276 | 0.403 | 18.122 | 0.885 | 1.00 | 13.55 |
| ATOM | 1122 | CB | ILE | A | 276 | 0.412 | 17.199 | −0.358 | 1.00 | 14.72 |
| ATOM | 1123 | CG1 | ILE | A | 276 | −0.829 | 16.308 | −0.406 | 1.00 | 16.48 |
| ATOM | 1124 | CD1 | ILE | A | 276 | −0.730 | 15.235 | −1.457 | 1.00 | 18.90 |
| ATOM | 1125 | CG2 | ILE | A | 276 | 1.661 | 16.308 | −0.382 | 1.00 | 14.09 |
| ATOM | 1126 | C | ILE | A | 276 | 1.625 | 19.086 | 0.808 | 1.00 | 11.46 |
| ATOM | 1127 | O | ILE | A | 276 | 1.686 | 19.904 | −0.111 | 1.00 | 12.23 |
| ATOM | 1128 | N | PRO | A | 277 | 2.659 | 18.837 | 1.620 | 1.00 | 13.41 |
| ATOM | 1129 | CA | PRO | A | 277 | 3.837 | 19.658 | 1.483 | 1.00 | 13.72 |
| ATOM | 1130 | CB | PRO | A | 277 | 4.772 | 19.154 | 2.604 | 1.00 | 16.49 |
| ATOM | 1131 | CG | PRO | A | 277 | 3.993 | 18.157 | 3.412 | 1.00 | 19.44 |
| ATOM | 1132 | CD | PRO | A | 277 | 2.711 | 17.841 | 2.700 | 1.00 | 16.91 |
| ATOM | 1133 | C | PRO | A | 277 | 4.524 | 19.615 | 0.062 | 1.00 | 11.88 |
| ATOM | 1134 | O | PRO | A | 277 | 4.476 | 18.481 | −0.693 | 1.00 | 13.42 |
| ATOM | 1135 | N | ALA | A | 278 | 5.185 | 20.636 | −0.371 | 1.00 | 15.17 |
| ATOM | 1136 | CA | ALA | A | 278 | 5.785 | 20.612 | −1.660 | 1.00 | 15.11 |
| ATOM | 1137 | CB | ALA | A | 278 | 6.511 | 21.936 | −1.947 | 1.00 | 18.13 |
| ATOM | 1138 | C | ALA | A | 278 | 6.790 | 19.482 | −1.759 | 1.00 | 13.79 |
| ATOM | 1139 | O | ALA | A | 278 | 7.515 | 19.149 | −0.841 | 1.00 | 14.07 |
| ATOM | 1140 | N | ASN | A | 279 | 6.866 | 18.855 | −2.928 | 1.00 | 12.14 |
| ATOM | 1141 | CA | ASN | A | 279 | 7.859 | 17.804 | −3.184 | 1.00 | 10.11 |
| ATOM | 1142 | CB | ASN | A | 279 | 7.411 | 17.051 | −4.414 | 1.00 | 8.65 |
| ATOM | 1143 | CG | ASN | A | 279 | 8.240 | 15.817 | −4.666 | 1.00 | 7.63 |
| ATOM | 1144 | OD1 | ASN | A | 279 | 9.254 | 15.517 | −4.022 | 1.00 | 8.87 |
| ATOM | 1145 | ND2 | ASN | A | 279 | 7.846 | 15.091 | −5.700 | 1.00 | 8.18 |
| ATOM | 1146 | C | ASN | A | 279 | 9.268 | 18.381 | −3.356 | 1.00 | 10.02 |
| ATOM | 1147 | O | ASN | A | 279 | 9.491 | 19.134 | −4.324 | 1.00 | 12.54 |
| ATOM | 1148 | N | SER | A | 280 | 10.192 | 18.052 | −2.457 | 1.00 | 10.05 |
| ATOM | 1149 | CA | SER | A | 280 | 11.495 | 18.549 | −2.626 | 1.00 | 11.95 |
| ATOM | 1150 | CB | SER | A | 280 | 12.275 | 18.733 | −1.358 | 1.00 | 17.79 |
| ATOM | 1151 | OG | SER | A | 280 | 12.239 | 17.687 | −0.676 | 1.00 | 22.04 |
| ATOM | 1152 | C | SER | A | 280 | 12.368 | 17.842 | −3.650 | 1.00 | 11.25 |
| ATOM | 1153 | O | SER | A | 280 | 13.473 | 18.263 | −3.986 | 1.00 | 12.26 |
| ATOM | 1154 | N | ASN | A | 281 | 11.851 | 16.723 | −4.230 | 1.00 | 9.31 |
| ATOM | 1155 | CA | ASN | A | 281 | 12.519 | 15.954 | −5.198 | 1.00 | 9.16 |
| ATOM | 1156 | CB | ASN | A | 281 | 12.989 | 14.617 | −4.612 | 1.00 | 9.81 |
| ATOM | 1157 | CG | ASN | A | 281 | 13.889 | 14.777 | −3.391 | 1.00 | 10.78 |
| ATOM | 1158 | OD1 | ASN | A | 281 | 15.049 | 15.136 | −3.639 | 1.00 | 12.93 |
| ATOM | 1159 | ND2 | ASN | A | 281 | 13.393 | 14.466 | −2.242 | 1.00 | 10.82 |
| ATOM | 1160 | C | ASN | A | 281 | 11.655 | 15.719 | −6.419 | 1.00 | 9.16 |
| ATOM | 1161 | O | ASN | A | 281 | 11.289 | 14.537 | −6.701 | 1.00 | 8.57 |
| ATOM | 1162 | N | PRO | A | 282 | 11.300 | 16.743 | −7.133 | 1.00 | 8.30 |
| ATOM | 1163 | CA | PRO | A | 282 | 10.492 | 16.544 | −8.349 | 1.00 | 8.28 |
| ATOM | 1164 | CB | PRO | A | 282 | 10.342 | 17.939 | −8.996 | 1.00 | 9.66 |
| ATOM | 1165 | CG | PRO | A | 282 | 11.444 | 18.719 | −8.327 | 1.00 | 12.41 |
| ATOM | 1166 | CD | PRO | A | 282 | 11.756 | 18.144 | −6.985 | 1.00 | 10.17 |
| ATOM | 1167 | C | PRO | A | 282 | 11.168 | 15.565 | −9.278 | 1.00 | 8.13 |
| ATOM | 1168 | O | PRO | A | 282 | 12.360 | 15.534 | −9.457 | 1.00 | 9.78 |
| ATOM | 1169 | N | ALA | A | 283 | 10.301 | 14.746 | −9.919 | 1.00 | 6.74 |
| ATOM | 1170 | CA | ALA | A | 283 | 10.774 | 13.627 | −10.762 | 1.00 | 6.94 |
| ATOM | 1171 | CB | ALA | A | 283 | 9.833 | 12.452 | −10.671 | 1.00 | 7.83 |
| ATOM | 1172 | C | ALA | A | 283 | 11.005 | 14.021 | −12.180 | 1.00 | 6.35 |
| ATOM | 1173 | O | ALA | A | 283 | 10.242 | 14.783 | −12.758 | 1.00 | 8.11 |
| ATOM | 1174 | N | ASP | A | 284 | 12.017 | 13.476 | −12.788 | 1.00 | 6.31 |
| ATOM | 1175 | CA | ASP | A | 284 | 12.225 | 13.493 | −14.216 | 1.00 | 7.04 |
| ATOM | 1176 | CB | ASP | A | 284 | 13.699 | 13.242 | −14.520 | 1.00 | 7.44 |
| ATOM | 1177 | CG | ASP | A | 284 | 14.611 | 14.165 | −13.785 | 1.00 | 9.45 |
| ATOM | 1178 | OD1 | ASP | A | 284 | 14.612 | 15.324 | −14.180 | 1.00 | 17.29 |
| ATOM | 1179 | OD2 | ASP | A | 284 | 15.242 | 13.874 | −12.775 | 1.00 | 9.56 |
| ATOM | 1180 | C | ASP | A | 284 | 11.382 | 12.496 | −15.008 | 1.00 | 5.94 |
| ATOM | 1181 | O | ASP | A | 284 | 11.002 | 12.712 | −16.142 | 1.00 | 6.32 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1182 | N | VAL | A | 285 | 11.068 | 11.418 | −14.313 | 1.00 | 5.19 |
| ATOM | 1183 | CA | VAL | A | 285 | 10.379 | 10.261 | −14.950 | 1.00 | 4.89 |
| ATOM | 1184 | CB | VAL | A | 285 | 11.347 | 9.114 | −15.228 | 1.00 | 5.45 |
| ATOM | 1185 | CG1 | VAL | A | 285 | 10.636 | 7.921 | −15.869 | 1.00 | 5.56 |
| ATOM | 1186 | CG2 | VAL | A | 285 | 12.519 | 9.570 | −16.032 | 1.00 | 5.70 |
| ATOM | 1187 | C | VAL | A | 285 | 9.315 | 9.792 | −13.935 | 1.00 | 4.48 |
| ATOM | 1188 | O | VAL | A | 285 | 9.656 | 9.702 | −12.747 | 1.00 | 5.18 |
| ATOM | 1189 | N | ILE | A | 286 | 8.120 | 9.476 | −14.400 | 1.00 | 4.40 |
| ATOM | 1190 | CA | ILE | A | 286 | 7.099 | 8.761 | −13.620 | 1.00 | 4.82 |
| ATOM | 1191 | CB | ILE | A | 286 | 5.776 | 9.499 | −13.627 | 1.00 | 5.15 |
| ATOM | 1192 | CG1 | ILE | A | 286 | 5.846 | 10.743 | −12.668 | 1.00 | 5.83 |
| ATOM | 1193 | CD1 | ILE | A | 286 | 4.742 | 11.702 | −12.908 | 1.00 | 7.06 |
| ATOM | 1194 | CG2 | ILE | A | 286 | 4.594 | 8.652 | −13.331 | 1.00 | 5.68 |
| ATOM | 1195 | C | ILE | A | 286 | 6.966 | 7.407 | −14.206 | 1.00 | 4.95 |
| ATOM | 1196 | O | ILE | A | 286 | 6.829 | 7.231 | −15.439 | 1.00 | 5.80 |
| ATOM | 1197 | N | ASN | A | 287 | 6.925 | 6.392 | −13.349 | 1.00 | 4.39 |
| ATOM | 1198 | CA | ASN | A | 287 | 6.522 | 5.010 | −13.706 | 1.00 | 4.73 |
| ATOM | 1199 | CB | ASN | A | 287 | 7.625 | 4.020 | −13.263 | 1.00 | 4.91 |
| ATOM | 1200 | CG | ASN | A | 287 | 7.327 | 2.629 | −13.726 | 1.00 | 5.06 |
| ATOM | 1201 | OD1 | ASN | A | 287 | 7.750 | 2.246 | −14.821 | 1.00 | 6.39 |
| ATOM | 1202 | ND2 | ASN | A | 287 | 6.538 | 1.866 | −12.951 | 1.00 | 5.38 |
| ATOM | 1203 | C | ASN | A | 287 | 5.197 | 4.671 | −13.082 | 1.00 | 4.41 |
| ATOM | 1204 | O | ASN | A | 287 | 5.037 | 4.781 | −11.856 | 1.00 | 5.46 |
| ATOM | 1205 | N | MET | A | 288 | 4.245 | 4.232 | −13.892 | 1.00 | 4.75 |
| ATOM | 1206 | CA | MET | A | 288 | 2.952 | 3.743 | −13.423 | 1.00 | 5.21 |
| ATOM | 1207 | CB | MET | A | 288 | 1.743 | 4.591 | −13.902 | 1.00 | 6.62 |
| ATOM | 1208 | CG | MET | A | 288 | 1.687 | 5.883 | −13.083 | 1.00 | 8.49 |
| ATOM | 1209 | SD | MET | A | 288 | 0.094 | 6.772 | −13.290 | 1.00 | 13.07 |
| ATOM | 1210 | CE | MET | A | 288 | 0.844 | 7.333 | −14.427 | 1.00 | 4.78 |
| ATOM | 1211 | C | MET | A | 288 | 2.757 | 2.360 | −13.950 | 1.00 | 4.85 |
| ATOM | 1212 | O | MET | A | 288 | 2.243 | 2.064 | −15.069 | 1.00 | 5.84 |
| ATOM | 1213 | N | SER | A | 289 | 3.062 | 1.371 | −13.093 | 1.00 | 5.39 |
| ATOM | 1214 | CA | SER | A | 289 | 2.854 | −0.079 | −13.357 | 1.00 | 5.94 |
| ATOM | 1215 | CB | SER | A | 289 | 3.985 | −0.840 | −12.698 | 1.00 | 5.58 |
| ATOM | 1216 | OG | SER | A | 289 | 5.173 | −0.729 | −13.441 | 1.00 | 5.46 |
| ATOM | 1217 | C | SER | A | 289 | 1.508 | −0.440 | −12.789 | 1.00 | 6.76 |
| ATOM | 1218 | O | SER | A | 289 | 1.408 | −1.182 | −11.780 | 1.00 | 9.17 |
| ATOM | 1219 | N | LEU | A | 290 | 0.442 | 0.111 | −13.317 | 1.00 | 6.50 |
| ATOM | 1220 | CA | LEU | A | 290 | −0.919 | 0.006 | −12.767 | 1.00 | 7.32 |
| ATOM | 1221 | CB | LEU | A | 290 | −1.058 | 0.932 | −11.529 | 1.00 | 9.11 |
| ATOM | 1222 | CG | LEU | A | 290 | −0.895 | 2.437 | −11.810 | 1.00 | 9.49 |
| ATOM | 1223 | CD1 | LEU | A | 290 | −2.127 | 3.091 | −12.475 | 1.00 | 11.92 |
| ATOM | 1224 | CD2 | LEU | A | 290 | −0.569 | 3.260 | −10.567 | 1.00 | 11.15 |
| ATOM | 1225 | C | LEU | A | 290 | −1.911 | 0.306 | −13.848 | 1.00 | 8.73 |
| ATOM | 1226 | O | LEU | A | 290 | −1.551 | 0.899 | −14.911 | 1.00 | 8.82 |
| ATOM | 1227 | N | GLY | A | 291 | −3.128 | −0.080 | −13.637 | 1.00 | 8.02 |
| ATOM | 1228 | CA | GLY | A | 291 | −4.174 | 0.294 | −14.574 | 1.00 | 10.38 |
| ATOM | 1229 | C | GLY | A | 291 | −5.466 | −0.425 | −14.364 | 1.00 | 10.59 |
| ATOM | 1230 | O | GLY | A | 291 | −5.650 | −1.168 | −13.389 | 1.00 | 12.54 |
| ATOM | 1231 | N | GLY | A | 292 | −6.365 | −0.153 | −15.267 | 1.00 | 12.32 |
| ATOM | 1232 | CA | GLY | A | 292 | −7.724 | −0.730 | −15.196 | 1.00 | 14.27 |
| ATOM | 1233 | C | GLY | A | 292 | −8.348 | −0.611 | −16.561 | 1.00 | 15.55 |
| ATOM | 1234 | O | GLY | A | 292 | −7.722 | −0.212 | −17.508 | 1.00 | 12.08 |
| ATOM | 1235 | N | SER | A | 293 | −9.592 | −1.090 | −16.694 | 1.00 | 16.07 |
| ATOM | 1236 | CA | SER | A | 293 | −10.264 | −1.018 | −17.954 | 1.00 | 15.01 |
| ATOM | 1237 | CB | SER | A | 293 | −11.111 | −2.264 | −18.162 | 1.00 | 19.77 |
| ATOM | 1238 | OG | SER | A | 293 | −12.008 | −2.313 | −17.128 | 1.00 | 22.56 |
| ATOM | 1239 | C | SER | A | 293 | −11.052 | 0.254 | −18.114 | 1.00 | 12.44 |
| ATOM | 1240 | O | SER | A | 293 | −11.523 | 0.865 | −17.169 | 1.00 | 15.68 |
| ATOM | 1241 | N | GLY | A | 294 | −11.138 | 0.665 | −19.382 | 1.00 | 10.69 |
| ATOM | 1242 | CA | GLY | A | 294 | −11.955 | 1.805 | −19.766 | 1.00 | 11.92 |
| ATOM | 1243 | C | GLY | A | 294 | −11.173 | 3.008 | −20.208 | 1.00 | 11.73 |
| ATOM | 1244 | O | GLY | A | 294 | −9.941 | 2.965 | −20.296 | 1.00 | 10.64 |
| ATOM | 1245 | N | SER | A | 295 | −11.847 | 4.046 | −20.606 | 1.00 | 11.59 |
| ATOM | 1246 | CA | SER | A | 295 | −11.242 | 5.215 | −21.123 | 1.00 | 11.60 |
| ATOM | 1247 | CB | SER | A | 295 | −12.337 | 6.112 | −21.711 | 1.00 | 14.59 |
| ATOM | 1248 | OG | SER | A | 295 | −13.251 | 6.441 | −20.755 | 1.00 | 17.83 |
| ATOM | 1249 | C | SER | A | 295 | −10.405 | 5.956 | −20.041 | 1.00 | 11.02 |
| ATOM | 1250 | O | SER | A | 295 | −10.576 | 5.752 | −18.868 | 1.00 | 12.16 |
| ATOM | 1251 | N | CYS | A | 296 | −9.461 | 6.753 | −20.539 | 1.00 | 9.96 |
| ATOM | 1252 | CA | CYS | A | 296 | −8.648 | 7.626 | −19.719 | 1.00 | 9.95 |
| ATOM | 1253 | CB | CYS | A | 296 | −7.531 | 8.234 | −20.547 | 1.00 | 9.38 |
| ATOM | 1254 | SG | CYS | A | 296 | −6.451 | 9.352 | −19.620 | 1.00 | 10.13 |
| ATOM | 1255 | C | CYS | A | 296 | −9.567 | 8.755 | −19.167 | 1.00 | 10.16 |
| ATOM | 1256 | O | CYS | A | 296 | −10.116 | 9.498 | −19.984 | 1.00 | 11.87 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1257 | N | SER | A | 297 | −9.661 | 8.912 | −17.872 | 1.00 | 9.61 |
| ATOM | 1258 | CA | SER | A | 297 | −10.508 | 9.933 | −17.412 | 1.00 | 11.76 |
| ATOM | 1259 | CB | SER | A | 297 | −10.893 | 9.683 | −15.989 | 1.00 | 16.12 |
| ATOM | 1260 | OG | SER | A | 297 | −9.836 | 10.089 | −15.117 | 1.00 | 16.26 |
| ATOM | 1261 | C | SER | A | 297 | −9.932 | 11.317 | −17.506 | 1.00 | 10.23 |
| ATOM | 1262 | O | SER | A | 297 | −8.671 | 11.474 | −17.572 | 1.00 | 9.33 |
| ATOM | 1263 | N | SER | A | 298 | −10.749 | 12.339 | −17.477 | 1.00 | 10.50 |
| ATOM | 1264 | CA | SER | A | 298 | −10.279 | 13.700 | −17.536 | 1.00 | 10.32 |
| ATOM | 1265 | CB | SER | A | 298 | −11.339 | 14.792 | −17.490 | 1.00 | 13.80 |
| ATOM | 1266 | OG | SER | A | 298 | −12.265 | 14.461 | −16.607 | 1.00 | 22.94 |
| ATOM | 1267 | C | SER | A | 298 | −9.382 | 13.973 | −16.289 | 1.00 | 9.57 |
| ATOM | 1268 | O | SER | A | 298 | −8.435 | 14.706 | −16.465 | 1.00 | 9.26 |
| ATOM | 1269 | N | THR | A | 299 | −9.664 | 13.438 | −15.111 | 1.00 | 9.37 |
| ATOM | 1270 | CA | THR | A | 299 | −8.859 | 13.684 | −13.924 | 1.00 | 9.40 |
| ATOM | 1271 | CB | THR | A | 299 | −9.462 | 12.907 | −12.745 | 1.00 | 11.36 |
| ATOM | 1272 | OG1 | THR | A | 299 | −10.792 | 13.425 | −12.515 | 1.00 | 14.11 |
| ATOM | 1273 | CG2 | THR | A | 299 | −8.661 | 13.064 | −11.448 | 1.00 | 12.52 |
| ATOM | 1274 | C | THR | A | 299 | −7.435 | 13.166 | −14.230 | 1.00 | 8.25 |
| ATOM | 1275 | O | THR | A | 299 | −6.464 | 13.828 | −13.910 | 1.00 | 8.51 |
| ATOM | 1276 | N | THR | A | 300 | −7.329 | 11.968 | −14.800 | 1.00 | 7.52 |
| ATOM | 1277 | CA | THR | A | 300 | −6.016 | 11.418 | −15.103 | 1.00 | 6.60 |
| ATOM | 1278 | CB | THR | A | 300 | −6.137 | 9.945 | −15.481 | 1.00 | 6.73 |
| ATOM | 1279 | OG1 | THR | A | 300 | −6.888 | 9.287 | −14.435 | 1.00 | 7.87 |
| ATOM | 1280 | CG2 | THR | A | 300 | −4.814 | 9.305 | −15.645 | 1.00 | 7.35 |
| ATOM | 1281 | C | THR | A | 300 | −5.279 | 12.204 | −16.188 | 1.00 | 6.06 |
| ATOM | 1282 | O | THR | A | 300 | −4.110 | 12.514 | −16.038 | 1.00 | 5.90 |
| ATOM | 1283 | N | GLN | A | 301 | −5.944 | 12.526 | −17.287 | 1.00 | 5.83 |
| ATOM | 1284 | CA | GLN | A | 301 | −5.328 | 13.260 | −18.364 | 1.00 | 5.71 |
| ATOM | 1285 | CB | GLN | A | 301 | −6.272 | 13.397 | −19.540 | 1.00 | 5.57 |
| ATOM | 1286 | CG | GLN | A | 301 | −5.614 | 14.030 | −20.753 | 1.00 | 6.20 |
| ATOM | 1287 | CD | GLN | A | 301 | −4.531 | 13.131 | −21.341 | 1.00 | 6.83 |
| ATOM | 1288 | OE1 | GLN | A | 301 | −4.846 | 12.017 | −21.877 | 1.00 | 8.22 |
| ATOM | 1289 | NE2 | GLN | A | 301 | −3.303 | 13.510 | −21.284 | 1.00 | 6.95 |
| ATOM | 1290 | C | GLN | A | 301 | −4.884 | 14.624 | −17.865 | 1.00 | 5.60 |
| ATOM | 1291 | O | GLN | A | 301 | −3.794 | 15.072 | −18.220 | 1.00 | 5.56 |
| ATOM | 1292 | N | ASN | A | 302 | −5.677 | 15.259 | −17.046 | 1.00 | 5.70 |
| ATOM | 1293 | CA | ASN | A | 302 | −5.264 | 16.565 | −16.478 | 1.00 | 6.86 |
| ATOM | 1294 | CB | ASN | A | 302 | −6.387 | 17.163 | −15.567 | 1.00 | 7.92 |
| ATOM | 1295 | CG | ASN | A | 302 | −7.558 | 17.723 | −16.299 | 1.00 | 10.64 |
| ATOM | 1296 | OD1 | ASN | A | 302 | −7.501 | 17.998 | −17.461 | 1.00 | 12.43 |
| ATOM | 1297 | ND2 | ASN | A | 302 | −8.627 | 17.798 | −15.595 | 1.00 | 11.71 |
| ATOM | 1298 | C | ASN | A | 302 | −3.960 | 16.483 | −15.708 | 1.00 | 5.90 |
| ATOM | 1299 | O | ASN | A | 302 | −3.064 | 17.313 | −15.787 | 1.00 | 6.09 |
| ATOM | 1300 | N | ALA | A | 303 | −3.887 | 15.420 | −14.890 | 1.00 | 5.76 |
| ATOM | 1301 | CA | ALA | A | 303 | −2.657 | 15.183 | −14.093 | 1.00 | 5.36 |
| ATOM | 1302 | CB | ALA | A | 303 | −2.896 | 14.077 | −13.107 | 1.00 | 5.81 |
| ATOM | 1303 | C | ALA | A | 303 | −1.428 | 14.942 | −14.973 | 1.00 | 4.93 |
| ATOM | 1304 | O | ALA | A | 303 | −0.344 | 15.487 | −14.730 | 1.00 | 5.87 |
| ATOM | 1305 | N | ILE | A | 304 | −1.590 | 14.069 | −15.990 | 1.00 | 4.83 |
| ATOM | 1306 | CA | ILE | A | 304 | −0.550 | 13.806 | −16.933 | 1.00 | 5.22 |
| ATOM | 1307 | CB | ILE | A | 304 | −0.994 | 12.740 | −17.912 | 1.00 | 5.57 |
| ATOM | 1308 | CG1 | ILE | A | 304 | −1.111 | 11.406 | −17.157 | 1.00 | 6.10 |
| ATOM | 1309 | CD1 | ILE | A | 304 | −1.828 | 10.367 | −17.995 | 1.00 | 8.37 |
| ATOM | 1310 | CG2 | ILE | A | 304 | −0.095 | 12.628 | −19.142 | 1.00 | 5.77 |
| ATOM | 1311 | C | ILE | A | 304 | −0.099 | 15.100 | −17.634 | 1.00 | 5.29 |
| ATOM | 1312 | O | ILE | A | 304 | 1.084 | 15.298 | −17.837 | 1.00 | 5.61 |
| ATOM | 1313 | N | ASN | A | 305 | −1.087 | 15.923 | −18.047 | 1.00 | 5.61 |
| ATOM | 1314 | CA | ASN | A | 305 | −0.716 | 17.178 | −18.713 | 1.00 | 5.77 |
| ATOM | 1315 | CB | ASN | A | 305 | −1.967 | 17.881 | −19.159 | 1.00 | 6.64 |
| ATOM | 1316 | CG | ASN | A | 305 | −2.768 | 17.202 | −20.272 | 1.00 | 6.95 |
| ATOM | 1317 | OD1 | ASN | A | 305 | −2.271 | 16.312 | −20.956 | 1.00 | 9.05 |
| ATOM | 1318 | ND2 | ASN | A | 305 | −3.996 | 17.672 | −20.462 | 1.00 | 8.02 |
| ATOM | 1319 | C | ASN | A | 305 | 0.134 | 18.062 | −17.809 | 1.00 | 6.37 |
| ATOM | 1320 | O | ASN | A | 305 | 1.065 | 18.651 | −18.282 | 1.00 | 6.68 |
| ATOM | 1321 | N | THR | A | 306 | −0.255 | 18.131 | −16.562 | 1.00 | 5.52 |
| ATOM | 1322 | CA | THR | A | 306 | 0.506 | 18.859 | −15.564 | 1.00 | 6.89 |
| ATOM | 1323 | CB | THR | A | 306 | −0.171 | 18.851 | −14.208 | 1.00 | 8.46 |
| ATOM | 1324 | OG1 | THR | A | 306 | −1.363 | 19.694 | −14.327 | 1.00 | 13.62 |
| ATOM | 1325 | CG2 | THR | A | 306 | 0.677 | 19.375 | −13.089 | 1.00 | 9.84 |
| ATOM | 1326 | C | THR | A | 306 | 1.927 | 18.309 | −15.431 | 1.00 | 6.74 |
| ATOM | 1327 | O | THR | A | 306 | 2.940 | 19.039 | −15.483 | 1.00 | 6.54 |
| ATOM | 1328 | N | ALA | A | 307 | 2.039 | 16.969 | −15.269 | 1.00 | 5.72 |
| ATOM | 1329 | CA | ALA | A | 307 | 3.397 | 16.378 | −15.135 | 1.00 | 5.35 |
| ATOM | 1330 | CB | ALA | A | 307 | 3.250 | 14.875 | −14.941 | 1.00 | 6.32 |
| ATOM | 1331 | C | ALA | A | 307 | 4.266 | 16.693 | −16.339 | 1.00 | 5.04 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1332 | O | ALA | A | 307 | 5.444 | 17.110 | −16.226 | 1.00 | 5.83 |
| ATOM | 1333 | N | ARG | A | 308 | 3.708 | 16.497 | −17.551 | 1.00 | 5.47 |
| ATOM | 1334 | CA | ARG | A | 308 | 4.461 | 16.794 | −18.795 | 1.00 | 5.90 |
| ATOM | 1335 | CB | ARG | A | 308 | 3.599 | 16.473 | −20.010 | 1.00 | 6.22 |
| ATOM | 1336 | CG | ARG | A | 308 | 3.317 | 14.979 | −20.183 | 1.00 | 6.61 |
| ATOM | 1337 | CD | ARG | A | 308 | 2.259 | 14.780 | −21.218 | 1.00 | 7.12 |
| ATOM | 1338 | NE | ARG | A | 308 | 2.456 | 15.493 | −22.461 | 1.00 | 8.07 |
| ATOM | 1339 | CZ | ARG | A | 308 | 3.367 | 15.207 | −23.357 | 1.00 | 8.69 |
| ATOM | 1340 | NH1 | ARG | A | 308 | 4.056 | 14.111 | −23.272 | 1.00 | 8.42 |
| ATOM | 1341 | NH2 | ARG | A | 308 | 3.684 | 16.030 | −24.339 | 1.00 | 10.95 |
| ATOM | 1342 | C | ARG | A | 308 | 4.896 | 18.249 | −18.874 | 1.00 | 6.20 |
| ATOM | 1343 | O | ARG | A | 308 | 6.011 | 18.559 | −19.218 | 1.00 | 7.50 |
| ATOM | 1344 | N | SER | A | 309 | 4.010 | 19.135 | −18.400 | 1.00 | 6.49 |
| ATOM | 1345 | CA | SER | A | 309 | 4.311 | 20.632 | −18.474 | 1.00 | 7.46 |
| ATOM | 1346 | CB | SER | A | 309 | 3.065 | 21.377 | −18.074 | 1.00 | 9.00 |
| ATOM | 1347 | OG | SER | A | 309 | 2.768 | 21.369 | −16.677 | 1.00 | 12.74 |
| ATOM | 1348 | C | SER | A | 309 | 5.418 | 20.953 | −17.474 | 1.00 | 7.02 |
| ATOM | 1349 | O | SER | A | 309 | 6.176 | 21.940 | −17.651 | 1.00 | 8.86 |
| ATOM | 1350 | N | ASN | A | 310 | 5.570 | 20.149 | −16.413 | 1.00 | 6.46 |
| ATOM | 1351 | CA | ASN | A | 310 | 6.658 | 20.310 | −15.445 | 1.00 | 7.47 |
| ATOM | 1352 | CB | ASN | A | 310 | 6.181 | 19.813 | −14.090 | 1.00 | 8.11 |
| ATOM | 1353 | CG | ASN | A | 310 | 5.201 | 20.717 | −13.445 | 1.00 | 9.14 |
| ATOM | 1354 | OD1 | ASN | A | 310 | 5.203 | 21.951 | −13.765 | 1.00 | 11.68 |
| ATOM | 1355 | ND2 | ASN | A | 310 | 4.404 | 20.234 | −12.539 | 1.00 | 8.66 |
| ATOM | 1356 | C | ASN | A | 310 | 7.907 | 19.599 | −15.889 | 1.00 | 7.63 |
| ATOM | 1357 | O | ASN | A | 310 | 8.902 | 19.602 | −15.152 | 1.00 | 10.73 |
| ATOM | 1358 | N | GLY | A | 311 | 7.941 | 18.968 | −17.074 | 1.00 | 7.13 |
| ATOM | 1359 | CA | GLY | A | 311 | 9.152 | 18.388 | −17.626 | 1.00 | 7.00 |
| ATOM | 1360 | C | GLY | A | 311 | 9.249 | 16.892 | −17.370 | 1.00 | 6.93 |
| ATOM | 1361 | O | GLY | A | 311 | 10.332 | 16.301 | −17.617 | 1.00 | 10.07 |
| ATOM | 1362 | N | THR | A | 312 | 8.223 | 16.272 | −16.805 | 1.00 | 6.21 |
| ATOM | 1363 | CA | THR | A | 312 | 8.311 | 14.833 | −16.390 | 1.00 | 5.71 |
| ATOM | 1364 | CB | THR | A | 312 | 7.471 | 14.645 | −15.144 | 1.00 | 6.01 |
| ATOM | 1365 | OG1 | THR | A | 312 | 7.915 | 15.560 | −14.115 | 1.00 | 7.73 |
| ATOM | 1366 | CG2 | THR | A | 312 | 7.541 | 13.221 | −14.606 | 1.00 | 6.28 |
| ATOM | 1367 | C | THR | A | 312 | 7.733 | 13.959 | −17.484 | 1.00 | 5.44 |
| ATOM | 1368 | O | THR | A | 312 | 6.570 | 14.161 | −17.948 | 1.00 | 6.74 |
| ATOM | 1369 | N | VAL | A | 313 | 8.495 | 12.967 | −17.960 | 1.00 | 4.97 |
| ATOM | 1370 | CA | VAL | A | 313 | 8.008 | 11.932 | −18.874 | 1.00 | 5.06 |
| ATOM | 1371 | CB | VAL | A | 313 | 9.149 | 11.392 | −19.742 | 1.00 | 5.61 |
| ATOM | 1372 | CG1 | VAL | A | 313 | 10.143 | 10.576 | −18.946 | 1.00 | 5.33 |
| ATOM | 1373 | CG2 | VAL | A | 313 | 8.621 | 10.560 | −20.931 | 1.00 | 6.27 |
| ATOM | 1374 | C | VAL | A | 313 | 7.262 | 10.886 | −18.085 | 1.00 | 4.65 |
| ATOM | 1375 | O | VAL | A | 313 | 7.659 | 10.524 | −16.971 | 1.00 | 5.58 |
| ATOM | 1376 | N | VAL | A | 314 | 6.198 | 10.368 | −18.679 | 1.00 | 4.67 |
| ATOM | 1377 | CA | VAL | A | 314 | 5.283 | 9.436 | −17.993 | 1.00 | 4.36 |
| ATOM | 1378 | CB | VAL | A | 314 | 3.871 | 10.027 | −17.928 | 1.00 | 5.26 |
| ATOM | 1379 | CG1 | VAL | A | 314 | 2.969 | 9.092 | −17.155 | 1.00 | 6.38 |
| ATOM | 1380 | CG2 | VAL | A | 314 | 3.888 | 11.375 | −17.243 | 1.00 | 5.78 |
| ATOM | 1381 | C | VAL | A | 314 | 5.308 | 8.083 | −18.713 | 1.00 | 4.50 |
| ATOM | 1382 | O | VAL | A | 314 | 4.913 | 8.041 | −19.878 | 1.00 | 5.54 |
| ATOM | 1383 | N | VAL | A | 315 | 5.723 | 7.034 | −18.026 | 1.00 | 4.48 |
| ATOM | 1384 | CA | VAL | A | 315 | 5.864 | 5.697 | −18.561 | 1.00 | 4.66 |
| ATOM | 1385 | CB | VAL | A | 315 | 7.331 | 5.209 | −18.333 | 1.00 | 5.25 |
| ATOM | 1386 | CG1 | VAL | A | 315 | 7.495 | 3.800 | −18.906 | 1.00 | 5.92 |
| ATOM | 1387 | CG2 | VAL | A | 315 | 8.331 | 6.172 | −19.014 | 1.00 | 5.37 |
| ATOM | 1388 | C | VAL | A | 315 | 4.879 | 4.801 | −17.885 | 1.00 | 4.81 |
| ATOM | 1389 | O | VAL | A | 315 | 4.806 | 4.761 | −16.667 | 1.00 | 5.27 |
| ATOM | 1390 | N | ILE | A | 316 | 4.114 | 4.029 | −18.694 | 1.00 | 4.90 |
| ATOM | 1391 | CA | ILE | A | 316 | 2.950 | 3.299 | −18.197 | 1.00 | 4.70 |
| ATOM | 1392 | CB | ILE | A | 316 | 1.640 | 4.016 | −18.580 | 1.00 | 5.52 |
| ATOM | 1393 | CG1 | ILE | A | 316 | 1.716 | 5.459 | −18.054 | 1.00 | 6.42 |
| ATOM | 1394 | CD1 | ILE | A | 316 | 0.497 | 6.304 | −18.292 | 1.00 | 8.35 |
| ATOM | 1395 | CG2 | ILE | A | 316 | 0.449 | 3.256 | −18.009 | 1.00 | 6.28 |
| ATOM | 1396 | C | ILE | A | 316 | 2.925 | 1.882 | −18.763 | 1.00 | 4.57 |
| ATOM | 1397 | O | ILE | A | 316 | 3.269 | 1.623 | −19.921 | 1.00 | 5.52 |
| ATOM | 1398 | N | ALA | A | 317 | 2.570 | 0.936 | −17.888 | 1.00 | 3.86 |
| ATOM | 1399 | CA | ALA | A | 317 | 2.272 | −0.437 | −18.297 | 1.00 | 4.33 |
| ATOM | 1400 | CB | ALA | A | 317 | 2.171 | −1.307 | −17.094 | 1.00 | 4.61 |
| ATOM | 1401 | C | ALA | A | 317 | 0.986 | −0.541 | −19.071 | 1.00 | 5.00 |
| ATOM | 1402 | O | ALA | A | 317 | −0.059 | −0.077 | −18.632 | 1.00 | 6.34 |
| ATOM | 1403 | N | ALA | A | 318 | 1.023 | −1.256 | −20.211 | 1.00 | 4.73 |
| ATOM | 1404 | CA | ALA | A | 318 | −0.216 | −1.305 | −21.106 | 1.00 | 5.48 |
| ATOM | 1405 | CB | ALA | A | 318 | 0.198 | −1.737 | −22.482 | 1.00 | 6.17 |
| ATOM | 1406 | C | ALA | A | 318 | −1.235 | −2.202 | −20.593 | 1.00 | 5.66 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1407 | O | ALA | A | 318 | −2.423 | −2.128 | −21.118 | 1.00 | 6.82 |
| ATOM | 1408 | N | GLY | A | 319 | −0.996 | −3.077 | −19.640 | 1.00 | 5.02 |
| ATOM | 1409 | CA | GLY | A | 319 | −1.978 | −4.025 | −19.097 | 1.00 | 5.57 |
| ATOM | 1410 | C | GLY | A | 319 | −1.810 | −5.445 | −19.604 | 1.00 | 5.40 |
| ATOM | 1411 | O | GLY | A | 319 | −1.131 | −5.710 | −20.563 | 1.00 | 5.78 |
| ATOM | 1412 | N | ASN | A | 320 | −2.476 | −6.372 | −18.936 | 1.00 | 6.68 |
| ATOM | 1413 | CA | ASN | A | 320 | −2.191 | −7.812 | −18.983 | 1.00 | 7.71 |
| ATOM | 1414 | CB | ASN | A | 320 | −1.642 | −8.326 | −17.698 | 1.00 | 8.60 |
| ATOM | 1415 | CG | ASN | A | 320 | −0.449 | −7.538 | −17.205 | 1.00 | 10.07 |
| ATOM | 1416 | OD1 | ASN | A | 320 | 0.421 | −7.027 | −17.972 | 1.00 | 8.35 |
| ATOM | 1417 | ND2 | ASN | A | 320 | −0.340 | −7.442 | −15.900 | 1.00 | 13.88 |
| ATOM | 1418 | C | ASN | A | 320 | −3.426 | −8.618 | −19.368 | 1.00 | 8.66 |
| ATOM | 1419 | O | ASN | A | 320 | −3.589 | −9.739 | −18.876 | 1.00 | 10.16 |
| ATOM | 1420 | N | ASP | A | 321 | −4.238 | −8.089 | −20.231 | 1.00 | 7.49 |
| ATOM | 1421 | CA | ASP | A | 321 | −5.531 | −8.706 | −20.616 | 1.00 | 9.71 |
| ATOM | 1422 | CB | ASP | A | 321 | −6.569 | −7.538 | −20.641 | 1.00 | 11.83 |
| ATOM | 1423 | CG | ASP | A | 321 | −6.378 | −6.550 | −19.371 | 1.00 | 15.03 |
| ATOM | 1424 | OD1 | ASP | A | 321 | −7.039 | −6.989 | −18.395 | 1.00 | 16.94 |
| ATOM | 1425 | OD2 | ASP | A | 321 | −5.644 | −5.424 | −19.304 | 1.00 | 16.25 |
| ATOM | 1426 | C | ASP | A | 321 | −5.435 | −9.406 | −21.926 | 1.00 | 8.14 |
| ATOM | 1427 | O | ASP | A | 321 | −6.492 | −9.867 | −22.471 | 1.00 | 9.13 |
| ATOM | 1428 | N | ASN | A | 322 | −4.316 | −9.500 | −22.626 | 1.00 | 6.51 |
| ATOM | 1429 | CA | ASN | A | 322 | −4.212 | −10.052 | −23.936 | 1.00 | 6.61 |
| ATOM | 1430 | CB | ASN | A | 322 | −4.312 | −11.592 | −23.964 | 1.00 | 7.14 |
| ATOM | 1431 | CG | ASN | A | 322 | −4.082 | −12.168 | −25.290 | 1.00 | 7.15 |
| ATOM | 1432 | OD1 | ASN | A | 322 | −3.359 | −11.705 | −26.143 | 1.00 | 8.73 |
| ATOM | 1433 | ND2 | ASN | A | 322 | −4.772 | −13.340 | −25.552 | 1.00 | 8.38 |
| ATOM | 1434 | C | ASN | A | 322 | −5.302 | −9.416 | −24.786 | 1.00 | 7.81 |
| ATOM | 1435 | O | ASN | A | 322 | −5.985 | −10.144 | −25.583 | 1.00 | 8.91 |
| ATOM | 1436 | N | ASP | A | 323 | −5.384 | −8.091 | −24.774 | 1.00 | 7.92 |
| ATOM | 1437 | CA | ASP | A | 323 | −6.486 | −7.430 | −25.450 | 1.00 | 9.18 |
| ATOM | 1438 | CB | ASP | A | 323 | −7.615 | −7.221 | −24.435 | 1.00 | 9.74 |
| ATOM | 1439 | CG | ASP | A | 323 | −9.003 | −6.817 | −25.038 | 1.00 | 12.12 |
| ATOM | 1440 | OD1 | ASP | A | 323 | −9.199 | −6.968 | −26.214 | 1.00 | 13.77 |
| ATOM | 1441 | OD2 | ASP | A | 323 | −9.741 | −6.391 | −24.141 | 1.00 | 16.14 |
| ATOM | 1442 | C | ASP | A | 323 | −5.954 | −6.124 | −26.007 | 1.00 | 9.00 |
| ATOM | 1443 | O | ASP | A | 323 | −4.826 | −5.689 | −25.817 | 1.00 | 8.00 |
| ATOM | 1444 | N | ASN | A | 324 | −6.833 | −5.409 | −26.686 | 1.00 | 9.69 |
| ATOM | 1445 | CA | ASN | A | 324 | −6.516 | −4.107 | −27.317 | 1.00 | 9.55 |
| ATOM | 1446 | CB | ASN | A | 324 | −7.718 | −3.692 | −28.195 | 1.00 | 11.03 |
| ATOM | 1447 | CG | ASN | A | 324 | −7.567 | −2.404 | −28.942 | 1.00 | 14.91 |
| ATOM | 1448 | OD1 | ASN | A | 324 | −6.586 | −1.707 | −28.829 | 1.00 | 12.45 |
| ATOM | 1449 | ND2 | ASN | A | 324 | −8.596 | −2.105 | −29.762 | 1.00 | 17.83 |
| ATOM | 1450 | C | ASN | A | 324 | −6.290 | −3.045 | −26.281 | 1.00 | 8.72 |
| ATOM | 1451 | O | ASN | A | 324 | −7.102 | −2.666 | −25.433 | 1.00 | 9.67 |
| ATOM | 1452 | N | SER | A | 325 | −5.085 | −2.481 | −26.295 | 1.00 | 7.76 |
| ATOM | 1453 | CA | SER | A | 325 | −4.607 | −1.492 | −25.358 | 1.00 | 8.88 |
| ATOM | 1454 | CB | SER | A | 325 | −3.106 | −1.303 | −25.592 | 1.00 | 9.29 |
| ATOM | 1455 | OG | SER | A | 325 | −2.837 | −0.855 | −26.892 | 1.00 | 10.13 |
| ATOM | 1456 | C | SER | A | 325 | −5.345 | −0.170 | −25.430 | 1.00 | 9.62 |
| ATOM | 1457 | O | SER | A | 325 | −5.275 | 0.578 | −24.498 | 1.00 | 10.18 |
| ATOM | 1458 | N | ALA | A | 326 | −6.131 | 0.027 | −26.489 | 1.00 | 9.81 |
| ATOM | 1459 | CA | ALA | A | 326 | −7.021 | 1.216 | −26.567 | 1.00 | 9.49 |
| ATOM | 1460 | CB | ALA | A | 326 | −7.857 | 1.151 | −27.853 | 1.00 | 11.34 |
| ATOM | 1461 | C | ALA | A | 326 | −7.946 | 1.287 | −25.430 | 1.00 | 9.35 |
| ATOM | 1462 | O | ALA | A | 326 | −8.411 | 2.359 | −25.039 | 1.00 | 9.59 |
| ATOM | 1463 | N | ASN | A | 327 | −8.277 | 0.161 | −24.792 | 1.00 | 9.32 |
| ATOM | 1464 | CA | ASN | A | 327 | −9.306 | 0.114 | −23.811 | 1.00 | 10.59 |
| ATOM | 1465 | CB | ASN | A | 327 | −10.310 | −0.955 | −24.250 | 1.00 | 14.30 |
| ATOM | 1466 | CG | ASN | A | 327 | −10.933 | −0.581 | −25.618 | 1.00 | 17.57 |
| ATOM | 1467 | OD1 | ASN | A | 327 | −11.244 | 0.620 | −25.877 | 1.00 | 20.41 |
| ATOM | 1468 | ND2 | ASN | A | 327 | −11.070 | −1.541 | −26.436 | 1.00 | 21.91 |
| ATOM | 1469 | C | ASN | A | 327 | −8.919 | −0.099 | −22.385 | 1.00 | 9.65 |
| ATOM | 1470 | O | ASN | A | 327 | −9.694 | −0.446 | −21.519 | 1.00 | 9.83 |
| ATOM | 1471 | N | TYR | A | 328 | −7.666 | 0.272 | −22.093 | 1.00 | 7.86 |
| ATOM | 1472 | CA | TYR | A | 328 | −7.044 | 0.097 | −20.811 | 1.00 | 7.81 |
| ATOM | 1473 | CB | TYR | A | 328 | −6.128 | −1.134 | −20.761 | 1.00 | 9.19 |
| ATOM | 1474 | CG | TYR | A | 328 | −6.908 | −2.396 | −20.972 | 1.00 | 9.72 |
| ATOM | 1475 | CD1 | TYR | A | 328 | −7.608 | −2.989 | −19.926 | 1.00 | 11.80 |
| ATOM | 1476 | CE1 | TYR | A | 328 | −8.431 | −4.102 | −20.184 | 1.00 | 12.69 |
| ATOM | 1477 | CZ | TYR | A | 328 | −8.561 | −4.560 | −21.406 | 1.00 | 11.69 |
| ATOM | 1478 | OH | TYR | A | 328 | −9.343 | −5.726 | −21.605 | 1.00 | 14.32 |
| ATOM | 1479 | CE2 | TYR | A | 328 | −7.984 | −3.990 | −22.483 | 1.00 | 11.45 |
| ATOM | 1480 | CD2 | TYR | A | 328 | −7.148 | −2.886 | −22.214 | 1.00 | 10.35 |
| ATOM | 1481 | C | TYR | A | 328 | −6.290 | 1.396 | −20.433 | 1.00 | 7.90 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1482 | O | TYR | A | 328 | −5.498 | 1.895 | −21.218 | 1.00 | 7.66 |
| ATOM | 1483 | N | ASN | A | 329 | −6.609 | 1.899 | −19.270 | 1.00 | 8.30 |
| ATOM | 1484 | CA | ASN | A | 329 | −6.059 | 3.156 | −18.757 | 1.00 | 8.15 |
| ATOM | 1485 | CB | ASN | A | 329 | −7.231 | 4.096 | −18.249 | 1.00 | 8.84 |
| ATOM | 1486 | CG | ASN | A | 329 | −7.991 | 3.505 | −17.140 | 1.00 | 12.04 |
| ATOM | 1487 | OD1 | ASN | A | 329 | −7.583 | 3.534 | −16.014 | 1.00 | 14.73 |
| ATOM | 1488 | ND2 | ASN | A | 329 | −9.070 | 2.904 | −17.451 | 1.00 | 12.11 |
| ATOM | 1489 | C | ASN | A | 329 | −5.044 | 2.889 | −17.649 | 1.00 | 8.51 |
| ATOM | 1490 | O | ASN | A | 329 | −5.195 | 1.845 | −16.958 | 1.00 | 10.32 |
| ATOM | 1491 | N | PRO | A | 330 | −4.121 | 3.756 | −17.334 | 1.00 | 8.01 |
| ATOM | 1492 | CA | PRO | A | 330 | −3.885 | 5.035 | −18.023 | 1.00 | 7.20 |
| ATOM | 1493 | CB | PRO | A | 330 | −3.242 | 5.881 | −16.928 | 1.00 | 7.49 |
| ATOM | 1494 | CG | PRO | A | 330 | −2.477 | 4.873 | −16.070 | 1.00 | 8.85 |
| ATOM | 1495 | CD | PRO | A | 330 | −3.350 | 3.633 | −16.077 | 1.00 | 9.41 |
| ATOM | 1496 | C | PRO | A | 330 | −2.998 | 4.915 | −19.247 | 1.00 | 6.48 |
| ATOM | 1497 | O | PRO | A | 330 | −2.652 | 5.928 | −19.852 | 1.00 | 6.33 |
| ATOM | 1498 | N | GLY | A | 331 | −2.705 | 3.706 | −19.732 | 1.00 | 6.43 |
| ATOM | 1499 | CA | GLY | A | 331 | −1.905 | 3.608 | −20.881 | 1.00 | 7.08 |
| ATOM | 1500 | C | GLY | A | 331 | −2.476 | 4.199 | −22.150 | 1.00 | 7.24 |
| ATOM | 1501 | O | GLY | A | 331 | −1.780 | 4.590 | −23.070 | 1.00 | 8.74 |
| ATOM | 1502 | N | ASN | A | 332 | −3.824 | 4.242 | −22.211 | 1.00 | 7.21 |
| ATOM | 1503 | CA | ASN | A | 332 | −4.584 | 4.885 | −23.279 | 1.00 | 6.98 |
| ATOM | 1504 | CB | ASN | A | 332 | −5.918 | 4.176 | −23.473 | 1.00 | 6.72 |
| ATOM | 1505 | CG | ASN | A | 332 | −6.839 | 4.336 | −22.307 | 1.00 | 6.75 |
| ATOM | 1506 | OD1 | ASN | A | 332 | −6.509 | 4.970 | −21.310 | 1.00 | 7.09 |
| ATOM | 1507 | ND2 | ASN | A | 332 | −8.046 | 3.759 | −22.400 | 1.00 | 7.72 |
| ATOM | 1508 | C | ASN | A | 332 | −4.725 | 6.366 | −23.124 | 1.00 | 7.68 |
| ATOM | 1509 | O | ASN | A | 332 | −5.337 | 7.000 | −24.009 | 1.00 | 9.61 |
| ATOM | 1510 | N | CYS | A | 333 | −4.098 | 6.973 | −22.131 | 1.00 | 6.78 |
| ATOM | 1511 | CA | CYS | A | 333 | −4.102 | 8.444 | −22.043 | 1.00 | 6.97 |
| ATOM | 1512 | CB | CYS | A | 333 | −3.637 | 8.849 | −20.688 | 1.00 | 6.66 |
| ATOM | 1513 | SG | CYS | A | 333 | −4.699 | 8.310 | −19.333 | 1.00 | 8.62 |
| ATOM | 1514 | C | CYS | A | 333 | −3.163 | 8.966 | −23.106 | 1.00 | 6.49 |
| ATOM | 1515 | O | CYS | A | 333 | −2.347 | 8.283 | −23.739 | 1.00 | 7.78 |
| ATOM | 1516 | N | ASN | A | 334 | −3.266 | 10.264 | −23.440 | 1.00 | 6.48 |
| ATOM | 1517 | CA | ASN | A | 334 | −2.400 | 10.935 | −24.363 | 1.00 | 6.14 |
| ATOM | 1518 | CB | ASN | A | 334 | −3.094 | 12.027 | −25.154 | 1.00 | 7.05 |
| ATOM | 1519 | CG | ASN | A | 334 | −4.204 | 11.493 | −26.001 | 1.00 | 9.21 |
| ATOM | 1520 | OD1 | ASN | A | 334 | −3.985 | 10.511 | −26.724 | 1.00 | 12.82 |
| ATOM | 1521 | ND2 | ASN | A | 334 | −5.355 | 12.021 | −25.894 | 1.00 | 10.07 |
| ATOM | 1522 | C | ASN | A | 334 | −1.150 | 11.459 | −23.666 | 1.00 | 5.19 |
| ATOM | 1523 | O | ASN | A | 334 | −1.198 | 11.821 | −22.487 | 1.00 | 6.15 |
| ATOM | 1524 | N | GLY | A | 335 | −0.060 | 11.529 | −24.412 | 1.00 | 4.99 |
| ATOM | 1525 | CA | GLY | A | 335 | 1.206 | 12.057 | −23.884 | 1.00 | 5.47 |
| ATOM | 1526 | C | GLY | A | 335 | 1.968 | 11.159 | −22.959 | 1.00 | 6.11 |
| ATOM | 1527 | O | GLY | A | 335 | 2.698 | 11.671 | −22.114 | 1.00 | 6.82 |
| ATOM | 1528 | N | VAL | A | 336 | 1.829 | 9.839 | −23.139 | 1.00 | 5.58 |
| ATOM | 1529 | CA | VAL | A | 336 | 2.495 | 8.867 | −22.287 | 1.00 | 5.14 |
| ATOM | 1530 | CB | VAL | A | 336 | 1.476 | 8.112 | −21.388 | 1.00 | 5.83 |
| ATOM | 1531 | CG1 | VAL | A | 336 | 0.588 | 9.068 | −20.579 | 1.00 | 6.64 |
| ATOM | 1532 | CG2 | VAL | A | 336 | 0.593 | 7.162 | −22.146 | 1.00 | 7.05 |
| ATOM | 1533 | C | VAL | A | 336 | 3.267 | 7.923 | −23.121 | 1.00 | 5.06 |
| ATOM | 1534 | O | VAL | A | 336 | 2.993 | 7.730 | −24.311 | 1.00 | 5.59 |
| ATOM | 1535 | N | VAL | A | 337 | 4.219 | 7.239 | −22.493 | 1.00 | 4.68 |
| ATOM | 1536 | CA | VAL | A | 337 | 4.959 | 6.131 | −23.132 | 1.00 | 5.01 |
| ATOM | 1537 | CB | VAL | A | 337 | 6.438 | 6.150 | −22.796 | 1.00 | 5.68 |
| ATOM | 1538 | CG1 | VAL | A | 337 | 7.170 | 5.087 | −23.515 | 1.00 | 6.36 |
| ATOM | 1539 | CG2 | VAL | A | 337 | 7.054 | 7.547 | −23.050 | 1.00 | 6.32 |
| ATOM | 1540 | C | VAL | A | 337 | 4.308 | 4.836 | −22.657 | 1.00 | 4.74 |
| ATOM | 1541 | O | VAL | A | 337 | 4.492 | 4.438 | −21.489 | 1.00 | 4.49 |
| ATOM | 1542 | N | ASN | A | 338 | 3.515 | 4.207 | −23.512 | 1.00 | 4.54 |
| ATOM | 1543 | CA | ASN | A | 338 | 2.754 | 3.016 | −23.149 | 1.00 | 4.70 |
| ATOM | 1544 | CB | ASN | A | 338 | 1.361 | 3.031 | −23.774 | 1.00 | 5.18 |
| ATOM | 1545 | CG | ASN | A | 338 | 0.442 | 2.043 | −23.130 | 1.00 | 6.18 |
| ATOM | 1546 | OD1 | ASN | A | 338 | 0.572 | 1.674 | −22.000 | 1.00 | 6.42 |
| ATOM | 1547 | ND2 | ASN | A | 338 | −0.597 | 1.626 | −23.907 | 1.00 | 7.16 |
| ATOM | 1548 | C | ASN | A | 338 | 3.517 | 1.799 | −23.608 | 1.00 | 4.85 |
| ATOM | 1549 | O | ASN | A | 338 | 3.987 | 1.717 | −24.771 | 1.00 | 5.38 |
| ATOM | 1550 | N | VAL | A | 339 | 3.701 | 0.865 | −22.672 | 1.00 | 4.31 |
| ATOM | 1551 | CA | VAL | A | 339 | 4.721 | −0.207 | −22.825 | 1.00 | 4.83 |
| ATOM | 1552 | CB | VAL | A | 339 | 5.724 | −0.114 | −21.673 | 1.00 | 4.41 |
| ATOM | 1553 | CG1 | VAL | A | 339 | 6.798 | −1.201 | −21.814 | 1.00 | 4.27 |
| ATOM | 1554 | CG2 | VAL | A | 339 | 6.369 | 1.265 | −21.631 | 1.00 | 4.86 |
| ATOM | 1555 | C | VAL | A | 339 | 4.066 | −1.580 | −22.810 | 1.00 | 4.15 |
| ATOM | 1556 | O | VAL | A | 339 | 3.390 | −1.965 | −21.847 | 1.00 | 5.14 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1557 | N | GLY | A | 340 | 4.309 | −2.323 | −23.918 | 1.00 | 4.14 |
| ATOM | 1558 | CA | GLY | A | 340 | 3.946 | −3.754 | −23.984 | 1.00 | 4.32 |
| ATOM | 1559 | C | GLY | A | 340 | 5.086 | −4.592 | −23.475 | 1.00 | 5.09 |
| ATOM | 1560 | O | GLY | A | 340 | 6.233 | −4.182 | −23.361 | 1.00 | 5.27 |
| ATOM | 1561 | N | SER | A | 341 | 4.789 | −5.865 | −23.154 | 1.00 | 4.87 |
| ATOM | 1562 | CA | SER | A | 341 | 5.745 | −6.772 | −22.570 | 1.00 | 4.72 |
| ATOM | 1563 | CB | SER | A | 341 | 5.134 | −7.431 | −21.362 | 1.00 | 5.28 |
| ATOM | 1564 | OG | SER | A | 341 | 6.007 | −8.451 | −20.867 | 1.00 | 5.47 |
| ATOM | 1565 | C | SER | A | 341 | 6.183 | −7.864 | −23.510 | 1.00 | 4.95 |
| ATOM | 1566 | O | SER | A | 341 | 5.275 | −8.491 | −24.153 | 1.00 | 5.74 |
| ATOM | 1567 | N | VAL | A | 342 | 7.463 | −8.123 | −23.632 | 1.00 | 4.86 |
| ATOM | 1568 | CA | VAL | A | 342 | 8.007 | −9.324 | −24.246 | 1.00 | 4.81 |
| ATOM | 1569 | CB | VAL | A | 342 | 9.097 | −9.062 | −25.282 | 1.00 | 5.65 |
| ATOM | 1570 | CG1 | VAL | A | 342 | 8.540 | −8.234 | −26.457 | 1.00 | 6.42 |
| ATOM | 1571 | CG2 | VAL | A | 342 | 10.325 | −8.396 | −24.683 | 1.00 | 5.90 |
| ATOM | 1572 | C | VAL | A | 342 | 8.475 | −10.276 | −23.214 | 1.00 | 5.27 |
| ATOM | 1573 | O | VAL | A | 342 | 8.895 | −9.939 | −22.086 | 1.00 | 5.26 |
| ATOM | 1574 | N | GLY | A | 343 | 8.481 | −11.554 | −23.586 | 1.00 | 5.24 |
| ATOM | 1575 | CA | GLY | A | 343 | 9.146 | −12.606 | −22.776 | 1.00 | 5.76 |
| ATOM | 1576 | C | GLY | A | 343 | 10.573 | −12.750 | −23.153 | 1.00 | 5.22 |
| ATOM | 1577 | O | GLY | A | 343 | 11.144 | −12.075 | −24.002 | 1.00 | 5.70 |
| ATOM | 1578 | N | ARG | A | 344 | 11.204 | −13.785 | −22.577 | 1.00 | 5.72 |
| ATOM | 1579 | CA | ARG | A | 344 | 12.584 | −14.124 | −22.810 | 1.00 | 6.92 |
| ATOM | 1580 | CB | ARG | A | 344 | 12.983 | −15.203 | −21.776 | 1.00 | 6.66 |
| ATOM | 1581 | CG | ARG | A | 344 | 14.487 | −15.473 | −21.757 | 1.00 | 7.10 |
| ATOM | 1582 | CD | ARG | A | 344 | 14.804 | −16.311 | −20.525 | 1.00 | 8.76 |
| ATOM | 1583 | NE | ARG | A | 344 | 16.241 | −16.486 | −20.323 | 1.00 | 9.16 |
| ATOM | 1584 | CZ | ARG | A | 344 | 16.700 | −17.083 | −19.207 | 1.00 | 11.98 |
| ATOM | 1585 | NH1 | ARG | A | 344 | 15.878 | −17.579 | −18.309 | 1.00 | 12.37 |
| ATOM | 1586 | NH2 | ARG | A | 344 | 17.984 | −17.008 | −18.972 | 1.00 | 14.02 |
| ATOM | 1587 | C | ARG | A | 344 | 12.881 | −14.510 | −24.255 | 1.00 | 6.39 |
| ATOM | 1588 | O | ARG | A | 344 | 14.015 | −14.419 | −24.677 | 1.00 | 7.27 |
| ATOM | 1589 | N | ASN | A | 345 | 11.867 | −14.912 | −25.008 | 1.00 | 6.91 |
| ATOM | 1590 | CA | ASN | A | 345 | 12.026 | −15.143 | −26.417 | 1.00 | 7.10 |
| ATOM | 1591 | CB | ASN | A | 345 | 10.923 | −16.094 | −27.005 | 1.00 | 8.01 |
| ATOM | 1592 | CG | ASN | A | 345 | 9.509 | −15.493 | −26.923 | 1.00 | 8.93 |
| ATOM | 1593 | OD1 | ASN | A | 345 | 8.597 | −15.938 | −27.694 | 1.00 | 14.51 |
| ATOM | 1594 | ND2 | ASN | A | 345 | 9.305 | −14.485 | −26.190 | 1.00 | 6.88 |
| ATOM | 1595 | C | ASN | A | 345 | 12.074 | −13.886 | −27.277 | 1.00 | 7.36 |
| ATOM | 1596 | O | ASN | A | 345 | 12.341 | −13.961 | −28.459 | 1.00 | 7.72 |
| ATOM | 1597 | N | GLY | A | 346 | 11.806 | −12.700 | −26.691 | 1.00 | 6.37 |
| ATOM | 1598 | CA | GLY | A | 346 | 11.714 | −11.502 | −27.478 | 1.00 | 6.55 |
| ATOM | 1599 | C | GLY | A | 346 | 10.430 | −11.363 | −28.298 | 1.00 | 6.47 |
| ATOM | 1600 | O | GLY | A | 346 | 10.412 | −10.466 | −29.170 | 1.00 | 8.14 |
| ATOM | 1601 | N | GLY | A | 347 | 9.454 | −12.147 | −28.015 | 1.00 | 6.60 |
| ATOM | 1602 | CA | GLY | A | 347 | 8.131 | −12.002 | −28.584 | 1.00 | 6.68 |
| ATOM | 1603 | C | GLY | A | 347 | 7.151 | −11.565 | −27.560 | 1.00 | 6.36 |
| ATOM | 1604 | O | GLY | A | 347 | 7.410 | −11.609 | −26.356 | 1.00 | 6.30 |
| ATOM | 1605 | N | ARG | A | 348 | 5.921 | −11.261 | −28.009 | 1.00 | 6.37 |
| ATOM | 1606 | CA | ARG | A | 348 | 4.936 | −10.747 | −27.092 | 1.00 | 5.68 |
| ATOM | 1607 | CB | ARG | A | 348 | 3.579 | −10.458 | −27.811 | 1.00 | 6.39 |
| ATOM | 1608 | CG | ARG | A | 348 | 2.643 | −9.668 | −26.939 | 1.00 | 6.99 |
| ATOM | 1609 | CD | ARG | A | 348 | 1.437 | −9.176 | −27.719 | 1.00 | 7.49 |
| ATOM | 1610 | NE | ARG | A | 348 | 0.618 | −10.240 | −28.281 | 1.00 | 7.26 |
| ATOM | 1611 | CZ | ARG | A | 348 | −0.299 | −10.954 | −27.678 | 1.00 | 8.60 |
| ATOM | 1612 | NH1 | ARG | A | 348 | −0.680 | −10.751 | −26.466 | 1.00 | 8.08 |
| ATOM | 1613 | NH2 | ARG | A | 348 | −0.985 | −11.861 | −28.441 | 1.00 | 12.89 |
| ATOM | 1614 | C | ARG | A | 348 | 4.700 | −11.677 | −25.949 | 1.00 | 5.83 |
| ATOM | 1615 | O | ARG | A | 348 | 4.432 | −12.890 | −26.126 | 1.00 | 8.22 |
| ATOM | 1616 | N | ALA | A | 349 | 4.730 | −11.238 | −24.714 | 1.00 | 5.39 |
| ATOM | 1617 | CA | ALA | A | 349 | 4.322 | −12.074 | −23.592 | 1.00 | 5.89 |
| ATOM | 1618 | CB | ALA | A | 349 | 4.628 | −11.326 | −22.268 | 1.00 | 5.69 |
| ATOM | 1619 | C | ALA | A | 349 | 2.875 | −12.383 | −23.725 | 1.00 | 6.58 |
| ATOM | 1620 | O | ALA | A | 349 | 2.081 | −11.538 | −24.097 | 1.00 | 7.04 |
| ATOM | 1621 | N | TYR | A | 350 | 2.476 | −13.620 | −23.386 | 1.00 | 7.05 |
| ATOM | 1622 | CA | TYR | A | 350 | 1.125 | −14.098 | −23.715 | 1.00 | 6.47 |
| ATOM | 1623 | CB | TYR | A | 350 | 0.918 | −15.524 | −23.199 | 1.00 | 6.57 |
| ATOM | 1624 | CG | TYR | A | 350 | 1.144 | −15.738 | −21.732 | 1.00 | 6.61 |
| ATOM | 1625 | CD1 | TYR | A | 350 | 0.129 | −15.593 | −20.800 | 1.00 | 7.23 |
| ATOM | 1626 | CE1 | TYR | A | 350 | 0.326 | −15.829 | −19.472 | 1.00 | 7.00 |
| ATOM | 1627 | CZ | TYR | A | 350 | 1.600 | −16.245 | −19.012 | 1.00 | 7.54 |
| ATOM | 1628 | OH | TYR | A | 350 | 1.714 | −16.524 | −17.630 | 1.00 | 10.10 |
| ATOM | 1629 | CE2 | TYR | A | 350 | 2.620 | −16.357 | −19.917 | 1.00 | 6.84 |
| ATOM | 1630 | CD2 | TYR | A | 350 | 2.419 | −16.104 | −21.216 | 1.00 | 7.27 |
| ATOM | 1631 | C | TYR | A | 350 | 0.047 | −13.202 | −23.190 | 1.00 | 6.81 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1632 | O | TYR | A | 350 | −1.035 | −13.102 | −23.808 | 1.00 | 8.05 |
| ATOM | 1633 | N | TYR | A | 351 | 0.209 | −12.555 | −22.043 | 1.00 | 5.85 |
| ATOM | 1634 | CA | TYR | A | 351 | −0.812 | −11.744 | −21.414 | 1.00 | 6.56 |
| ATOM | 1635 | CB | TYR | A | 351 | −0.603 | −11.743 | −19.855 | 1.00 | 6.50 |
| ATOM | 1636 | CG | TYR | A | 351 | 0.802 | −11.279 | −19.504 | 1.00 | 5.99 |
| ATOM | 1637 | CD1 | TYR | A | 351 | 1.157 | −9.936 | −19.582 | 1.00 | 6.08 |
| ATOM | 1638 | CE1 | TYR | A | 351 | 2.462 | −9.538 | −19.385 | 1.00 | 5.14 |
| ATOM | 1639 | CZ | TYR | A | 351 | 3.472 | −10.487 | −19.128 | 1.00 | 5.18 |
| ATOM | 1640 | OH | TYR | A | 351 | 4.758 | −10.041 | −18.946 | 1.00 | 5.21 |
| ATOM | 1641 | CE2 | TYR | A | 351 | 3.110 | −11.788 | −18.970 | 1.00 | 5.45 |
| ATOM | 1642 | CD2 | TYR | A | 351 | 1.838 | −12.173 | −19.181 | 1.00 | 5.78 |
| ATOM | 1643 | C | TYR | A | 351 | −0.781 | −10.275 | −21.917 | 1.00 | 5.57 |
| ATOM | 1644 | O | TYR | A | 351 | −1.670 | −9.539 | −21.504 | 1.00 | 6.66 |
| ATOM | 1645 | N | SER | A | 352 | 0.235 | −9.869 | −22.644 | 1.00 | 5.60 |
| ATOM | 1646 | CA | SER | A | 352 | 0.379 | −8.438 | −22.835 | 1.00 | 6.09 |
| ATOM | 1647 | CB | SER | A | 352 | 1.690 | −8.199 | −23.546 | 1.00 | 5.75 |
| ATOM | 1648 | OG | SER | A | 352 | 1.921 | −6.739 | −23.614 | 1.00 | 5.93 |
| ATOM | 1649 | C | SER | A | 352 | −0.718 | −7.894 | −23.709 | 1.00 | 5.48 |
| ATOM | 1650 | O | SER | A | 352 | −1.043 | −8.423 | −24.791 | 1.00 | 6.27 |
| ATOM | 1651 | N | ASN | A | 353 | −1.241 | −6.739 | −23.338 | 1.00 | 5.46 |
| ATOM | 1652 | CA | ASN | A | 353 | −2.035 | −5.940 | −24.260 | 1.00 | 5.50 |
| ATOM | 1653 | CB | ASN | A | 353 | −2.743 | −4.820 | −23.516 | 1.00 | 6.24 |
| ATOM | 1654 | CG | ASN | A | 353 | −3.818 | −5.262 | −22.590 | 1.00 | 6.96 |
| ATOM | 1655 | OD1 | ASN | A | 353 | −4.342 | −6.380 | −22.661 | 1.00 | 8.00 |
| ATOM | 1656 | ND2 | ASN | A | 353 | −4.173 | −4.401 | −21.645 | 1.00 | 6.15 |
| ATOM | 1657 | C | ASN | A | 353 | −1.214 | −5.471 | −25.408 | 1.00 | 6.48 |
| ATOM | 1658 | O | ASN | A | 353 | 0.038 | −5.473 | −25.368 | 1.00 | 6.94 |
| ATOM | 1659 | N | TYR | A | 354 | −1.906 | −5.035 | −26.440 | 1.00 | 6.28 |
| ATOM | 1660 | CA | TYR | A | 354 | −1.262 | −4.695 | −27.719 | 1.00 | 6.32 |
| ATOM | 1661 | CB | TYR | A | 354 | −0.929 | −5.972 | −28.533 | 1.00 | 8.02 |
| ATOM | 1662 | CG | TYR | A | 354 | −2.113 | −6.796 | −28.832 | 1.00 | 10.87 |
| ATOM | 1663 | CD1 | TYR | A | 354 | −3.109 | −6.409 | −29.810 | 1.00 | 15.69 |
| ATOM | 1664 | CE1 | TYR | A | 354 | −4.329 | −7.113 | −29.966 | 1.00 | 19.53 |
| ATOM | 1665 | CZ | TYR | A | 354 | −4.570 | −8.197 | −29.068 | 1.00 | 18.06 |
| ATOM | 1666 | OH | TYR | A | 354 | −5.770 | −8.939 | −29.168 | 1.00 | 22.96 |
| ATOM | 1667 | CE2 | TYR | A | 354 | −3.617 | −8.632 | −28.175 | 1.00 | 13.59 |
| ATOM | 1668 | CD2 | TYR | A | 354 | −2.472 | −7.850 | −27.987 | 1.00 | 9.66 |
| ATOM | 1669 | C | TYR | A | 354 | −2.205 | −3.773 | −28.510 | 1.00 | 6.17 |
| ATOM | 1670 | O | TYR | A | 354 | −3.396 | −3.803 | −28.185 | 1.00 | 8.17 |
| ATOM | 1671 | N | GLY | A | 355 | −1.696 | −3.024 | −29.434 | 1.00 | 6.53 |
| ATOM | 1672 | CA | GLY | A | 355 | −2.549 | −2.075 | −30.199 | 1.00 | 7.00 |
| ATOM | 1673 | C | GLY | A | 355 | −1.788 | −0.900 | −30.644 | 1.00 | 7.60 |
| ATOM | 1674 | O | GLY | A | 355 | −0.564 | −0.745 | −30.394 | 1.00 | 7.20 |
| ATOM | 1675 | N | SER | A | 356 | −2.509 | 0.004 | −31.317 | 1.00 | 8.55 |
| ATOM | 1676 | CA | SER | A | 356 | −1.895 | 1.157 | −31.891 | 1.00 | 9.15 |
| ATOM | 1677 | CB | SER | A | 356 | −2.947 | 1.946 | −32.736 | 1.00 | 13.62 |
| ATOM | 1678 | OG | SER | A | 356 | −3.589 | 1.071 | −33.656 | 1.00 | 25.87 |
| ATOM | 1679 | C | SER | A | 356 | −1.269 | 2.133 | −30.909 | 1.00 | 7.65 |
| ATOM | 1680 | O | SER | A | 356 | −0.269 | 2.762 | −31.266 | 1.00 | 8.60 |
| ATOM | 1681 | N | ASN | A | 357 | −1.766 | 2.199 | −29.699 | 1.00 | 6.38 |
| ATOM | 1682 | CA | ASN | A | 357 | −1.252 | 3.128 | −28.763 | 1.00 | 6.67 |
| ATOM | 1683 | CB | ASN | A | 357 | −2.289 | 3.679 | −27.810 | 1.00 | 6.94 |
| ATOM | 1684 | CG | ASN | A | 357 | −2.770 | 2.696 | −26.798 | 1.00 | 7.29 |
| ATOM | 1685 | OD1 | ASN | A | 357 | −2.076 | 1.678 | −26.493 | 1.00 | 8.50 |
| ATOM | 1686 | ND2 | ASN | A | 357 | −3.887 | 2.928 | −26.174 | 1.00 | 8.77 |
| ATOM | 1687 | C | ASN | A | 357 | −0.041 | 2.561 | −27.988 | 1.00 | 6.61 |
| ATOM | 1688 | O | ASN | A | 357 | 0.541 | 3.284 | −27.180 | 1.00 | 7.75 |
| ATOM | 1689 | N | ILE | A | 358 | 0.437 | 1.369 | −28.283 | 1.00 | 5.48 |
| ATOM | 1690 | CA | ILE | A | 358 | 1.721 | 0.899 | −27.669 | 1.00 | 5.60 |
| ATOM | 1691 | CB | ILE | A | 358 | 1.940 | −0.596 | −27.946 | 1.00 | 6.09 |
| ATOM | 1692 | CG1 | ILE | A | 358 | 0.793 | −1.433 | −27.287 | 1.00 | 6.84 |
| ATOM | 1693 | CD1 | ILE | A | 358 | 0.642 | −1.388 | −25.847 | 1.00 | 7.02 |
| ATOM | 1694 | CG2 | ILE | A | 358 | 3.292 | −0.994 | −27.375 | 1.00 | 5.81 |
| ATOM | 1695 | C | ILE | A | 358 | 2.795 | 1.692 | −28.363 | 1.00 | 5.94 |
| ATOM | 1696 | O | ILE | A | 358 | 2.855 | 1.772 | −29.631 | 1.00 | 6.64 |
| ATOM | 1697 | N | ASP | A | 359 | 3.706 | 2.255 | −27.555 | 1.00 | 4.84 |
| ATOM | 1698 | CA | ASP | A | 359 | 4.833 | 2.963 | −28.114 | 1.00 | 4.88 |
| ATOM | 1699 | CB | ASP | A | 359 | 5.195 | 4.111 | −27.169 | 1.00 | 5.64 |
| ATOM | 1700 | CG | ASP | A | 359 | 4.098 | 5.139 | −27.105 | 1.00 | 6.23 |
| ATOM | 1701 | OD1 | ASP | A | 359 | 3.725 | 5.699 | −28.202 | 1.00 | 7.22 |
| ATOM | 1702 | OD2 | ASP | A | 359 | 3.534 | 5.456 | −26.045 | 1.00 | 6.68 |
| ATOM | 1703 | C | ASP | A | 359 | 6.014 | 2.107 | −28.343 | 1.00 | 5.09 |
| ATOM | 1704 | O | ASP | A | 359 | 6.728 | 2.156 | −29.387 | 1.00 | 5.79 |
| ATOM | 1705 | N | VAL | A | 360 | 6.368 | 1.270 | −27.340 | 1.00 | 4.94 |
| ATOM | 1706 | CA | VAL | A | 360 | 7.533 | 0.377 | −27.321 | 1.00 | 5.41 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1707 | CB | VAL | A | 360 | 8.777 | 1.064 | −26.687 | 1.00 | 5.10 |
| ATOM | 1708 | CG1 | VAL | A | 360 | 9.197 | 2.330 | −27.454 | 1.00 | 5.67 |
| ATOM | 1709 | CG2 | VAL | A | 360 | 8.550 | 1.397 | −25.221 | 1.00 | 5.78 |
| ATOM | 1710 | C | VAL | A | 360 | 7.208 | −0.861 | −26.516 | 1.00 | 4.41 |
| ATOM | 1711 | O | VAL | A | 360 | 6.226 | −0.886 | −25.782 | 1.00 | 5.19 |
| ATOM | 1712 | N | ALA | A | 361 | 8.065 | −1.866 | −26.644 | 1.00 | 4.82 |
| ATOM | 1713 | CA | ALA | A | 361 | 8.032 | −3.025 | −25.786 | 1.00 | 4.40 |
| ATOM | 1714 | CB | ALA | A | 361 | 7.837 | −4.266 | −26.606 | 1.00 | 5.13 |
| ATOM | 1715 | C | ALA | A | 361 | 9.257 | −3.135 | −24.955 | 1.00 | 4.85 |
| ATOM | 1716 | O | ALA | A | 361 | 10.332 | −2.659 | −25.348 | 1.00 | 4.85 |
| ATOM | 1717 | N | ALA | A | 362 | 9.157 | −3.913 | −23.871 | 1.00 | 4.38 |
| ATOM | 1718 | CA | ALA | A | 362 | 10.343 | −4.211 | −23.017 | 1.00 | 4.66 |
| ATOM | 1719 | CB | ALA | A | 362 | 10.604 | −3.075 | −22.040 | 1.00 | 5.12 |
| ATOM | 1720 | C | ALA | A | 362 | 10.063 | −5.544 | −22.349 | 1.00 | 4.63 |
| ATOM | 1721 | O | ALA | A | 362 | 8.901 | −5.949 | −22.243 | 1.00 | 4.56 |
| ATOM | 1722 | N | PRO | A | 363 | 11.098 | −6.202 | −21.794 | 1.00 | 4.75 |
| ATOM | 1723 | CA | PRO | A | 363 | 10.854 | −7.457 | −21.113 | 1.00 | 5.03 |
| ATOM | 1724 | CB | PRO | A | 363 | 12.310 | −7.933 | −20.807 | 1.00 | 5.56 |
| ATOM | 1725 | CG | PRO | A | 363 | 13.112 | −6.747 | −20.837 | 1.00 | 5.52 |
| ATOM | 1726 | CD | PRO | A | 363 | 12.537 | −5.886 | −21.890 | 1.00 | 5.59 |
| ATOM | 1727 | C | PRO | A | 363 | 10.035 | −7.296 | −19.882 | 1.00 | 4.95 |
| ATOM | 1728 | O | PRO | A | 363 | 10.410 | −6.600 | −18.929 | 1.00 | 6.07 |
| ATOM | 1729 | N | GLY | A | 364 | 8.902 | −8.019 | −19.811 | 1.00 | 4.45 |
| ATOM | 1730 | CA | GLY | A | 364 | 8.134 | −8.221 | −18.633 | 1.00 | 4.81 |
| ATOM | 1731 | C | GLY | A | 364 | 7.975 | −9.622 | −18.137 | 1.00 | 4.58 |
| ATOM | 1732 | O | GLY | A | 364 | 7.366 | −9.881 | −17.122 | 1.00 | 4.95 |
| ATOM | 1733 | N | GLY | A | 365 | 8.519 | −10.551 | −18.964 | 1.00 | 5.43 |
| ATOM | 1734 | CA | GLY | A | 365 | 8.549 | −11.968 | −18.574 | 1.00 | 5.30 |
| ATOM | 1735 | C | GLY | A | 365 | 7.305 | −12.738 | −18.958 | 1.00 | 5.95 |
| ATOM | 1736 | O | GLY | A | 365 | 6.234 | −12.183 | −19.175 | 1.00 | 6.71 |
| ATOM | 1737 | N | ALA | A | 366 | 7.496 | −14.034 | −19.093 | 1.00 | 6.43 |
| ATOM | 1738 | CA | ALA | A | 366 | 6.381 | −14.950 | −19.434 | 1.00 | 6.70 |
| ATOM | 1739 | CB | ALA | A | 366 | 6.309 | −15.187 | −20.901 | 1.00 | 6.91 |
| ATOM | 1740 | C | ALA | A | 366 | 6.565 | −16.219 | −18.615 | 1.00 | 6.85 |
| ATOM | 1741 | O | ALA | A | 366 | 7.339 | −17.117 | −19.085 | 1.00 | 8.17 |
| ATOM | 1742 | N | GLN | A | 367 | 5.892 | −16.305 | −17.493 | 1.00 | 6.60 |
| ATOM | 1743 | CA | GLN | A | 367 | 6.042 | −17.389 | −16.546 | 1.00 | 7.44 |
| ATOM | 1744 | CB | GLN | A | 367 | 5.922 | −16.806 | −15.131 | 1.00 | 7.93 |
| ATOM | 1745 | CG | GLN | A | 367 | 7.066 | −15.850 | −14.729 | 1.00 | 7.53 |
| ATOM | 1746 | CD | GLN | A | 367 | 6.836 | −15.297 | −13.354 | 1.00 | 7.96 |
| ATOM | 1747 | OE1 | GLN | A | 367 | 5.786 | −14.743 | −13.042 | 1.00 | 9.16 |
| ATOM | 1748 | NE2 | GLN | A | 367 | 7.814 | −15.474 | −12.451 | 1.00 | 7.49 |
| ATOM | 1749 | C | GLN | A | 367 | 4.943 | −18.410 | −16.743 | 1.00 | 7.17 |
| ATOM | 1750 | O | GLN | A | 367 | 3.833 | −18.104 | −17.204 | 1.00 | 8.46 |
| ATOM | 1751 | N | SER | A | 368 | 5.197 | −19.643 | −16.290 | 1.00 | 7.60 |
| ATOM | 1752 | CA | SER | A | 368 | 4.185 | −20.697 | −16.319 | 1.00 | 7.36 |
| ATOM | 1753 | CB | SER | A | 368 | 4.466 | −21.784 | −17.334 | 1.00 | 8.32 |
| ATOM | 1754 | OG | SER | A | 368 | 5.544 | −22.635 | −16.952 | 1.00 | 8.40 |
| ATOM | 1755 | C | SER | A | 368 | 3.904 | −21.233 | −14.948 | 1.00 | 8.67 |
| ATOM | 1756 | O | SER | A | 368 | 3.054 | −22.130 | −14.788 | 1.00 | 9.23 |
| ATOM | 1757 | N | PHE | A | 369 | 4.559 | −20.690 | −13.890 | 1.00 | 9.15 |
| ATOM | 1758 | CA | PHE | A | 369 | 4.333 | −21.108 | −12.502 | 1.00 | 10.03 |
| ATOM | 1759 | CB | PHE | A | 369 | 4.942 | −22.468 | −12.220 | 1.00 | 10.13 |
| ATOM | 1760 | CG | PHE | A | 369 | 6.408 | −22.556 | −12.371 | 1.00 | 9.92 |
| ATOM | 1761 | CD1 | PHE | A | 369 | 7.050 | −22.825 | −13.534 | 1.00 | 9.82 |
| ATOM | 1762 | CE1 | PHE | A | 369 | 8.369 | −22.888 | −13.710 | 1.00 | 10.94 |
| ATOM | 1763 | CZ | PHE | A | 369 | 9.155 | −22.712 | −12.597 | 1.00 | 11.14 |
| ATOM | 1764 | CE2 | PHE | A | 369 | 8.604 | −22.438 | −11.384 | 1.00 | 11.18 |
| ATOM | 1765 | CD2 | PHE | A | 369 | 7.259 | −22.383 | −11.204 | 1.00 | 10.58 |
| ATOM | 1766 | C | PHE | A | 369 | 4.873 | −20.011 | −11.596 | 1.00 | 10.37 |
| ATOM | 1767 | O | PHE | A | 369 | 5.642 | −19.135 | −12.064 | 1.00 | 9.55 |
| ATOM | 1768 | N | ALA | A | 370 | 4.498 | −20.053 | −10.312 | 1.00 | 14.06 |
| ATOM | 1769 | CA | ALA | A | 370 | 4.892 | −18.969 | −9.415 | 1.00 | 12.94 |
| ATOM | 1770 | CB | ALA | A | 370 | 4.146 | −19.099 | −8.073 | 1.00 | 16.83 |
| ATOM | 1771 | C | ALA | A | 370 | 6.391 | −18.943 | −9.214 | 1.00 | 10.84 |
| ATOM | 1772 | O | ALA | A | 370 | 7.018 | −19.891 | −9.012 | 1.00 | 12.18 |
| ATOM | 1773 | N | ASN | A | 371 | 6.922 | −17.727 | −9.331 | 1.00 | 10.56 |
| ATOM | 1774 | CA | ASN | A | 371 | 8.346 | −17.495 | −9.153 | 1.00 | 9.61 |
| ATOM | 1775 | CB | ASN | A | 371 | 8.838 | −17.891 | −7.682 | 1.00 | 10.27 |
| ATOM | 1776 | CG | ASN | A | 371 | 10.039 | −17.106 | −7.271 | 1.00 | 11.82 |
| ATOM | 1777 | OD1 | ASN | A | 371 | 10.136 | −15.908 | −7.525 | 1.00 | 9.95 |
| ATOM | 1778 | ND2 | ASN | A | 371 | 10.957 | −17.732 | −6.566 | 1.00 | 14.01 |
| ATOM | 1779 | C | ASN | A | 371 | 9.237 | −18.202 | −10.154 | 1.00 | 7.76 |
| ATOM | 1780 | O | ASN | A | 371 | 10.424 | −18.349 | −9.972 | 1.00 | 9.49 |
| ATOM | 1781 | N | ASP | A | 372 | 8.660 | −18.554 | −11.328 | 1.00 | 7.67 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1782 | CA | ASP | A | 372 | 9.439 | −19.105 | −12.423 | 1.00 | 7.36 |
| ATOM | 1783 | CB | ASP | A | 372 | 8.388 | −19.331 | −13.578 | 1.00 | 6.98 |
| ATOM | 1784 | CG | ASP | A | 372 | 8.931 | −19.840 | −14.888 | 1.00 | 6.85 |
| ATOM | 1785 | OD1 | ASP | A | 372 | 10.130 | −20.026 | −15.077 | 1.00 | 8.43 |
| ATOM | 1786 | OD2 | ASP | A | 372 | 7.994 | −19.987 | −15.770 | 1.00 | 8.15 |
| ATOM | 1787 | C | ASP | A | 372 | 10.552 | −18.144 | −12.844 | 1.00 | 7.36 |
| ATOM | 1788 | O | ASP | A | 372 | 10.260 | −16.943 | −13.113 | 1.00 | 6.89 |
| ATOM | 1789 | N | SER | A | 373 | 11.789 | −18.611 | −13.057 | 1.00 | 7.22 |
| ATOM | 1790 | CA | SER | A | 373 | 12.904 | −17.824 | −13.435 | 1.00 | 7.27 |
| ATOM | 1791 | CB | SER | A | 373 | 14.212 | −18.514 | −13.097 | 1.00 | 8.45 |
| ATOM | 1792 | OG | SER | A | 373 | 14.306 | −19.703 | −13.923 | 1.00 | 10.38 |
| ATOM | 1793 | C | SER | A | 373 | 12.855 | −17.252 | −14.831 | 1.00 | 7.13 |
| ATOM | 1794 | O | SER | A | 373 | 13.729 | −16.486 | −15.246 | 1.00 | 8.16 |
| ATOM | 1795 | N | GLU | A | 374 | 11.848 | −17.684 | −15.609 | 1.00 | 6.59 |
| ATOM | 1796 | CA | GLU | A | 374 | 11.550 | −17.008 | −16.876 | 1.00 | 6.73 |
| ATOM | 1797 | CB | GLU | A | 374 | 10.529 | −17.795 | −17.698 | 1.00 | 7.58 |
| ATOM | 1798 | CG | GLU | A | 374 | 11.052 | −19.129 | −18.224 | 1.00 | 8.39 |
| ATOM | 1799 | CD | GLU | A | 374 | 12.152 | −18.969 | −19.175 | 1.00 | 9.22 |
| ATOM | 1800 | OE1 | GLU | A | 374 | 11.868 | −18.586 | −20.360 | 1.00 | 12.84 |
| ATOM | 1801 | OE2 | GLU | A | 374 | 13.336 | −19.052 | −18.871 | 1.00 | 11.82 |
| ATOM | 1802 | C | GLU | A | 374 | 10.998 | −15.588 | −16.642 | 1.00 | 6.60 |
| ATOM | 1803 | O | GLU | A | 374 | 10.897 | −14.774 | −17.590 | 1.00 | 7.38 |
| ATOM | 1804 | N | GLY | A | 375 | 10.609 | −15.248 | −15.404 | 1.00 | 6.07 |
| ATOM | 1805 | CA | GLY | A | 375 | 10.131 | −13.891 | −15.077 | 1.00 | 6.30 |
| ATOM | 1806 | C | GLY | A | 375 | 11.252 | −12.887 | −14.941 | 1.00 | 5.58 |
| ATOM | 1807 | O | GLY | A | 375 | 12.423 | −13.169 | −15.175 | 1.00 | 6.01 |
| ATOM | 1808 | N | VAL | A | 376 | 10.843 | −11.743 | −14.426 | 1.00 | 5.53 |
| ATOM | 1809 | CA | VAL | A | 376 | 11.732 | −10.617 | −14.162 | 1.00 | 5.61 |
| ATOM | 1810 | CB | VAL | A | 376 | 11.093 | −9.264 | −14.596 | 1.00 | 5.00 |
| ATOM | 1811 | CG1 | VAL | A | 376 | 11.873 | −8.097 | −14.061 | 1.00 | 5.19 |
| ATOM | 1812 | CG2 | VAL | A | 376 | 10.933 | −9.218 | −16.085 | 1.00 | 6.21 |
| ATOM | 1813 | C | VAL | A | 376 | 12.110 | −10.617 | −12.689 | 1.00 | 5.01 |
| ATOM | 1814 | O | VAL | A | 376 | 11.229 | −10.626 | −11.824 | 1.00 | 4.97 |
| ATOM | 1815 | N | LEU | A | 377 | 13.416 | −10.709 | −12.425 | 1.00 | 5.13 |
| ATOM | 1816 | CA | LEU | A | 377 | 13.896 | −10.809 | −11.043 | 1.00 | 5.03 |
| ATOM | 1817 | CB | LEU | A | 377 | 15.204 | −11.574 | −11.030 | 1.00 | 5.59 |
| ATOM | 1818 | CG | LEU | A | 377 | 15.828 | −11.880 | −9.665 | 1.00 | 5.86 |
| ATOM | 1819 | CD1 | LEU | A | 377 | 14.988 | −12.738 | −8.806 | 1.00 | 6.64 |
| ATOM | 1820 | CD2 | LEU | A | 377 | 17.205 | −12.513 | −9.802 | 1.00 | 6.55 |
| ATOM | 1821 | C | LEU | A | 377 | 14.196 | −9.416 | −10.459 | 1.00 | 4.22 |
| ATOM | 1822 | O | LEU | A | 377 | 14.775 | −8.569 | −11.109 | 1.00 | 5.02 |
| ATOM | 1823 | N | SER | A | 378 | 13.674 | −9.211 | −9.248 | 1.00 | 4.66 |
| ATOM | 1824 | CA | SER | A | 378 | 13.896 | −7.927 | −8.561 | 1.00 | 4.58 |
| ATOM | 1825 | CB | SER | A | 378 | 12.932 | −6.879 | −9.083 | 1.00 | 4.79 |
| ATOM | 1826 | OG | SER | A | 378 | 13.362 | −5.598 | −8.714 | 1.00 | 5.38 |
| ATOM | 1827 | C | SER | A | 378 | 13.842 | −8.136 | −7.067 | 1.00 | 5.15 |
| ATOM | 1828 | O | SER | A | 378 | 13.609 | −9.209 | −6.539 | 1.00 | 5.53 |
| ATOM | 1829 | N | THR | A | 379 | 14.029 | −7.002 | −6.355 | 1.00 | 5.21 |
| ATOM | 1830 | CA | THR | A | 379 | 13.815 | −6.914 | −4.906 | 1.00 | 5.09 |
| ATOM | 1831 | CB | THR | A | 379 | 14.208 | −5.506 | −4.421 | 1.00 | 4.92 |
| ATOM | 1832 | OG1 | THR | A | 379 | 13.675 | −4.509 | −5.324 | 1.00 | 5.01 |
| ATOM | 1833 | CG2 | THR | A | 379 | 15.725 | −5.307 | −4.451 | 1.00 | 5.43 |
| ATOM | 1834 | C | THR | A | 379 | 12.445 | −7.253 | −4.526 | 1.00 | 5.05 |
| ATOM | 1835 | O | THR | A | 379 | 11.463 | −6.850 | −5.236 | 1.00 | 6.03 |
| ATOM | 1836 | N | TYR | A | 380 | 12.222 | −7.897 | −3.410 | 1.00 | 5.22 |
| ATOM | 1837 | CA | TYR | A | 380 | 10.961 | −8.408 | −3.024 | 1.00 | 5.45 |
| ATOM | 1838 | CB | TYR | A | 380 | 10.698 | −9.773 | −3.748 | 1.00 | 6.80 |
| ATOM | 1839 | CG | TYR | A | 380 | 9.345 | −10.248 | −3.896 | 1.00 | 9.74 |
| ATOM | 1840 | CD1 | TYR | A | 380 | 8.333 | −9.427 | −4.410 | 1.00 | 11.08 |
| ATOM | 1841 | CE1 | TYR | A | 380 | 6.963 | −10.076 | −4.475 | 1.00 | 14.44 |
| ATOM | 1842 | CZ | TYR | A | 380 | 6.890 | −11.401 | −3.950 | 1.00 | 12.17 |
| ATOM | 1843 | OH | TYR | A | 380 | 5.742 | −12.325 | −3.912 | 1.00 | 22.38 |
| ATOM | 1844 | CE2 | TYR | A | 380 | 7.840 | −12.107 | −3.542 | 1.00 | 16.42 |
| ATOM | 1845 | CD2 | TYR | A | 380 | 9.063 | −11.556 | −3.488 | 1.00 | 10.82 |
| ATOM | 1846 | C | TYR | A | 380 | 10.853 | −8.596 | −1.510 | 1.00 | 5.43 |
| ATOM | 1847 | O | TYR | A | 380 | 11.788 | −8.158 | −0.817 | 1.00 | 6.11 |
| ATOM | 1848 | N | ASN | A | 381 | 9.805 | −9.145 | −0.985 | 1.00 | 5.77 |
| ATOM | 1849 | CA | ASN | A | 381 | 9.661 | −9.365 | 0.457 | 1.00 | 5.95 |
| ATOM | 1850 | CB | ASN | A | 381 | 8.777 | −8.237 | 1.040 | 1.00 | 6.34 |
| ATOM | 1851 | CG | ASN | A | 381 | 8.832 | −8.237 | 2.577 | 1.00 | 5.59 |
| ATOM | 1852 | OD1 | ASN | A | 381 | 8.121 | −8.985 | 3.226 | 1.00 | 6.24 |
| ATOM | 1853 | ND2 | ASN | A | 381 | 9.684 | −7.389 | 3.153 | 1.00 | 5.15 |
| ATOM | 1854 | C | ASN | A | 381 | 9.053 | −10.699 | 0.645 | 1.00 | 6.60 |
| ATOM | 1855 | O | ASN | A | 381 | 8.199 | −11.112 | −0.175 | 1.00 | 6.82 |
| ATOM | 1856 | N | SER | A | 382 | 9.412 | −11.393 | 1.692 | 1.00 | 6.99 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1857 | CA | SER | A | 382 | 8.909 | −12.745 | 1.978 | 1.00 | 6.67 |
| ATOM | 1858 | CB | SER | A | 382 | 9.939 | −13.547 | 2.755 | 1.00 | 7.93 |
| ATOM | 1859 | OG | SER | A | 382 | 10.112 | −13.002 | 4.054 | 1.00 | 9.98 |
| ATOM | 1860 | C | SER | A | 382 | 7.622 | −12.797 | 2.677 | 1.00 | 7.50 |
| ATOM | 1861 | O | SER | A | 382 | 7.041 | −13.881 | 2.906 | 1.00 | 8.69 |
| ATOM | 1862 | N | GLY | A | 383 | 7.060 | −11.660 | 3.151 | 1.00 | 7.27 |
| ATOM | 1863 | CA | GLY | A | 383 | 5.859 | −11.700 | 3.970 | 1.00 | 7.34 |
| ATOM | 1864 | C | GLY | A | 383 | 4.639 | −12.138 | 3.181 | 1.00 | 8.08 |
| ATOM | 1865 | O | GLY | A | 383 | 4.375 | −11.591 | 2.088 | 1.00 | 8.91 |
| ATOM | 1866 | N | SER | A | 384 | 3.773 | −12.969 | 3.716 | 1.00 | 8.84 |
| ATOM | 1867 | CA | SER | A | 384 | 2.523 | −13.285 | 3.052 | 1.00 | 9.88 |
| ATOM | 1868 | CB | SER | A | 384 | 1.979 | −14.643 | 3.565 | 1.00 | 12.08 |
| ATOM | 1869 | OG | SER | A | 384 | 1.901 | −14.613 | 4.906 | 1.00 | 17.04 |
| ATOM | 1870 | C | SER | A | 384 | 1.535 | −12.195 | 3.235 | 1.00 | 9.08 |
| ATOM | 1871 | O | SER | A | 384 | 0.666 | −12.021 | 2.345 | 1.00 | 9.90 |
| ATOM | 1872 | N | SER | A | 385 | 1.520 | −11.431 | 4.315 | 1.00 | 8.60 |
| ATOM | 1873 | CA | SER | A | 385 | 0.568 | −10.367 | 4.564 | 1.00 | 9.88 |
| ATOM | 1874 | CB | SER | A | 385 | −0.572 | −10.739 | 5.532 | 1.00 | 12.16 |
| ATOM | 1875 | OG | SER | A | 385 | −0.049 | −11.315 | 6.724 | 1.00 | 15.59 |
| ATOM | 1876 | C | SER | A | 385 | 1.327 | −9.195 | 5.039 | 1.00 | 9.40 |
| ATOM | 1877 | O | SER | A | 385 | 1.659 | −8.242 | 4.297 | 1.00 | 9.02 |
| ATOM | 1878 | N | THR | A | 386 | 1.696 | −9.162 | 6.336 | 1.00 | 9.23 |
| ATOM | 1879 | CA | THR | A | 386 | 2.604 | −8.189 | 6.882 | 1.00 | 9.50 |
| ATOM | 1880 | CB | THR | A | 386 | 2.563 | −8.228 | 8.435 | 1.00 | 8.72 |
| ATOM | 1881 | OG1 | THR | A | 386 | 2.709 | −9.590 | 8.816 | 1.00 | 10.92 |
| ATOM | 1882 | CG2 | THR | A | 386 | 1.160 | −7.755 | 8.878 | 1.00 | 9.99 |
| ATOM | 1883 | C | THR | A | 386 | 4.023 | −8.337 | 6.327 | 1.00 | 8.52 |
| ATOM | 1884 | O | THR | A | 386 | 4.425 | −9.453 | 5.959 | 1.00 | 8.06 |
| ATOM | 1885 | N | PRO | A | 387 | 4.800 | −7.272 | 6.326 | 1.00 | 8.01 |
| ATOM | 1886 | CA | PRO | A | 387 | 6.164 | −7.403 | 5.780 | 1.00 | 7.77 |
| ATOM | 1887 | CB | PRO | A | 387 | 6.695 | −5.995 | 5.727 | 1.00 | 9.07 |
| ATOM | 1888 | CG | PRO | A | 387 | 5.798 | −5.151 | 6.539 | 1.00 | 12.35 |
| ATOM | 1889 | CD | PRO | A | 387 | 4.521 | −5.906 | 6.751 | 1.00 | 8.95 |
| ATOM | 1890 | C | PRO | A | 387 | 7.037 | −8.309 | 6.640 | 1.00 | 8.59 |
| ATOM | 1891 | O | PRO | A | 387 | 6.882 | −8.323 | 7.861 | 1.00 | 9.69 |
| ATOM | 1892 | N | SER | A | 388 | 7.951 | −9.017 | 6.039 | 1.00 | 7.22 |
| ATOM | 1893 | CA | SER | A | 388 | 8.928 | −9.882 | 6.719 | 1.00 | 6.84 |
| ATOM | 1894 | CB | SER | A | 388 | 8.431 | −11.309 | 6.640 | 1.00 | 8.27 |
| ATOM | 1895 | OG | SER | A | 388 | 9.252 | −12.193 | 7.377 | 1.00 | 9.88 |
| ATOM | 1896 | C | SER | A | 388 | 10.278 | −9.624 | 6.082 | 1.00 | 7.61 |
| ATOM | 1897 | O | SER | A | 388 | 10.605 | −8.534 | 5.608 | 1.00 | 6.35 |
| ATOM | 1898 | N | SER | A | 389 | 11.104 | −10.654 | 6.108 | 1.00 | 8.44 |
| ATOM | 1899 | CA | SER | A | 389 | 12.462 | −10.520 | 5.592 | 1.00 | 8.39 |
| ATOM | 1900 | CB | SER | A | 389 | 13.261 | −11.784 | 5.879 | 1.00 | 12.55 |
| ATOM | 1901 | OG | SER | A | 389 | 12.695 | −12.796 | 5.208 | 1.00 | 18.53 |
| ATOM | 1902 | C | SER | A | 389 | 12.538 | −10.123 | 4.124 | 1.00 | 7.34 |
| ATOM | 1903 | O | SER | A | 389 | 11.664 | −10.516 | 3.295 | 1.00 | 7.95 |
| ATOM | 1904 | N | ASP | A | 390 | 13.584 | −9.443 | 3.743 | 1.00 | 6.91 |
| ATOM | 1905 | CA | ASP | A | 390 | 13.935 | −9.125 | 2.347 | 1.00 | 7.02 |
| ATOM | 1906 | CB | ASP | A | 390 | 15.207 | −8.345 | 2.258 | 1.00 | 7.16 |
| ATOM | 1907 | CG | ASP | A | 390 | 15.146 | −6.926 | 2.845 | 1.00 | 7.70 |
| ATOM | 1908 | OD1 | ASP | A | 390 | 14.032 | −6.368 | 2.946 | 1.00 | 8.25 |
| ATOM | 1909 | OD2 | ASP | A | 390 | 16.253 | −6.362 | 3.057 | 1.00 | 9.23 |
| ATOM | 1910 | C | ASP | A | 390 | 14.061 | −10.437 | 1.579 | 1.00 | 7.82 |
| ATOM | 1911 | O | ASP | A | 390 | 14.646 | −11.416 | 2.055 | 1.00 | 9.20 |
| ATOM | 1912 | N | SER | A | 391 | 13.676 | −10.398 | 0.305 | 1.00 | 7.19 |
| ATOM | 1913 | CA | SER | A | 391 | 13.917 | −11.510 | −0.621 | 1.00 | 6.84 |
| ATOM | 1914 | CB | SER | A | 391 | 12.758 | −12.470 | −0.523 | 1.00 | 7.48 |
| ATOM | 1915 | OG | SER | A | 391 | 11.582 | −11.872 | −1.031 | 1.00 | 8.47 |
| ATOM | 1916 | C | SER | A | 391 | 14.143 | −10.971 | −2.006 | 1.00 | 6.79 |
| ATOM | 1917 | O | SER | A | 391 | 14.109 | −9.745 | −2.262 | 1.00 | 6.77 |
| ATOM | 1918 | N | TYR | A | 392 | 14.363 | −11.870 | −2.952 | 1.00 | 6.93 |
| ATOM | 1919 | CA | TYR | A | 392 | 14.386 | −11.585 | −4.392 | 1.00 | 6.68 |
| ATOM | 1920 | CB | TYR | A | 392 | 15.773 | −11.762 | −4.990 | 1.00 | 7.56 |
| ATOM | 1921 | CG | TYR | A | 392 | 16.812 | −10.948 | −4.295 | 1.00 | 7.71 |
| ATOM | 1922 | CD1 | TYR | A | 392 | 17.016 | −9.588 | −4.546 | 1.00 | 6.96 |
| ATOM | 1923 | CE1 | TYR | A | 392 | 17.904 | −8.826 | −3.813 | 1.00 | 6.32 |
| ATOM | 1924 | CZ | TYR | A | 392 | 18.662 | −9.397 | −2.886 | 1.00 | 6.71 |
| ATOM | 1925 | OH | TYR | A | 392 | 19.502 | −8.564 | −2.187 | 1.00 | 9.05 |
| ATOM | 1926 | CE2 | TYR | A | 392 | 18.469 | −10.695 | −2.544 | 1.00 | 8.98 |
| ATOM | 1927 | CD2 | TYR | A | 392 | 17.625 | −11.511 | −3.279 | 1.00 | 8.30 |
| ATOM | 1928 | C | TYR | A | 392 | 13.413 | −12.445 | −5.053 | 1.00 | 7.98 |
| ATOM | 1929 | O | TYR | A | 392 | 13.297 | −13.664 | −4.688 | 1.00 | 10.80 |
| ATOM | 1930 | N | GLY | A | 393 | 12.612 | −11.982 | −5.981 | 1.00 | 6.52 |
| ATOM | 1931 | CA | GLY | A | 393 | 11.597 | −12.776 | −6.604 | 1.00 | 6.63 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 1932 | C | GLY | A | 393 | 11.382 | −12.440 | −8.044 | 1.00 | 6.07 |
| ATOM | 1933 | O | GLY | A | 393 | 11.683 | −11.353 | −8.520 | 1.00 | 5.85 |
| ATOM | 1934 | N | TYR | A | 394 | 10.936 | −13.479 | −8.784 | 1.00 | 5.56 |
| ATOM | 1935 | CA | TYR | A | 394 | 10.596 | −13.362 | −10.185 | 1.00 | 5.99 |
| ATOM | 1936 | CB | TYR | A | 394 | 10.964 | −14.643 | −11.000 | 1.00 | 6.91 |
| ATOM | 1937 | CG | TYR | A | 394 | 12.382 | −15.044 | −11.012 | 1.00 | 6.47 |
| ATOM | 1938 | CD1 | TYR | A | 394 | 13.297 | −14.561 | −11.946 | 1.00 | 6.66 |
| ATOM | 1939 | CE1 | TYR | A | 394 | 14.625 | −14.990 | −11.960 | 1.00 | 8.30 |
| ATOM | 1940 | CZ | TYR | A | 394 | 14.999 | −15.927 | −11.043 | 1.00 | 8.15 |
| ATOM | 1941 | OH | TYR | A | 394 | 16.370 | −16.318 | −11.104 | 1.00 | 11.44 |
| ATOM | 1942 | CE2 | TYR | A | 394 | 14.182 | −16.415 | −10.130 | 1.00 | 8.74 |
| ATOM | 1943 | CD2 | TYR | A | 394 | 12.852 | −15.997 | −10.095 | 1.00 | 8.35 |
| ATOM | 1944 | C | TYR | A | 394 | 9.129 | −13.120 | −10.366 | 1.00 | 5.83 |
| ATOM | 1945 | O | TYR | A | 394 | 8.312 | −13.864 | −9.873 | 1.00 | 7.06 |
| ATOM | 1946 | N | SER | A | 395 | 8.789 | −12.030 | −11.083 | 1.00 | 6.38 |
| ATOM | 1947 | CA | SER | A | 395 | 7.410 | −11.655 | −11.324 | 1.00 | 6.59 |
| ATOM | 1948 | CB | SER | A | 395 | 7.045 | −10.405 | −10.576 | 1.00 | 8.97 |
| ATOM | 1949 | OG | SER | A | 395 | 6.919 | −10.642 | −9.151 | 1.00 | 13.33 |
| ATOM | 1950 | C | SER | A | 395 | 7.228 | −11.449 | −12.813 | 1.00 | 6.43 |
| ATOM | 1951 | O | SER | A | 395 | 8.189 | −11.402 | −13.568 | 1.00 | 8.06 |
| ATOM | 1952 | N | GLN | A | 396 | 6.018 | −11.234 | −13.251 | 1.00 | 6.41 |
| ATOM | 1953 | CA | GLN | A | 396 | 5.745 | −10.944 | −14.668 | 1.00 | 6.44 |
| ATOM | 1954 | CB | GLN | A | 396 | 5.357 | −12.172 | −15.456 | 1.00 | 6.50 |
| ATOM | 1955 | CG | GLN | A | 396 | 4.057 | −12.792 | −15.065 | 1.00 | 7.36 |
| ATOM | 1956 | CD | GLN | A | 396 | 3.571 | −13.898 | −15.978 | 1.00 | 7.88 |
| ATOM | 1957 | OE1 | GLN | A | 396 | 4.180 | −14.266 | −16.934 | 1.00 | 7.28 |
| ATOM | 1958 | NE2 | GLN | A | 396 | 2.428 | −14.389 | −15.657 | 1.00 | 11.12 |
| ATOM | 1959 | C | GLN | A | 396 | 4.643 | −9.914 | −14.835 | 1.00 | 5.38 |
| ATOM | 1960 | O | GLN | A | 396 | 3.783 | −9.791 | −13.980 | 1.00 | 6.64 |
| ATOM | 1961 | N | GLY | A | 397 | 4.689 | −9.226 | −15.992 | 1.00 | 4.84 |
| ATOM | 1962 | CA | GLY | A | 397 | 3.613 | −8.328 | −16.342 | 1.00 | 5.25 |
| ATOM | 1963 | C | GLY | A | 397 | 4.143 | −7.219 | −17.137 | 1.00 | 5.02 |
| ATOM | 1964 | O | GLY | A | 397 | 5.333 | −6.880 | −17.217 | 1.00 | 5.60 |
| ATOM | 1965 | N | THR | A | 398 | 3.204 | −6.472 | −17.754 | 1.00 | 5.55 |
| ATOM | 1966 | CA | THR | A | 398 | 3.530 | −5.130 | −18.270 | 1.00 | 4.79 |
| ATOM | 1967 | CB | THR | A | 398 | 2.427 | −4.471 | −19.086 | 1.00 | 4.92 |
| ATOM | 1968 | OG1 | THR | A | 398 | 1.285 | −4.339 | −18.283 | 1.00 | 5.20 |
| ATOM | 1969 | CG2 | THR | A | 398 | 2.144 | −5.195 | −20.366 | 1.00 | 5.57 |
| ATOM | 1970 | C | THR | A | 398 | 4.033 | −4.237 | −17.118 | 1.00 | 4.88 |
| ATOM | 1971 | O | THR | A | 398 | 4.825 | −3.323 | −17.413 | 1.00 | 5.00 |
| ATOM | 1972 | N | SER | A | 399 | 3.703 | −4.552 | −15.887 | 1.00 | 5.22 |
| ATOM | 1973 | CA | SER | A | 399 | 4.226 | −3.835 | −14.733 | 1.00 | 5.52 |
| ATOM | 1974 | CB | SER | A | 399 | 3.657 | −4.424 | −13.435 | 1.00 | 8.77 |
| ATOM | 1975 | OG | SER | A | 399 | 2.353 | −3.974 | −13.180 | 1.00 | 12.78 |
| ATOM | 1976 | C | SER | A | 399 | 5.738 | −3.966 | −14.566 | 1.00 | 4.94 |
| ATOM | 1977 | O | SER | A | 399 | 6.315 | −3.147 | −13.933 | 1.00 | 5.21 |
| ATOM | 1978 | N | MET | A | 400 | 6.311 | −5.061 | −15.084 | 1.00 | 4.60 |
| ATOM | 1979 | CA | MET | A | 400 | 7.734 | −5.351 | −15.026 | 1.00 | 4.72 |
| ATOM | 1980 | CB | MET | A | 400 | 8.024 | −6.828 | −14.910 | 1.00 | 5.52 |
| ATOM | 1981 | CG | MET | A | 400 | 7.841 | −7.498 | −13.526 | 1.00 | 6.38 |
| ATOM | 1982 | SD | MET | A | 400 | 6.169 | −7.493 | −12.849 | 1.00 | 7.01 |
| ATOM | 1983 | CE | MET | A | 400 | 6.307 | −6.177 | −11.679 | 1.00 | 6.72 |
| ATOM | 1984 | C | MET | A | 400 | 8.427 | −4.765 | −16.224 | 1.00 | 4.53 |
| ATOM | 1985 | O | MET | A | 400 | 9.601 | −4.377 | −16.161 | 1.00 | 5.03 |
| ATOM | 1986 | N | ALA | A | 401 | 7.722 | −4.678 | −17.355 | 1.00 | 4.25 |
| ATOM | 1987 | CA | ALA | A | 401 | 8.281 | −4.076 | −18.574 | 1.00 | 4.33 |
| ATOM | 1988 | CB | ALA | A | 401 | 7.357 | −4.428 | −19.751 | 1.00 | 4.78 |
| ATOM | 1989 | C | ALA | A | 401 | 8.417 | −2.561 | −18.415 | 1.00 | 4.22 |
| ATOM | 1990 | O | ALA | A | 401 | 9.434 | −1.965 | −18.772 | 1.00 | 4.88 |
| ATOM | 1991 | N | ALA | A | 402 | 7.392 | −1.891 | −17.896 | 1.00 | 4.43 |
| ATOM | 1992 | CA | ALA | A | 402 | 7.407 | −0.435 | −17.727 | 1.00 | 4.11 |
| ATOM | 1993 | CB | ALA | A | 402 | 6.098 | 0.050 | −17.092 | 1.00 | 4.65 |
| ATOM | 1994 | C | ALA | A | 402 | 8.644 | 0.100 | −16.992 | 1.00 | 3.62 |
| ATOM | 1995 | O | ALA | A | 402 | 9.258 | 1.027 | −17.517 | 1.00 | 4.15 |
| ATOM | 1996 | N | PRO | A | 403 | 9.047 | −0.477 | −15.883 | 1.00 | 4.16 |
| ATOM | 1997 | CA | PRO | A | 403 | 10.235 | 0.126 | −15.138 | 1.00 | 4.22 |
| ATOM | 1998 | CB | PRO | A | 403 | 10.201 | −0.554 | −13.781 | 1.00 | 4.57 |
| ATOM | 1999 | CG | PRO | A | 403 | 9.395 | −1.803 | −14.036 | 1.00 | 4.53 |
| ATOM | 2000 | CD | PRO | A | 403 | 8.326 | −1.392 | −14.952 | 1.00 | 4.15 |
| ATOM | 2001 | C | PRO | A | 403 | 11.500 | −0.083 | −15.910 | 1.00 | 4.28 |
| ATOM | 2002 | O | PRO | A | 403 | 12.444 | 0.690 | −15.681 | 1.00 | 4.72 |
| ATOM | 2003 | N | HIS | A | 404 | 11.607 | −1.067 | −16.779 | 1.00 | 3.86 |
| ATOM | 2004 | CA | HIS | A | 404 | 12.775 | −1.103 | −17.704 | 1.00 | 4.22 |
| ATOM | 2005 | CB | HIS | A | 404 | 12.739 | −2.357 | −18.578 | 1.00 | 4.58 |
| ATOM | 2006 | CG | HIS | A | 404 | 13.099 | −3.652 | −17.891 | 1.00 | 4.50 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 2007 | ND1 | HIS | A | 404 | 12.222 | −4.465 | −17.259 | 1.00 | 4.78 |
| ATOM | 2008 | CE1 | HIS | A | 404 | 12.867 | −5.528 | −16.798 | 1.00 | 5.00 |
| ATOM | 2009 | NE2 | HIS | A | 404 | 14.131 | −5.445 | −17.107 | 1.00 | 5.17 |
| ATOM | 2010 | CD2 | HIS | A | 404 | 14.316 | −4.281 | −17.773 | 1.00 | 4.60 |
| ATOM | 2011 | C | HIS | A | 404 | 12.796 | 0.139 | −18.513 | 1.00 | 4.49 |
| ATOM | 2012 | O | HIS | A | 404 | 13.876 | 0.765 | −18.734 | 1.00 | 5.08 |
| ATOM | 2013 | N | VAL | A | 405 | 11.659 | 0.521 | −19.089 | 1.00 | 4.72 |
| ATOM | 2014 | CA | VAL | A | 405 | 11.579 | 1.708 | −19.921 | 1.00 | 4.32 |
| ATOM | 2015 | CB | VAL | A | 405 | 10.271 | 1.705 | −20.712 | 1.00 | 4.22 |
| ATOM | 2016 | CG1 | VAL | A | 405 | 10.120 | 2.964 | −21.577 | 1.00 | 4.10 |
| ATOM | 2017 | CG2 | VAL | A | 405 | 10.154 | 0.450 | −21.499 | 1.00 | 4.70 |
| ATOM | 2018 | C | VAL | A | 405 | 11.765 | 3.000 | −19.093 | 1.00 | 4.25 |
| ATOM | 2019 | O | VAL | A | 405 | 12.469 | 3.905 | −19.577 | 1.00 | 4.89 |
| ATOM | 2020 | N | ALA | A | 406 | 11.219 | 3.049 | −17.906 | 1.00 | 4.25 |
| ATOM | 2021 | CA | ALA | A | 406 | 11.428 | 4.215 | −17.043 | 1.00 | 4.05 |
| ATOM | 2022 | CB | ALA | A | 406 | 10.571 | 4.093 | −15.795 | 1.00 | 4.77 |
| ATOM | 2023 | C | ALA | A | 406 | 12.888 | 4.343 | −16.710 | 1.00 | 4.63 |
| ATOM | 2024 | O | ALA | A | 406 | 13.404 | 5.445 | −16.684 | 1.00 | 5.04 |
| ATOM | 2025 | N | GLY | A | 407 | 13.555 | 3.191 | −16.487 | 1.00 | 4.58 |
| ATOM | 2026 | CA | GLY | A | 407 | 14.998 | 3.295 | −16.209 | 1.00 | 5.33 |
| ATOM | 2027 | C | GLY | A | 407 | 15.733 | 3.806 | −17.428 | 1.00 | 5.26 |
| ATOM | 2028 | O | GLY | A | 407 | 16.654 | 4.633 | −17.281 | 1.00 | 5.34 |
| ATOM | 2029 | N | VAL | A | 408 | 15.423 | 3.349 | −18.650 | 1.00 | 4.99 |
| ATOM | 2030 | CA | VAL | A | 408 | 16.076 | 3.932 | −19.826 | 1.00 | 5.08 |
| ATOM | 2031 | CB | VAL | A | 408 | 15.821 | 3.073 | −21.089 | 1.00 | 5.40 |
| ATOM | 2032 | CG1 | VAL | A | 408 | 16.503 | 3.694 | −22.296 | 1.00 | 5.87 |
| ATOM | 2033 | CG2 | VAL | A | 408 | 16.324 | 1.649 | −20.882 | 1.00 | 5.54 |
| ATOM | 2034 | C | VAL | A | 408 | 15.758 | 5.382 | −19.983 | 1.00 | 5.05 |
| ATOM | 2035 | O | VAL | A | 408 | 16.653 | 6.159 | −20.399 | 1.00 | 4.96 |
| ATOM | 2036 | N | ALA | A | 409 | 14.529 | 5.817 | −19.689 | 1.00 | 5.38 |
| ATOM | 2037 | CA | ALA | A | 409 | 14.254 | 7.249 | −19.688 | 1.00 | 5.24 |
| ATOM | 2038 | CB | ALA | A | 409 | 12.782 | 7.481 | −19.311 | 1.00 | 5.22 |
| ATOM | 2039 | C | ALA | A | 409 | 15.182 | 8.015 | −18.770 | 1.00 | 5.02 |
| ATOM | 2040 | O | ALA | A | 409 | 15.628 | 9.128 | −19.130 | 1.00 | 6.44 |
| ATOM | 2041 | N | ALA | A | 410 | 15.502 | 7.473 | −17.610 | 1.00 | 5.06 |
| ATOM | 2042 | CA | ALA | A | 410 | 16.469 | 8.067 | −16.725 | 1.00 | 5.41 |
| ATOM | 2043 | CB | ALA | A | 410 | 16.425 | 7.401 | −15.333 | 1.00 | 5.91 |
| ATOM | 2044 | C | ALA | A | 410 | 17.845 | 8.056 | −17.316 | 1.00 | 5.75 |
| ATOM | 2045 | O | ALA | A | 410 | 18.588 | 9.072 | −17.096 | 1.00 | 6.84 |
| ATOM | 2046 | N | LEU | A | 411 | 18.291 | 7.025 | −17.993 | 1.00 | 5.45 |
| ATOM | 2047 | CA | LEU | A | 411 | 19.605 | 7.010 | −18.653 | 1.00 | 6.46 |
| ATOM | 2048 | CB | LEU | A | 411 | 19.901 | 5.686 | −19.299 | 1.00 | 6.18 |
| ATOM | 2049 | CG | LEU | A | 411 | 19.846 | 4.467 | −18.417 | 1.00 | 6.63 |
| ATOM | 2050 | CD1 | LEU | A | 411 | 20.325 | 3.235 | −19.173 | 1.00 | 7.08 |
| ATOM | 2051 | CD2 | LEU | A | 411 | 20.658 | 4.646 | −17.136 | 1.00 | 7.52 |
| ATOM | 2052 | C | LEU | A | 411 | 19.629 | 8.144 | −19.651 | 1.00 | 6.50 |
| ATOM | 2053 | O | LEU | A | 411 | 20.645 | 8.898 | −19.762 | 1.00 | 7.27 |
| ATOM | 2054 | N | ILE | A | 412 | 18.623 | 8.278 | −20.476 | 1.00 | 5.77 |
| ATOM | 2055 | CA | ILE | A | 412 | 18.505 | 9.355 | −21.444 | 1.00 | 5.97 |
| ATOM | 2056 | CB | ILE | A | 412 | 17.145 | 9.203 | −22.257 | 1.00 | 6.18 |
| ATOM | 2057 | CG1 | ILE | A | 412 | 17.189 | 8.011 | −23.142 | 1.00 | 6.34 |
| ATOM | 2058 | CD1 | ILE | A | 412 | 15.780 | 7.579 | −23.614 | 1.00 | 6.50 |
| ATOM | 2059 | CG2 | ILE | A | 412 | 16.839 | 10.490 | −22.988 | 1.00 | 6.87 |
| ATOM | 2060 | C | ILE | A | 412 | 18.600 | 10.653 | −20.774 | 1.00 | 6.44 |
| ATOM | 2061 | O | ILE | A | 412 | 19.309 | 11.595 | −21.315 | 1.00 | 7.45 |
| ATOM | 2062 | N | LYS | A | 413 | 17.914 | 10.913 | −19.683 | 1.00 | 6.35 |
| ATOM | 2063 | CA | LYS | A | 413 | 17.923 | 12.205 | −19.007 | 1.00 | 7.03 |
| ATOM | 2064 | CB | LYS | A | 413 | 16.830 | 12.243 | −17.930 | 1.00 | 7.67 |
| ATOM | 2065 | CG | LYS | A | 413 | 16.578 | 13.575 | −17.344 | 1.00 | 8.21 |
| ATOM | 2066 | CD | LYS | A | 413 | 15.950 | 14.540 | −18.325 | 1.00 | 9.83 |
| ATOM | 2067 | CE | LYS | A | 413 | 15.470 | 15.807 | −17.618 | 1.00 | 13.68 |
| ATOM | 2068 | NZ | LYS | A | 413 | 14.946 | 16.795 | −18.486 | 1.00 | 21.99 |
| ATOM | 2069 | C | LYS | A | 413 | 19.312 | 12.504 | −18.438 | 1.00 | 6.77 |
| ATOM | 2070 | O | LYS | A | 413 | 19.664 | 13.698 | −18.418 | 1.00 | 8.52 |
| ATOM | 2071 | N | GLN | A | 414 | 20.069 | 11.556 | −17.995 | 1.00 | 6.56 |
| ATOM | 2072 | CA | GLN | A | 414 | 21.472 | 11.845 | −17.577 | 1.00 | 7.27 |
| ATOM | 2073 | CB | GLN | A | 414 | 22.121 | 10.645 | −16.994 | 1.00 | 7.49 |
| ATOM | 2074 | CG | GLN | A | 414 | 23.585 | 10.911 | −16.575 | 1.00 | 7.79 |
| ATOM | 2075 | CD | GLN | A | 414 | 24.341 | 9.708 | −16.248 | 1.00 | 9.61 |
| ATOM | 2076 | OE1 | GLN | A | 414 | 23.861 | 8.619 | −16.029 | 1.00 | 9.10 |
| ATOM | 2077 | NE2 | GLN | A | 414 | 25.622 | 9.855 | −16.074 | 1.00 | 12.19 |
| ATOM | 2078 | C | GLN | A | 414 | 22.261 | 12.325 | −18.776 | 1.00 | 8.57 |
| ATOM | 2079 | O | GLN | A | 414 | 22.975 | 13.329 | −18.696 | 1.00 | 10.04 |
| ATOM | 2080 | N | ALA | A | 415 | 22.137 | 11.653 | −19.900 | 1.00 | 7.66 |
| ATOM | 2081 | CA | ALA | A | 415 | 22.903 | 12.014 | −21.121 | 1.00 | 8.36 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 2082 | CB | ALA | A | 415 | 22.806 | 10.894 | −22.121 | 1.00 | 9.35 |
| ATOM | 2083 | C | ALA | A | 415 | 22.434 | 13.308 | −21.689 | 1.00 | 8.81 |
| ATOM | 2084 | O | ALA | A | 415 | 23.258 | 14.053 | −22.304 | 1.00 | 11.11 |
| ATOM | 2085 | N | LYS | A | 416 | 21.185 | 13.684 | −21.603 | 1.00 | 9.15 |
| ATOM | 2086 | CA | LYS | A | 416 | 20.550 | 14.869 | −22.199 | 1.00 | 9.41 |
| ATOM | 2087 | CB | LYS | A | 416 | 19.728 | 14.425 | −23.408 | 1.00 | 10.67 |
| ATOM | 2088 | CG | LYS | A | 416 | 19.200 | 15.600 | −24.224 | 1.00 | 11.77 |
| ATOM | 2089 | CD | LYS | A | 416 | 18.465 | 15.092 | −25.470 | 1.00 | 15.03 |
| ATOM | 2090 | CE | LYS | A | 416 | 17.665 | 16.131 | −26.256 | 1.00 | 17.11 |
| ATOM | 2091 | NZ | LYS | A | 416 | 18.609 | 17.177 | −26.705 | 1.00 | 20.59 |
| ATOM | 2092 | C | LYS | A | 416 | 19.708 | 15.537 | −21.113 | 1.00 | 10.25 |
| ATOM | 2093 | O | LYS | A | 416 | 18.476 | 15.414 | −21.085 | 1.00 | 8.78 |
| ATOM | 2094 | N | PRO | A | 417 | 20.327 | 16.334 | −20.195 | 1.00 | 9.48 |
| ATOM | 2095 | CA | PRO | A | 417 | 19.619 | 16.834 | −19.068 | 1.00 | 9.79 |
| ATOM | 2096 | CB | PRO | A | 417 | 20.718 | 17.453 | −18.181 | 1.00 | 11.93 |
| ATOM | 2097 | CG | PRO | A | 417 | 21.988 | 16.966 | −18.681 | 1.00 | 16.04 |
| ATOM | 2098 | CD | PRO | A | 417 | 21.795 | 16.467 | −20.086 | 1.00 | 13.11 |
| ATOM | 2099 | C | PRO | A | 417 | 18.531 | 17.814 | −19.382 | 1.00 | 10.64 |
| ATOM | 2100 | O | PRO | A | 417 | 17.681 | 18.075 | −18.526 | 1.00 | 13.90 |
| ATOM | 2101 | N | ASP | A | 418 | 18.511 | 18.419 | −20.550 | 1.00 | 11.72 |
| ATOM | 2102 | CA | ASP | A | 418 | 17.411 | 19.290 | −20.936 | 1.00 | 12.79 |
| ATOM | 2103 | CB | ASP | A | 418 | 17.999 | 20.511 | −21.728 | 1.00 | 18.32 |
| ATOM | 2104 | CG | ASP | A | 418 | 18.480 | 20.151 | −23.150 | 1.00 | 23.99 |
| ATOM | 2105 | OD1 | ASP | A | 418 | 18.618 | 18.963 | −23.660 | 1.00 | 28.19 |
| ATOM | 2106 | OD2 | ASP | A | 418 | 18.853 | 21.136 | −23.899 | 1.00 | 31.60 |
| ATOM | 2107 | C | ASP | A | 418 | 16.365 | 18.617 | −21.804 | 1.00 | 11.74 |
| ATOM | 2108 | O | ASP | A | 418 | 15.468 | 19.249 | −22.312 | 1.00 | 11.92 |
| ATOM | 2109 | N | ALA | A | 419 | 16.434 | 17.281 | −21.856 | 1.00 | 10.77 |
| ATOM | 2110 | CA | ALA | A | 419 | 15.403 | 16.585 | −22.704 | 1.00 | 11.21 |
| ATOM | 2111 | CB | ALA | A | 419 | 15.706 | 15.083 | −22.738 | 1.00 | 11.26 |
| ATOM | 2112 | C | ALA | A | 419 | 13.965 | 16.770 | −22.238 | 1.00 | 9.90 |
| ATOM | 2113 | O | ALA | A | 419 | 13.734 | 16.670 | −21.011 | 1.00 | 11.77 |
| ATOM | 2114 | N | THR | A | 420 | 13.052 | 17.084 | −23.160 | 1.00 | 8.21 |
| ATOM | 2115 | CA | THR | A | 420 | 11.647 | 17.227 | −22.827 | 1.00 | 7.27 |
| ATOM | 2116 | CB | THR | A | 420 | 10.968 | 18.114 | −23.864 | 1.00 | 7.99 |
| ATOM | 2117 | OG1 | THR | A | 420 | 10.956 | 17.440 | −25.094 | 1.00 | 9.57 |
| ATOM | 2118 | CG2 | THR | A | 420 | 11.638 | 19.525 | −23.990 | 1.00 | 9.92 |
| ATOM | 2119 | C | THR | A | 420 | 10.952 | 15.869 | −22.808 | 1.00 | 7.75 |
| ATOM | 2120 | O | THR | A | 420 | 11.463 | 14.907 | −23.354 | 1.00 | 7.20 |
| ATOM | 2121 | N | PRO | A | 421 | 9.741 | 15.809 | −22.267 | 1.00 | 6.91 |
| ATOM | 2122 | CA | PRO | A | 421 | 9.030 | 14.542 | −22.321 | 1.00 | 7.18 |
| ATOM | 2123 | CB | PRO | A | 421 | 7.686 | 14.884 | −21.625 | 1.00 | 7.84 |
| ATOM | 2124 | CG | PRO | A | 421 | 8.106 | 15.914 | −20.598 | 1.00 | 9.17 |
| ATOM | 2125 | CD | PRO | A | 421 | 9.112 | 16.789 | −21.319 | 1.00 | 7.70 |
| ATOM | 2126 | C | PRO | A | 421 | 8.843 | 14.036 | −23.719 | 1.00 | 6.94 |
| ATOM | 2127 | O | PRO | A | 421 | 8.959 | 12.829 | −23.961 | 1.00 | 6.85 |
| ATOM | 2128 | N | ASP | A | 422 | 8.519 | 14.909 | −24.692 | 1.00 | 6.44 |
| ATOM | 2129 | CA | ASP | A | 422 | 8.360 | 14.452 | −26.035 | 1.00 | 7.05 |
| ATOM | 2130 | CB | ASP | A | 422 | 7.767 | 15.598 | −26.911 | 1.00 | 8.15 |
| ATOM | 2131 | CG | ASP | A | 422 | 6.339 | 15.787 | −26.642 | 1.00 | 11.35 |
| ATOM | 2132 | OD1 | ASP | A | 422 | 5.606 | 14.957 | −26.063 | 1.00 | 10.75 |
| ATOM | 2133 | OD2 | ASP | A | 422 | 5.815 | 16.849 | −27.063 | 1.00 | 15.59 |
| ATOM | 2134 | C | ASP | A | 422 | 9.649 | 14.017 | −26.645 | 1.00 | 6.66 |
| ATOM | 2135 | O | ASP | A | 422 | 9.688 | 12.998 | −27.371 | 1.00 | 7.08 |
| ATOM | 2136 | N | GLU | A | 423 | 10.767 | 14.621 | −26.312 | 1.00 | 6.12 |
| ATOM | 2137 | CA | GLU | A | 423 | 12.042 | 14.203 | −26.850 | 1.00 | 6.67 |
| ATOM | 2138 | CB | GLU | A | 423 | 13.168 | 15.180 | −26.533 | 1.00 | 8.75 |
| ATOM | 2139 | CG | GLU | A | 423 | 13.123 | 16.446 | −27.364 | 1.00 | 10.35 |
| ATOM | 2140 | CD | GLU | A | 423 | 14.034 | 17.503 | −26.862 | 1.00 | 12.60 |
| ATOM | 2141 | OE1 | GLU | A | 423 | 14.456 | 17.654 | −25.734 | 1.00 | 12.26 |
| ATOM | 2142 | OE2 | GLU | A | 423 | 14.325 | 18.354 | −27.781 | 1.00 | 18.79 |
| ATOM | 2143 | C | GLU | A | 423 | 12.432 | 12.852 | −26.256 | 1.00 | 6.54 |
| ATOM | 2144 | O | GLU | A | 423 | 12.970 | 11.971 | −26.968 | 1.00 | 7.50 |
| ATOM | 2145 | N | ILE | A | 424 | 12.180 | 12.575 | −24.974 | 1.00 | 6.43 |
| ATOM | 2146 | CA | ILE | A | 424 | 12.473 | 11.288 | −24.379 | 1.00 | 6.44 |
| ATOM | 2147 | CB | ILE | A | 424 | 12.390 | 11.314 | −22.859 | 1.00 | 6.56 |
| ATOM | 2148 | CG1 | ILE | A | 424 | 13.317 | 12.351 | −22.241 | 1.00 | 7.50 |
| ATOM | 2149 | CD1 | ILE | A | 424 | 13.138 | 12.541 | −20.740 | 1.00 | 9.21 |
| ATOM | 2150 | CG2 | ILE | A | 424 | 12.545 | 9.904 | −22.315 | 1.00 | 7.02 |
| ATOM | 2151 | C | ILE | A | 424 | 11.655 | 10.202 | −25.009 | 1.00 | 6.24 |
| ATOM | 2152 | O | ILE | A | 424 | 12.201 | 9.142 | −25.379 | 1.00 | 5.94 |
| ATOM | 2153 | N | GLU | A | 425 | 10.362 | 10.429 | −25.170 | 1.00 | 5.37 |
| ATOM | 2154 | CA | GLU | A | 425 | 9.527 | 9.441 | −25.849 | 1.00 | 6.14 |
| ATOM | 2155 | CB | GLU | A | 425 | 8.068 | 9.900 | −25.874 | 1.00 | 6.26 |
| ATOM | 2156 | CG | GLU | A | 425 | 7.149 | 8.936 | −26.591 | 1.00 | 6.56 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 2157 | CD | GLU | A | 425 | 5.714 | 9.151 | −26.375 | 1.00 | 6.68 |
| ATOM | 2158 | OE1 | GLU | A | 425 | 5.291 | 10.164 | −25.795 | 1.00 | 8.38 |
| ATOM | 2159 | OE2 | GLU | A | 425 | 4.907 | 8.280 | −26.808 | 1.00 | 7.91 |
| ATOM | 2160 | C | GLU | A | 425 | 10.065 | 9.167 | −27.260 | 1.00 | 6.41 |
| ATOM | 2161 | O | GLU | A | 425 | 10.118 | 8.024 | −27.727 | 1.00 | 5.98 |
| ATOM | 2162 | N | SER | A | 426 | 10.383 | 10.248 | −27.983 | 1.00 | 6.62 |
| ATOM | 2163 | CA | SER | A | 426 | 10.915 | 10.066 | −29.365 | 1.00 | 6.85 |
| ATOM | 2164 | CB | SER | A | 426 | 11.069 | 11.399 | −29.997 | 1.00 | 7.67 |
| ATOM | 2165 | OG | SER | A | 426 | 11.535 | 11.139 | −31.363 | 1.00 | 10.25 |
| ATOM | 2166 | C | SER | A | 426 | 12.177 | 9.266 | −29.361 | 1.00 | 6.57 |
| ATOM | 2167 | O | SER | A | 426 | 12.355 | 8.358 | −30.218 | 1.00 | 6.87 |
| ATOM | 2168 | N | ILE | A | 427 | 13.113 | 9.503 | −28.495 | 1.00 | 6.43 |
| ATOM | 2169 | CA | ILE | A | 427 | 14.352 | 8.740 | −28.435 | 1.00 | 6.80 |
| ATOM | 2170 | CB | ILE | A | 427 | 15.370 | 9.352 | −27.400 | 1.00 | 6.80 |
| ATOM | 2171 | CG1 | ILE | A | 427 | 15.890 | 10.674 | −27.910 | 1.00 | 7.21 |
| ATOM | 2172 | CD1 | ILE | A | 427 | 16.525 | 11.558 | −26.848 | 1.00 | 8.19 |
| ATOM | 2173 | CG2 | ILE | A | 427 | 16.502 | 8.384 | −27.141 | 1.00 | 6.81 |
| ATOM | 2174 | C | ILE | A | 427 | 14.074 | 7.303 | −28.137 | 1.00 | 6.44 |
| ATOM | 2175 | O | ILE | A | 427 | 14.590 | 6.377 | −28.811 | 1.00 | 6.82 |
| ATOM | 2176 | N | LEU | A | 428 | 13.205 | 6.997 | −27.165 | 1.00 | 6.08 |
| ATOM | 2177 | CA | LEU | A | 428 | 12.851 | 5.612 | −26.813 | 1.00 | 5.80 |
| ATOM | 2178 | CB | LEU | A | 428 | 11.852 | 5.594 | −25.704 | 1.00 | 6.09 |
| ATOM | 2179 | CG | LEU | A | 428 | 12.406 | 5.931 | −24.271 | 1.00 | 6.74 |
| ATOM | 2180 | CD1 | LEU | A | 428 | 11.233 | 6.197 | −23.330 | 1.00 | 6.27 |
| ATOM | 2181 | CD2 | LEU | A | 428 | 13.294 | 4.805 | −23.704 | 1.00 | 7.01 |
| ATOM | 2182 | C | LEU | A | 428 | 12.274 | 4.921 | −28.014 | 1.00 | 5.65 |
| ATOM | 2183 | O | LEU | A | 428 | 12.633 | 3.779 | −28.331 | 1.00 | 6.90 |
| ATOM | 2184 | N | LYS | A | 429 | 11.315 | 5.543 | −28.718 | 1.00 | 5.38 |
| ATOM | 2185 | CA | LYS | A | 429 | 10.595 | 4.941 | −29.842 | 1.00 | 6.49 |
| ATOM | 2186 | CB | LYS | A | 429 | 9.391 | 5.770 | −30.194 | 1.00 | 7.23 |
| ATOM | 2187 | CG | LYS | A | 429 | 8.306 | 5.715 | −29.112 | 1.00 | 7.72 |
| ATOM | 2188 | CD | LYS | A | 429 | 7.010 | 6.502 | −29.494 | 1.00 | 8.80 |
| ATOM | 2189 | CE | LYS | A | 429 | 6.322 | 5.785 | −30.600 | 1.00 | 8.82 |
| ATOM | 2190 | NZ | LYS | A | 429 | 4.922 | 6.308 | −30.697 | 1.00 | 10.82 |
| ATOM | 2191 | C | LYS | A | 429 | 11.509 | 4.800 | −31.056 | 1.00 | 6.51 |
| ATOM | 2192 | O | LYS | A | 429 | 11.388 | 3.841 | −31.798 | 1.00 | 7.02 |
| ATOM | 2193 | N | SER | A | 430 | 12.405 | 5.743 | −31.262 | 1.00 | 6.54 |
| ATOM | 2194 | CA | SER | A | 430 | 13.165 | 5.771 | −32.539 | 1.00 | 6.25 |
| ATOM | 2195 | CB | SER | A | 430 | 13.554 | 7.208 | −32.868 | 1.00 | 7.79 |
| ATOM | 2196 | OG | SER | A | 430 | 12.500 | 8.159 | −32.903 | 1.00 | 10.01 |
| ATOM | 2197 | C | SER | A | 430 | 14.362 | 4.888 | −32.518 | 1.00 | 6.56 |
| ATOM | 2198 | O | SER | A | 430 | 14.966 | 4.687 | −33.578 | 0.50 | 2.40 |
| ATOM | 2199 | N | THR | A | 431 | 14.790 | 4.375 | −31.358 | 1.00 | 6.09 |
| ATOM | 2200 | CA | THR | A | 431 | 16.001 | 3.590 | −31.217 | 1.00 | 6.75 |
| ATOM | 2201 | CB | THR | A | 431 | 16.974 | 4.240 | −30.206 | 1.00 | 6.96 |
| ATOM | 2202 | OG1 | THR | A | 431 | 16.361 | 4.240 | −28.911 | 1.00 | 6.77 |
| ATOM | 2203 | CG2 | THR | A | 431 | 17.327 | 5.634 | −30.620 | 1.00 | 7.20 |
| ATOM | 2204 | C | THR | A | 431 | 15.769 | 2.140 | −30.840 | 1.00 | 6.18 |
| ATOM | 2205 | O | THR | A | 431 | 16.692 | 1.436 | −30.469 | 1.00 | 7.07 |
| ATOM | 2206 | N | THR | A | 432 | 14.520 | 1.689 | −30.898 | 1.00 | 5.57 |
| ATOM | 2207 | CA | THR | A | 432 | 14.233 | 0.316 | −30.537 | 1.00 | 5.90 |
| ATOM | 2208 | CB | THR | A | 432 | 12.731 | 0.022 | −30.505 | 1.00 | 5.68 |
| ATOM | 2209 | OG1 | THR | A | 432 | 12.161 | 0.374 | −31.778 | 1.00 | 6.07 |
| ATOM | 2210 | CG2 | THR | A | 432 | 12.006 | 0.742 | −29.449 | 1.00 | 6.11 |
| ATOM | 2211 | C | THR | A | 432 | 14.882 | −0.662 | −31.572 | 1.00 | 5.96 |
| ATOM | 2212 | O | THR | A | 432 | 15.170 | −0.280 | −32.729 | 1.00 | 6.22 |
| ATOM | 2213 | N | ARG | A | 433 | 15.022 | −1.863 | −31.135 | 1.00 | 5.81 |
| ATOM | 2214 | CA | ARG | A | 433 | 15.557 | −2.947 | −31.962 | 1.00 | 6.25 |
| ATOM | 2215 | CB | ARG | A | 433 | 16.683 | −3.717 | −31.232 | 1.00 | 8.52 |
| ATOM | 2216 | CG | ARG | A | 433 | 16.184 | −4.652 | −30.087 | 1.00 | 10.34 |
| ATOM | 2217 | CD | ARG | A | 433 | 17.231 | −5.356 | −29.343 | 1.00 | 12.25 |
| ATOM | 2218 | NE | ARG | A | 433 | 16.576 | −6.050 | −28.273 | 1.00 | 11.04 |
| ATOM | 2219 | CZ | ARG | A | 433 | 16.180 | −7.264 | −28.174 | 1.00 | 9.82 |
| ATOM | 2220 | NH1 | ARG | A | 433 | 15.917 | −8.082 | −29.223 | 1.00 | 10.18 |
| ATOM | 2221 | NH2 | ARG | A | 433 | 15.928 | −7.758 | −26.988 | 1.00 | 8.10 |
| ATOM | 2222 | C | ARG | A | 433 | 14.446 | −3.905 | −32.335 | 1.00 | 6.54 |
| ATOM | 2223 | O | ARG | A | 433 | 13.319 | −3.866 | −31.847 | 1.00 | 7.19 |
| ATOM | 2224 | N | SER | A | 434 | 14.722 | −4.767 | −33.331 | 1.00 | 6.96 |
| ATOM | 2225 | CA | SER | A | 434 | 13.769 | −5.689 | −33.881 | 1.00 | 7.43 |
| ATOM | 2226 | CB | SER | A | 434 | 14.353 | −6.432 | −35.120 | 1.00 | 8.35 |
| ATOM | 2227 | OG | SER | A | 434 | 14.627 | −5.522 | −36.200 | 1.00 | 10.99 |
| ATOM | 2228 | C | SER | A | 434 | 13.287 | −6.714 | −32.863 | 1.00 | 6.79 |
| ATOM | 2229 | O | SER | A | 434 | 14.032 | −7.145 | −31.998 | 1.00 | 7.37 |
| ATOM | 2230 | N | PHE | A | 435 | 12.105 | −7.197 | −33.139 | 1.00 | 6.80 |
| ATOM | 2231 | CA | PHE | A | 435 | 11.556 | −8.327 | −32.412 | 1.00 | 6.87 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 2232 | CB | PHE | A | 435 | 10.035 | −8.346 | −32.464 | 1.00 | 7.80 |
| ATOM | 2233 | CG | PHE | A | 435 | 9.355 | −7.199 | −31.764 | 1.00 | 7.41 |
| ATOM | 2234 | CD1 | PHE | A | 435 | 9.276 | −7.148 | −30.391 | 1.00 | 7.38 |
| ATOM | 2235 | CE1 | PHE | A | 435 | 8.627 | −6.062 | −29.814 | 1.00 | 7.96 |
| ATOM | 2236 | CZ | PHE | A | 435 | 8.102 | −5.054 | −30.600 | 1.00 | 7.41 |
| ATOM | 2237 | CE2 | PHE | A | 435 | 8.187 | −5.105 | −31.921 | 1.00 | 8.15 |
| ATOM | 2238 | CD2 | PHE | A | 435 | 8.791 | −6.197 | −32.514 | 1.00 | 7.70 |
| ATOM | 2239 | C | PHE | A | 435 | 12.101 | −9.658 | −33.006 | 1.00 | 7.63 |
| ATOM | 2240 | O | PHE | A | 435 | 11.855 | −9.884 | −34.178 | 1.00 | 10.06 |
| ATOM | 2241 | N | PRO | A | 436 | 12.698 | −10.497 | −32.221 | 1.00 | 8.01 |
| ATOM | 2242 | CA | PRO | A | 436 | 13.164 | −11.805 | −32.819 | 1.00 | 9.27 |
| ATOM | 2243 | CB | PRO | A | 436 | 14.280 | −12.217 | −31.889 | 1.00 | 11.50 |
| ATOM | 2244 | CG | PRO | A | 436 | 14.114 | −11.504 | −30.665 | 1.00 | 11.68 |
| ATOM | 2245 | CD | PRO | A | 436 | 13.365 | −10.206 | −30.912 | 1.00 | 8.73 |
| ATOM | 2246 | C | PRO | A | 436 | 12.061 | −12.784 | −32.868 | 1.00 | 9.59 |
| ATOM | 2247 | O | PRO | A | 436 | 12.333 | −13.865 | −33.471 | 1.00 | 12.13 |
| ATOM | 2248 | N | ALA | A | 437 | 10.911 | −12.569 | −32.274 | 1.00 | 8.84 |
| ATOM | 2249 | CA | ALA | A | 437 | 9.777 | −13.415 | −32.355 | 1.00 | 9.19 |
| ATOM | 2250 | CB | ALA | A | 437 | 9.707 | −14.358 | −31.155 | 1.00 | 8.71 |
| ATOM | 2251 | C | ALA | A | 437 | 8.547 | −12.537 | −32.486 | 1.00 | 11.27 |
| ATOM | 2252 | O | ALA | A | 437 | 8.594 | −11.340 | −32.091 | 1.00 | 10.81 |
| ATOM | 2253 | N | THR | A | 438 | 7.440 | −13.112 | −32.869 | 1.00 | 12.16 |
| ATOM | 2254 | CA | THR | A | 438 | 6.221 | −12.365 | −33.195 | 1.00 | 14.12 |
| ATOM | 2255 | CB | THR | A | 438 | 5.008 | −13.386 | −33.292 | 1.00 | 16.04 |
| ATOM | 2256 | OG1 | THR | A | 438 | 5.321 | −14.495 | −34.217 | 1.00 | 20.59 |
| ATOM | 2257 | CG2 | THR | A | 438 | 3.713 | −12.721 | −33.775 | 1.00 | 18.23 |
| ATOM | 2258 | C | THR | A | 438 | 5.847 | −11.389 | −32.004 | 1.00 | 11.16 |
| ATOM | 2259 | O | THR | A | 438 | 5.695 | −11.861 | −30.879 | 1.00 | 10.19 |
| ATOM | 2260 | N | CYS | A | 439 | 5.610 | −10.130 | −32.395 | 1.00 | 12.10 |
| ATOM | 2261 | CA | CYS | A | 439 | 5.018 | −9.171 | −31.441 | 1.00 | 10.50 |
| ATOM | 2262 | CB | CYS | A | 439 | 6.092 | −8.464 | −30.609 | 1.00 | 11.24 |
| ATOM | 2263 | SG | CYS | A | 439 | 5.618 | −7.915 | −28.974 | 1.00 | 10.33 |
| ATOM | 2264 | C | CYS | A | 439 | 4.138 | −8.230 | −32.242 | 1.00 | 12.27 |
| ATOM | 2265 | O | CYS | A | 439 | 4.649 | −7.192 | −32.684 | 1.00 | 13.32 |
| ATOM | 2266 | N | THR | A | 440 | 2.849 | −8.625 | −32.303 | 1.00 | 14.51 |
| ATOM | 2267 | CA | THR | A | 440 | 1.972 | −7.830 | −33.137 | 1.00 | 15.73 |
| ATOM | 2268 | CB | THR | A | 440 | 0.929 | −8.613 | −33.994 | 1.00 | 22.57 |
| ATOM | 2269 | OG1 | THR | A | 440 | −0.429 | −8.121 | −33.938 | 1.00 | 32.58 |
| ATOM | 2270 | CG2 | THR | A | 440 | 0.986 | −10.109 | −33.846 | 1.00 | 20.48 |
| ATOM | 2271 | C | THR | A | 440 | 1.476 | −6.618 | −32.343 | 1.00 | 11.35 |
| ATOM | 2272 | O | THR | A | 440 | 0.995 | −6.723 | −31.238 | 1.00 | 12.33 |
| ATOM | 2273 | N | SER | A | 441 | 1.594 | −5.535 | −33.013 | 1.00 | 10.79 |
| ATOM | 2274 | CA | SER | A | 441 | 1.163 | −4.245 | −32.434 | 1.00 | 9.15 |
| ATOM | 2275 | CB | SER | A | 441 | −0.302 | −4.159 | −32.369 | 1.00 | 9.92 |
| ATOM | 2276 | OG | SER | A | 441 | −0.904 | −4.274 | −33.703 | 1.00 | 15.04 |
| ATOM | 2277 | C | SER | A | 441 | 1.761 | −3.932 | −31.061 | 1.00 | 9.15 |
| ATOM | 2278 | O | SER | A | 441 | 1.073 | −3.632 | −30.097 | 1.00 | 8.35 |
| ATOM | 2279 | N | CYS | A | 442 | 3.068 | −4.115 | −31.027 | 1.00 | 8.21 |
| ATOM | 2280 | CA | CYS | A | 442 | 3.895 | −4.002 | −29.833 | 1.00 | 8.21 |
| ATOM | 2281 | CB | CYS | A | 442 | 4.804 | −5.172 | −29.670 | 1.00 | 7.84 |
| ATOM | 2282 | SG | CYS | A | 442 | 3.967 | −6.715 | −29.278 | 1.00 | 10.08 |
| ATOM | 2283 | C | CYS | A | 442 | 4.752 | −2.743 | −29.882 | 1.00 | 7.62 |
| ATOM | 2284 | O | CYS | A | 442 | 5.840 | −2.670 | −29.229 | 1.00 | 7.69 |
| ATOM | 2285 | N | GLY | A | 443 | 4.346 | −1.706 | −30.591 | 1.00 | 7.48 |
| ATOM | 2286 | CA | GLY | A | 443 | 5.114 | −0.498 | −30.718 | 1.00 | 7.30 |
| ATOM | 2287 | C | GLY | A | 443 | 6.237 | −0.701 | −31.698 | 1.00 | 7.40 |
| ATOM | 2288 | O | GLY | A | 443 | 6.243 | −1.613 | −32.521 | 1.00 | 8.22 |
| ATOM | 2289 | N | THR | A | 444 | 7.254 | 0.155 | −31.645 | 1.00 | 6.09 |
| ATOM | 2290 | CA | THR | A | 444 | 8.235 | 0.209 | −32.733 | 1.00 | 6.11 |
| ATOM | 2291 | CB | THR | A | 444 | 8.947 | 1.558 | −32.775 | 1.00 | 6.79 |
| ATOM | 2292 | OG1 | THR | A | 444 | 9.742 | 1.689 | −31.590 | 1.00 | 6.54 |
| ATOM | 2293 | CG2 | THR | A | 444 | 7.983 | 2.703 | −32.876 | 1.00 | 7.76 |
| ATOM | 2294 | C | THR | A | 444 | 9.215 | −0.891 | −32.618 | 1.00 | 6.16 |
| ATOM | 2295 | O | THR | A | 444 | 10.009 | −1.092 | −33.606 | 1.00 | 7.17 |
| ATOM | 2296 | N | GLY | A | 445 | 9.383 | −1.559 | −31.479 | 1.00 | 5.46 |
| ATOM | 2297 | CA | GLY | A | 445 | 10.462 | −2.522 | −31.258 | 1.00 | 5.45 |
| ATOM | 2298 | C | GLY | A | 445 | 10.664 | −2.707 | −29.754 | 1.00 | 5.51 |
| ATOM | 2299 | O | GLY | A | 445 | 9.863 | −2.152 | −28.975 | 1.00 | 5.68 |
| ATOM | 2300 | N | ILE | A | 446 | 11.708 | −3.423 | −29.411 | 1.00 | 4.79 |
| ATOM | 2301 | CA | ILE | A | 446 | 12.116 | −3.597 | −28.006 | 1.00 | 5.25 |
| ATOM | 2302 | CB | ILE | A | 446 | 12.767 | −4.946 | −27.768 | 1.00 | 5.78 |
| ATOM | 2303 | CG1 | ILE | A | 446 | 11.768 | −6.077 | −28.065 | 1.00 | 6.35 |
| ATOM | 2304 | CD1 | ILE | A | 446 | 12.373 | −7.446 | −28.204 | 1.00 | 6.58 |
| ATOM | 2305 | CG2 | ILE | A | 446 | 13.356 | −5.072 | −26.336 | 1.00 | 6.38 |
| ATOM | 2306 | C | ILE | A | 446 | 13.094 | −2.465 | −27.681 | 1.00 | 5.40 |

TABLE 1-continued

Three-dimensional crystalline structure of cold-adapted protease including amino acid sequences SEQ ID NO: 10

| A | B | C | D | E | F | G | H | I | J | K |
|---|---|---|---|---|---|---|---|---|---|---|
| ATOM | 2307 | O | ILE | A | 446 | 14.051 | −2.197 | −28.416 | 1.00 | 5.32 |
| ATOM | 2308 | N | VAL | A | 447 | 12.859 | −1.768 | −26.572 | 1.00 | 4.77 |
| ATOM | 2309 | CA | VAL | A | 447 | 13.778 | −0.711 | −26.129 | 1.00 | 5.62 |
| ATOM | 2310 | CB | VAL | A | 447 | 13.299 | −0.114 | −24.774 | 1.00 | 5.69 |
| ATOM | 2311 | CG1 | VAL | A | 447 | 14.394 | 0.769 | −24.142 | 1.00 | 6.30 |
| ATOM | 2312 | CG2 | VAL | A | 447 | 12.025 | 0.632 | −24.986 | 1.00 | 6.38 |
| ATOM | 2313 | C | VAL | A | 447 | 15.226 | −1.247 | −26.057 | 1.00 | 5.74 |
| ATOM | 2314 | O | VAL | A | 447 | 15.440 | −2.328 | −25.521 | 1.00 | 5.65 |
| ATOM | 2315 | N | ASP | A | 448 | 16.100 | −0.427 | −26.630 | 1.00 | 6.18 |
| ATOM | 2316 | CA | ASP | A | 448 | 17.519 | −0.764 | −26.680 | 1.00 | 6.89 |
| ATOM | 2317 | CB | ASP | A | 448 | 17.957 | −0.846 | −28.172 | 1.00 | 7.68 |
| ATOM | 2318 | CG | ASP | A | 448 | 19.408 | −1.082 | −28.355 | 1.00 | 10.42 |
| ATOM | 2319 | OD1 | ASP | A | 448 | 20.237 | −0.899 | −27.430 | 1.00 | 9.43 |
| ATOM | 2320 | OD2 | ASP | A | 448 | 19.801 | −1.471 | −29.524 | 1.00 | 11.71 |
| ATOM | 2321 | C | ASP | A | 448 | 18.246 | 0.315 | −25.947 | 1.00 | 6.10 |
| ATOM | 2322 | O | ASP | A | 448 | 18.391 | 1.417 | −26.384 | 1.00 | 6.60 |
| ATOM | 2323 | N | ALA | A | 449 | 18.637 | −0.058 | −24.711 | 1.00 | 5.94 |
| ATOM | 2324 | CA | ALA | A | 449 | 19.209 | 1.002 | −23.826 | 1.00 | 6.13 |
| ATOM | 2325 | CB | ALA | A | 449 | 19.563 | 0.417 | −22.503 | 1.00 | 6.67 |
| ATOM | 2326 | C | ALA | A | 449 | 20.440 | 1.632 | −24.448 | 1.00 | 6.79 |
| ATOM | 2327 | O | ALA | A | 449 | 20.639 | 2.833 | −24.321 | 1.00 | 7.24 |
| ATOM | 2328 | N | ALA | A | 450 | 21.304 | 0.814 | −24.995 | 1.00 | 6.48 |
| ATOM | 2329 | CA | ALA | A | 450 | 22.575 | 1.362 | −25.592 | 1.00 | 7.18 |
| ATOM | 2330 | CB | ALA | A | 450 | 23.479 | 0.268 | −26.054 | 1.00 | 7.98 |
| ATOM | 2331 | C | ALA | A | 450 | 22.322 | 2.332 | −26.711 | 1.00 | 6.36 |
| ATOM | 2332 | O | ALA | A | 450 | 22.888 | 3.445 | −26.767 | 1.00 | 8.44 |
| ATOM | 2333 | N | ALA | A | 451 | 21.365 | 1.971 | −27.602 | 1.00 | 7.06 |
| ATOM | 2334 | CA | ALA | A | 451 | 21.049 | 2.839 | −28.700 | 1.00 | 6.77 |
| ATOM | 2335 | CB | ALA | A | 451 | 20.201 | 2.109 | −29.744 | 1.00 | 7.45 |
| ATOM | 2336 | C | ALA | A | 451 | 20.370 | 4.134 | −28.271 | 1.00 | 7.10 |
| ATOM | 2337 | O | ALA | A | 451 | 20.566 | 5.192 | −28.814 | 1.00 | 7.94 |
| ATOM | 2338 | N | ALA | A | 452 | 19.477 | 4.036 | −27.267 | 1.00 | 7.11 |
| ATOM | 2339 | CA | ALA | A | 452 | 18.844 | 5.166 | −26.716 | 1.00 | 7.05 |
| ATOM | 2340 | CB | ALA | A | 452 | 17.762 | 4.738 | −25.680 | 1.00 | 7.60 |
| ATOM | 2341 | C | ALA | A | 452 | 19.841 | 6.166 | −26.098 | 1.00 | 6.88 |
| ATOM | 2342 | O | ALA | A | 452 | 19.726 | 7.334 | −26.328 | 1.00 | 6.94 |
| ATOM | 2343 | N | VAL | A | 453 | 20.783 | 5.627 | −25.291 | 1.00 | 7.38 |
| ATOM | 2344 | CA | VAL | A | 453 | 21.789 | 6.513 | −24.705 | 1.00 | 8.19 |
| ATOM | 2345 | CB | VAL | A | 453 | 22.573 | 5.726 | −23.682 | 1.00 | 9.35 |
| ATOM | 2346 | CG1 | VAL | A | 453 | 23.891 | 6.385 | −23.283 | 1.00 | 10.30 |
| ATOM | 2347 | CG2 | VAL | A | 453 | 21.730 | 5.394 | −22.445 | 1.00 | 8.50 |
| ATOM | 2348 | C | VAL | A | 453 | 22.659 | 7.155 | −25.797 | 1.00 | 8.69 |
| ATOM | 2349 | O | VAL | A | 453 | 22.933 | 8.358 | −25.674 | 1.00 | 10.09 |
| ATOM | 2350 | N | ALA | A | 454 | 23.022 | 6.384 | −26.806 | 1.00 | 8.00 |
| ATOM | 2351 | CA | ALA | A | 454 | 23.758 | 6.955 | −27.925 | 1.00 | 8.10 |
| ATOM | 2352 | CB | ALA | A | 454 | 24.087 | 5.895 | −28.941 | 1.00 | 9.46 |
| ATOM | 2353 | C | ALA | A | 454 | 23.018 | 8.078 | −28.583 | 1.00 | 9.26 |
| ATOM | 2354 | O | ALA | A | 454 | 23.567 | 9.156 | −28.916 | 1.00 | 10.25 |
| ATOM | 2355 | N | ALA | A | 455 | 21.713 | 7.924 | −28.779 | 1.00 | 8.78 |
| ATOM | 2356 | CA | ALA | A | 455 | 20.900 | 8.954 | −29.382 | 1.00 | 8.33 |
| ATOM | 2357 | CB | ALA | A | 455 | 19.513 | 8.380 | −29.804 | 1.00 | 9.67 |
| ATOM | 2358 | C | ALA | A | 455 | 20.694 | 10.155 | −28.531 | 1.00 | 9.32 |
| ATOM | 2359 | O | ALA | A | 455 | 20.446 | 11.260 | −29.059 | 1.00 | 12.53 |
| ATOM | 2360 | N | ALA | A | 456 | 20.815 | 10.010 | −27.218 | 1.00 | 9.27 |
| ATOM | 2361 | CA | ALA | A | 456 | 20.657 | 11.137 | −26.325 | 1.00 | 10.15 |
| ATOM | 2362 | CB | ALA | A | 456 | 20.200 | 10.564 | −24.993 | 1.00 | 10.18 |
| ATOM | 2363 | C | ALA | A | 456 | 22.011 | 11.833 | −26.080 | 1.00 | 12.46 |
| ATOM | 2364 | O | ALA | A | 456 | 22.023 | 12.825 | −25.388 | 1.00 | 15.16 |
| ATOM | 2365 | N | SER | A | 457 | 23.122 | 11.287 | −26.551 | 1.00 | 12.94 |
| ATOM | 2366 | CA | SER | A | 457 | 24.543 | 11.722 | −26.369 | 1.00 | 15.79 |
| ATOM | 2367 | CB | SER | A | 457 | 25.042 | 12.858 | −27.243 | 1.00 | 21.74 |
| ATOM | 2368 | OG | SER | A | 457 | 24.369 | 12.859 | −28.485 | 1.00 | 22.46 |
| ATOM | 2369 | C | SER | A | 457 | 25.442 | 10.593 | −25.978 | 1.00 | 14.19 |
| ATOM | 2370 | O | SER | A | 457 | 25.112 | 9.837 | −24.931 | 1.00 | 16.08 |
| HETATM | 2371 | CA | CA | C | 1 | 22.679 | −5.208 | −5.643 | 1.00 | 6.61 |
| HETATM | 2372 | CA | CA | C | 2 | −2.136 | 6.605 | 5.488 | 1.00 | 7.73 |
| HETATM | 2373 | CA | CA | C | 3 | 1.597 | 5.590 | 4.829 | 1.00 | 6.15 |
| HETATM | 2374 | CA | CA | C | 4 | 2.532 | 7.587 | −26.583 | 1.00 | 6.29 |

In Table 1, A: atom; B: atomic number; C: atomic name; D: residue name; E: chain name; F: residue number; G: x-axis information; H: y-axis information; I: z-axis information; J: occupancy; and K: temperature factor.

In another aspect, the present invention is directed to a method for crystallizing a cold-adapted protease derived from *Pseudoalteromonas arctica* PAMC 21717 or a recombinant cold-adapted protease obtained by expressing a gene encoding the cold-adapted protease in *E. coli*, wherein the method comprises crystallizing at 20° C. using a protein solution containing 20 mM Tris-HCl (pH 8.0) and 150 mM NaCl, and a preservative solution containing 0.1 M sodium acetate (pH 4.4) and 3 M sodium chloride.

This crystallization step is generally performed using x-ray crystallography, and various crystallization processes should be performed as a pretreatment step prior to x-ray crystallography. In an embodiment of the present invention, a conventional method based on concentration equilibrium may be used as this crystallization method. For example, a vapor equilibrium method, a sitting- or handing-drop vapor diffusion method or a dialysis method (continuous or batch) may be used. In an example of the present invention, the sitting method was used to crystallize and concentrate the cold-adapted protease.

In still another aspect, the present invention is directed to a method for preparing a cold-adapted protease, the method comprises: (a) fed-batch-culturing *Pseudoalteromonas arctica* PAMC 21717 in a medium containing skim milk, tryptone, $Fe(C_6H_5O_7)$, NaCl, $MgCl_2$, $Na_2SO_4$, $CaCl_2$, $NaHCO_3$ and KBr, to produce a cold-adapted protease (W-pro21717); and (b) recovering the produced cold-adapted protease.

In yet another aspect, the present invention is directed to a method for preparing an enzyme-producing recombinant microorganism that expresses a cold-adapted protease, the method comprises: (a) performing PCR with a set of primers of SEQ ID NOs: 7 and 8, to obtain a gene encoding a cold-adapted protease (W-pro21717) derived from *Pseudoalteromonas arctica* PAMC 21717; (b) inserting the gene into a recombinant expression vector pEXP5-CT/TOPO; and (c) transforming host *E. coli* with the recombinant expression vector.

As used herein, the term "vector" refers to a DNA construct containing a DNA sequence operably linked to a suitable control sequence capable of expressing the DNA in a suitable host. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. For the purpose of the present invention, a plasmid vector is preferably used. A typical plasmid vector that can be used for this purpose has: (a) a replication origin by which replication occurs efficiently such that several hundred plasmid vectors per host cell are created; (b) an antibiotic-resistant gene by which host cells transformed with the plasmid vector can be selected; and (c) restriction enzyme digestion sites into which foreign DNA fragments can be inserted. Even if suitable restriction enzyme digestion sites are not present in the vector, the use of a conventional synthetic oligonucleotide adaptor or linker enables easy ligation between the vector and a foreign DNA.

After ligation, the vector should be transformed into suitable host cells. The transformation can be easily achieved using the calcium chloride method described in section 1.82 of Sambrook, et al., supra. Alternatively, electroporation (Neumann, et al., *EMBO J.*, 1:841, 1982) may also be used for the transformation of such cells.

For the overexpression of the gene according to the present invention, an expression vector known in the art may be used.

As well-known to the art, in order to increase the expression level of a transformed gene in a host cell, the gene should be operably linked to transcription and translation control sequences which can function in a selected expression host. Preferably, the corresponding gene and expression control sequence are contained in a single expression vector comprising both a bacterial selectable marker and a replication origin.

The host cell transformed with the above-described recombinant vector constitutes another aspect of the present invention. As used herein, the term "transformation" refers to introducing DNA into a host cell so that the DNA is replicable by either as a chromosomal integrant or as an extrachromosomal element.

Of course, it should be understood that all vectors do not function equally to express the DNA sequence of the present invention. Likewise, all host cells do not function equally for the same expression system. However, any person skilled in the art may properly select a vector, an expression control sequence and a host cell without departing from the scope of the present invention and without undue experimentation. For example, in selection of a vector, a host cell should be taken into consideration, because the vector should be replicated therein. Also, the replication number of a vector, the capability to control the replication number, and the expression of other proteins encoded by the vector, for example, an antibiotic marker, should be taken into consideration.

The recombinant vector that is used in the present invention is preferably a pDOC vector comprising pro21717-I gene introduced in pEXP5-CT/TOPO, and more preferably pDOC131. The recombinant microorganism is preferably *E. coli*, such as *E. coli* DH5α, *E. coli* JM101, *E. coli* K12, *E. coli* W3110, *E. coli* X1776, *E. coli* XL-1 Blue (Stratagene), *E. coli* BL21 or the like.

In a further aspect, the present invention is directed to a method for preparing a cold-adapted protease, the method comprises: (a) culturing the recombinant microorganism of claim 6 in a medium containing glucose, $KH_2PO_4$, $(NH_4)_2PO_4$, citric acid, $MgSO_4 7H_2O$, thiamine, an antibiotic and a trace metal element; (b) expressing a cold-adapted protease in the recombinant microorganism to a pH-stat batch culture while supplying a predetermined amount of a medium containing glucose, a yeast extract, $(NH_4)_2PO_4$, $MgSO_4 7H_2O$ and an antibiotic when the pH and DO of the medium is increased; and (c) recovering the expressed cold-adapted protease.

In the present invention, the protease is characterized in that it exhibits enzymatic activity under the conditions of 0 to 60° C. and pH 5.0 to 11.0, and is purified by a Sephacryl S-100 column using an unfolding buffer (pH 8.5; 8 M urea, 50 mM mercaptoethanol and 20 mM Tris-HCl), a refolding buffer (20 mM Tris-HCl, 100 mM NaCl, 20 mM $CaCl_2$ and 0.05% Tween 20), and a dialysis step.

In a still further aspect, the present invention is directed to a disinfectant composition for a surgical or therapeutic device, a detergent composition, a feed additive composition, a food additive composition, and a fiber or leather processing composition, the composition containing the cold-adapted protease or a crystal of the cold-adapted protease as an active ingredient.

The protease according to the present invention may be used as a disinfectant for a surgical or therapeutic device. The surgical or therapeutic device may be a medical device that is to be inserted into the body, such as an endoscope, a catheter or the like.

The protease according to the present invention may be used as a detergent composition. The detergent composition may be used in various applications, including laundry, dish washing, contact lens washing, false-tooth washing, and the like. The detergent composition may comprise, in addition to the protease of the present invention, other enzyme components and additives. The detergent composition of the present invention may comprise at least one surfactant, and the surfactant an anionic surfactant, a non-ionic surfactant, a catonic surfactant, an amphoteric or zwitterionic surfactant, or a mixture of two or more thereof. In addition, the detergent composition of the present invention may further comprise other detergent components known in the art, for example, an abrasive agent, a bleaching agent, a surface active agent, an anti-corrosive agent, a metal ion sequestering agent, an anti-stain reposition agent, a stabilizer for a perfume, an enzyme and a bleaching agent, a formulation aid, an optical brightening agent, a foam booster, a chelating agent, a filling agent, a fabric softener, or the like. In addition, the detergent composition of the present invention may be formulated in any convenient form such as powder, liquid or the like.

The protease according to the present invention may be a feed additive, a food additive or a pharmaceutical composition. The protease can be used in applications, including a food softener, a meat enhancer, an oil and fat separating agent, and the like. In addition, it can be used as a digestive enzyme agent for alleviating gastrointestinal disorders, digestive abnormalities, and abnormal diseases after gastrointestinal surgery, a thrombolytic agent that acts directly on thrombi to dissolve fibrin, an anti-inflammatory enzyme that acts as an in vivo defense system against foreign toxic substances to remove inflammatory substances or necrotic tissue, or an anti-inflammatory agent for post-surgery or post-trauma edema. The pharmaceutical composition according to the present invention comprises a pharmaceutically acceptable carrier in a mixture of the protease of the present invention. Pharmaceutical formulations are well known in the art, and the pharmaceutical composition comprising the protease can be easily formulated by those skilled in the art. The pharmaceutical composition may be administered parenterally (e.g., intravenously, subcutaneously or intramuscularly). Preferably, it is administered intravenously. The pharmaceutical composition is preferably used in the form of a sterile aqueous solution containing a sufficient amount of a salt, glucose or dextrose, which makes the solution isotonic. For oral administration, the pharmaceutical composition may be used in the form of tablets, capsules, lozenges, troches, powder, syrup, elixirs, solutions or suspensions, and may comprise various disintegrants such as starch, and lubricants.

The protease according to the present invention may be used as a fiber or leather processing agent, and may be used for removal of rubbery material from silk fiber, soaking of leather, etc.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Examination of Protease (W-Pro21717) Derived from *Pseudoalteromonas arctica* PAMC 21717

1-1: Culture and Examination of Production of W-Pro21717

*Pseudoalteromonas arctica* PAMC 21717 was cultured in 2% glucose-containing ZoBell medium (per liter, 5 g peptone, 1 g yeast extract, 0.01 g $FePO_4$, 750 ml seawater, and 250 ml distilled water) under three temperature conditions (5° C., 15° C. and 25° C.), and was then cultured at 25° C. for 1 day.

In order to measure the degradation activity of W-Pro21717, the cultured PAMC 21717 cells were centrifuged at 4° C. at 12,000×g for 30 minutes, and the supernatant was mixed with 50 mM sodium phosphate buffer (pH 7.6) containing 0.65% azocasein substrate, and was allowed to at 25° C. for 1 hour, and then additionally allowed to react at 37° C. for 1 hour after adding 110 mM trichloroacetic acid thereto. The reaction solution was centrifuged, and then filtered through a filter having a pore size of 0.45 μm, and the filtrate was mixed and reacted with Folin & Ciocalteu's phenol solution and 500 mM sodium carbonate solution at 37° C. for 30 minutes. Next, the enzymatic activity of the reaction product was measured at 660 nm based on an L-tyrosine standard curve, and an amino acid production of 1 nmole/min/mg at 25° C. was defined as the activity of 1 unit of protease.

As a result, it was shown that the maximum activity of W-Pro21717 was 2.7 U/ml at 15° C., 2.1 U/ml at 5° C., and 1.4 U/ml at 25° C., suggesting that the optimum temperature for the production of the protease was 15° C.

1-2: Zymogram Analysis and Kind of W-Pro21717

*Pseudoalteromonas arctica* PAMC 21717 was cultured at 15° C. for 96 hours, and then the enzyme protein isolated from the cells was electrophoresed on 10% SDS-PAGE gel comprising 0.3% skim milk and 1% gelatin. The PAGE gel was reacted with a denaturing buffer (27 g/L Triton X-100), and then reacted with a developing buffer (per liter of distilled water, 1.21 g Tris base, 6.3 g Tris-HCl, 11.7 g NaCl, 0.74 g $CaCl_2$, 0.02% Brij35) for 30 minutes, after the gel was stained with Coomassie blue, and the degradation activity of the protein was examined by zymogram analysis.

As a result, it was shown that two proteins (37 kDa and 74 kDa) found in the zymogram contained an amino acid sequence of GAQNSSWH (SEQ ID NO: 9) in their N-terminal end, and this amino acid sequence was consistent with the sequences of many serine proteases derived from *Pseudoalteromonas* spp. The 37 kDa and 74 kDa proteins derived from *Pseudoalteromonas arctica* PAMC 21717 were named "W-Pro21717" (FIG. 1), and the 74 kDa protein having a higher activity may be a homodimer of the 37 kDa protein.

The kind of W-Pro21717 was analyzed by reactions with various protease inhibitors.

As a result, as can be seen in Table 2 below, the activity of W-Pro21717 was inhibited by PMSF and $HgCl_2$, but was not influenced by other cysteine protease inhibitors. Also, the activity of W-Pro21717 was slightly inhibited by the metalloprotease inhibitor EDTA. Thus, it was found that a disulfide bond is important in enzymatic activity and that W-Pro21717 is a serine-based protease.

TABLE 2

| Inhibitor | Concentration (mM) | Residual activity (%) |
| --- | --- | --- |
| None | — | 100 |
| EDTA | 1 | 75 ± 9 |
| PMSF | 1 | 40 ± 8 |
| $HgCl_2$ | 1 | 23 ± 8 |
| Iodoacetamide | 1 | 94 ± 3 |
| APMA | 1 | 131 ± 2 |
| N-Ethylmaleimide | 1 | 107 ± 8 |

TABLE 2-continued

| Inhibitor | Concentration (mM) | Residual activity (%) |
|---|---|---|
| Leupeptin | 1 | 98 ± 2 |
| $N^\alpha$-p-tosyp-L-lysine chloromethyl ketone | 1 | 137 ± 13 |

Example 2

Characterization of Protease (W-Pro21717) Derived from *Pseudoalteromonas arctica* PAMC 21717

2-1: Activity and Stability of W-Pro21717 with Temperature and pH

A temperature optimal for the activity of W-Pro21717 was analyzed in the temperature range of 0 to 60° C., and the optimum pH was analyzed by 1-hour reactions in 50 mM sodium acetate (pH 2.0-6.0), 50 mM potassium phosphate (pH 7.0-10.0) and 50 mM sodium tetraborate (pH 10.0). As a control, 3 μg of the commercial protease Carlsberg subtilisin was used.

Figure 2:
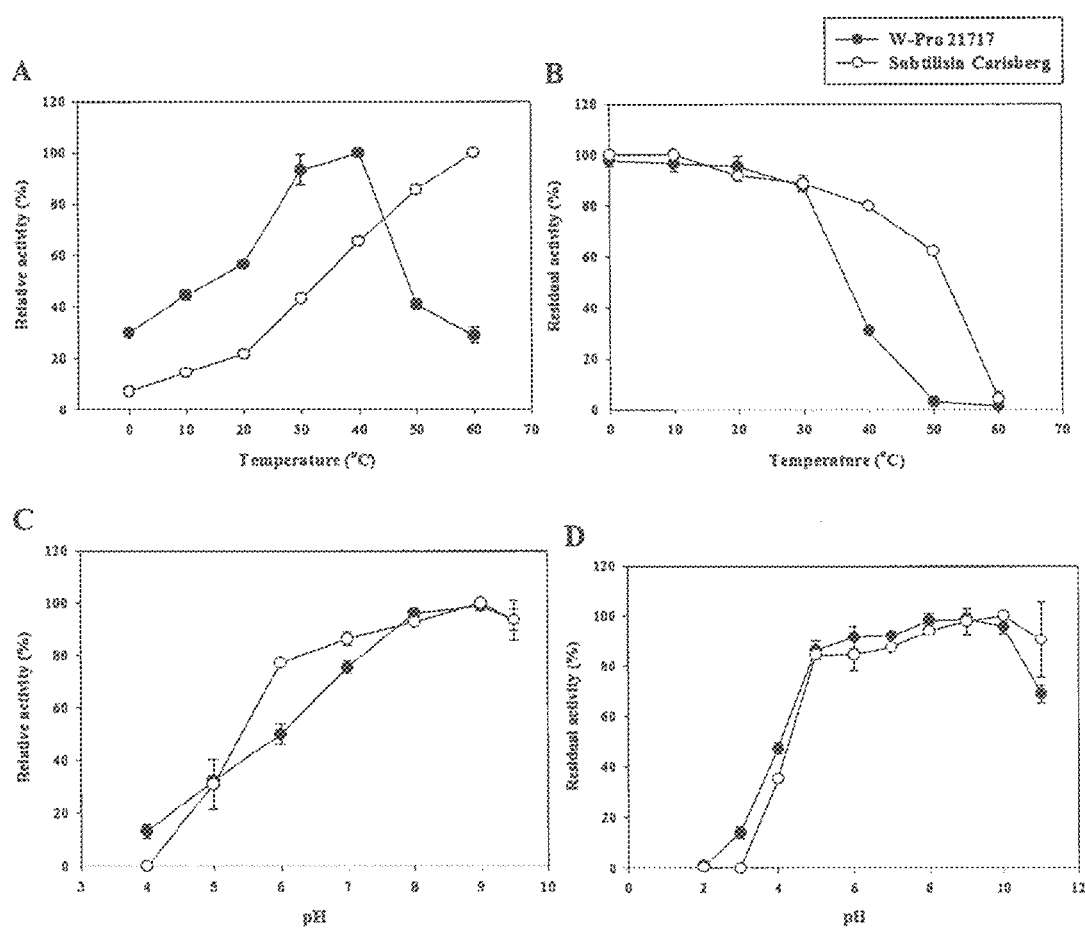
FIG. 2 shows the results of analyzing the activity and stability of W-Pro21717 as a function of temperature and pH. (A): a temperature optimal for the activity of W-Pro21717; (B) a temperature optimal for the stability of W-Pro21717; (C) a pH optimal for the activity of W-Pro21717; (D): a pH optimal for the stability of W-Pro21717.

As a result, it was shown that W-Pro21717 showed the highest activity at a temperature of 30~40° C. and that a temperature optimal for the activity of W-Pro21717 was 40° C. (FIG. 2A). Also, the control subtilisin Carlsberg showed the optimum activity at 60° C. In addition, at about or, W-Pro21717 showed an activity of 30%.

After a reaction at 40° C. for 1 hour, W-Pro21717 showed a decrease in activity of 30% (FIG. 2B), but subtilisin Carlsberg showed a decrease in activity of 80%. Thus, it was found that W-Pro21717 is a cold-adapted protease having a high low-temperature activity and stability.

W-Pro21717 showed high activity at a pH of 8.0-9.5, and showed the highest activity at a pH of 9.0 (FIG. 2C). In addition, it showed stability in a relatively wide pH range (pH 5.0-10.0), but lost its activity at a pH lower than 5.0 and a pH higher than 10.0 (FIG. 2D).

2-2: Activity and Stability of W-Pro21717 in the Presence of Metal Ions and Surfactants In order to analyze the influence of metal ions and detergents, W-Pro21717 was allowed to react with a standard buffer containing 1 mM $BaCl_2$, $CuSO_4$, $MgSO_4$, $CaCl_2$, $ZnSO_4$, $FePO_4$, KCl, NaCl, $N_2SO_4$, sodium linear alkylbenzene sulfonate (LAS) or SDS on ice for 1 hour. In addition, the compatibility of W-Pro21717 with a commercial detergent (LG Household & Health Care, Korea; containing subtilisin Carlsberg) was analyzed using skim milk at temperatures of 10° C. or and 30° C.

Figure 3:
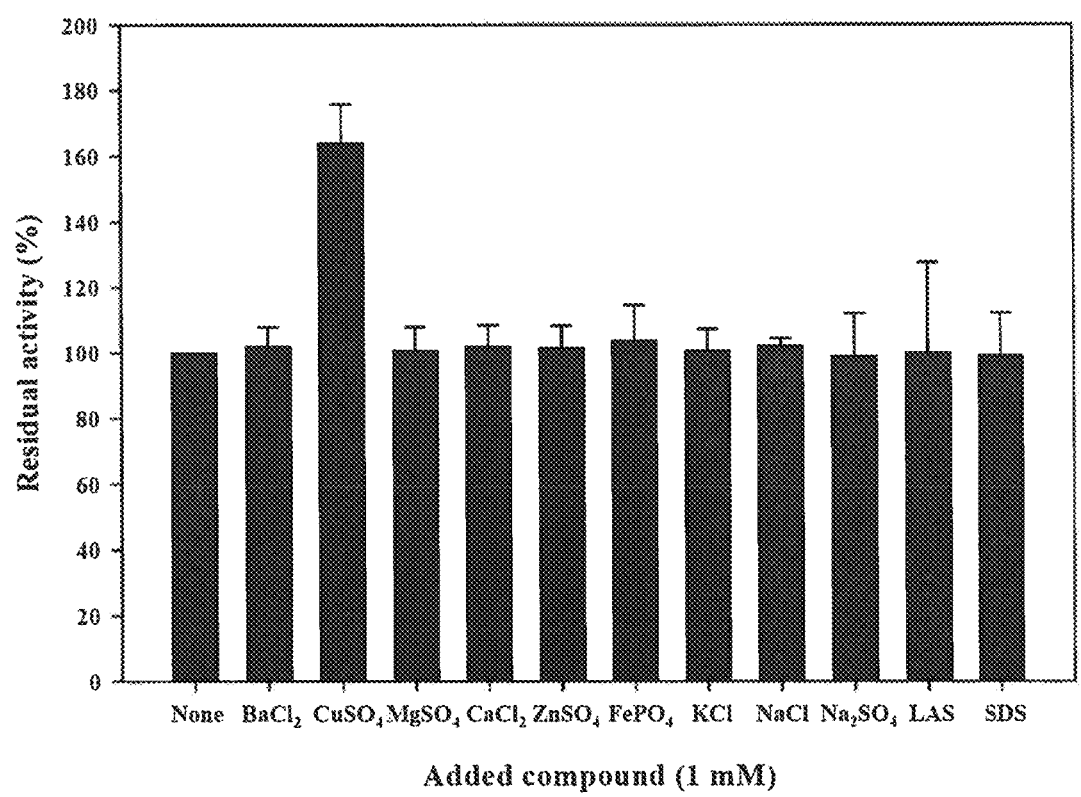
FIG. 3 shows the results of analyzing the activity and stability of W-Pro21717 in the presence of metal ions and surfactants.

As a result, it was shown that $CuSO_4$ increased the activity of W-Pro21717 by about 60%, and $Ba^{2+}$, Me, $Ca^{2+}$, $Zn^{2+}$, $Fe^{2+}$, $K^+$ and $Na^{2+}$ did not influence the activity of W-Pro21717 (FIG. 3).

Figure 4:
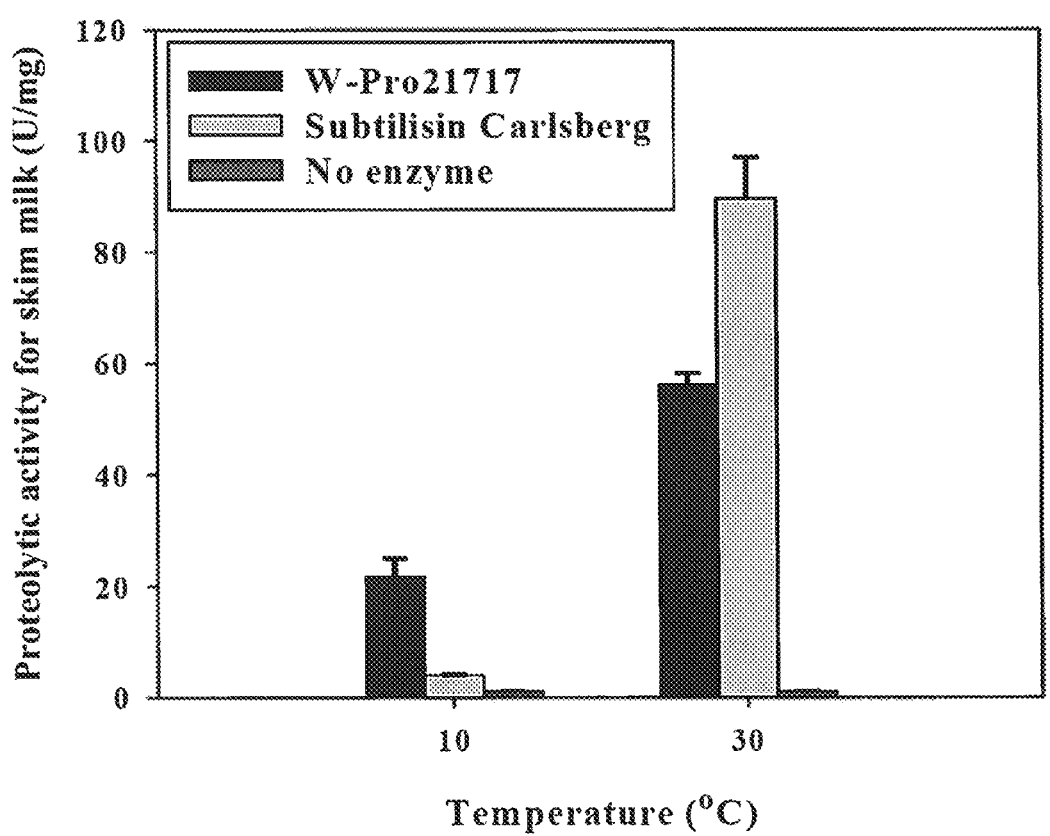
FIG. 4 shows the results of analyzing the compatibility of W-Pro21717 with a commercial protease using skim milk.

In addition, W-Pro21717 showed sufficient stability in the presence of the standard components ($Na_2SO_4$ and LAS) of general commercial detergents. Also, the results of measurement of the compatibility of W-Pro21717 with the general detergent indicated that W-Pro21717 showed the activities of 54.9±2.2 U/mg and 20.7±3.4 U/mg at 30° C. and 10° C., respectively (FIG. 4).

2-3: Substrate Specificity of W-Pro21717

The substrate specificity of W-Pro21717 was analyzed using 5 mM of each of the following 7 different synthetic peptides: N-succinyl-Ala-Ala-Val-p-nitroanilide (AAV), N-succinyl-Ala-Ala-Pro-Leu-p-nitroanilide (AAPL), N-succinyl-Ala-Ala-Ala-p-nitroanilide (AAA), N-succinyl-Gly-Gly-Phe-p-nitroanilide (GGF), N-succinyl-Thr-Leu-Val-p-nitroanilide (TLV), N-succinyl-Ala-Ala-Pro-Phe-p-nitroanilide (AAPF), and N-succinyl-Ala-Ala-Val-Ala-p-nitroanilide (AAVA). W-Pro21717 was allowed to react with a standard buffer containing 0.83 mM substrate at 25° C. for 10 minutes, and then the relative activity thereof was measured at 410 nm.

As a result, as can be seen in Table 3 below, W-Pro21717 showed high activity for AAPF (100%) and AAPL (66.5%), and subtilisin Carlsberg also had substrate specificities of 100% and 68.3%, which were similar to those of W-Pro21717.

TABLE 3

Comparison of specificity for various substrates between W-Pro21717 and subtilisin Carlsberg

| Substrate | Relative activity (%) | |
|---|---|---|
| Substrate | W-Pro21717 | Subtilisin Carlsberg |
| AAV | 3.1 ± 2.3 | 2.6 ± 1.3 |
| AAPL | 44.3 ± 1.1 | 66.5 ± 0.1 |
| AAA | 2.1 ± 1.1 | 1.5 ± 0.5 |
| GGF | 4.7 ± 1.7 | 0 |
| TLV | 6.7 ± 2.4 | 4.0 ± 3.7 |
| AAPF | 100 | 100 |
| AAVA | 8.7 ± 1.5 | 11.7 ± 2.3 |

Example 3

Culture Optimization for Production of Cold-Adapted Protease (W-Pro21717) Derived from *Pseudoalteromonas arctica* PAMC 21717

In this Example, for statistical optimization of the production of W-Pro21717, the optimum conditions for the production of W-Pro21717 derived from *Pseudoalteromonas arctica* PAMC 21717 were established through fed-batch culture at 15° C. For optimization of carbon, nitrogen and mineral media, a Plackett-Burman design was used.

Figure 5:
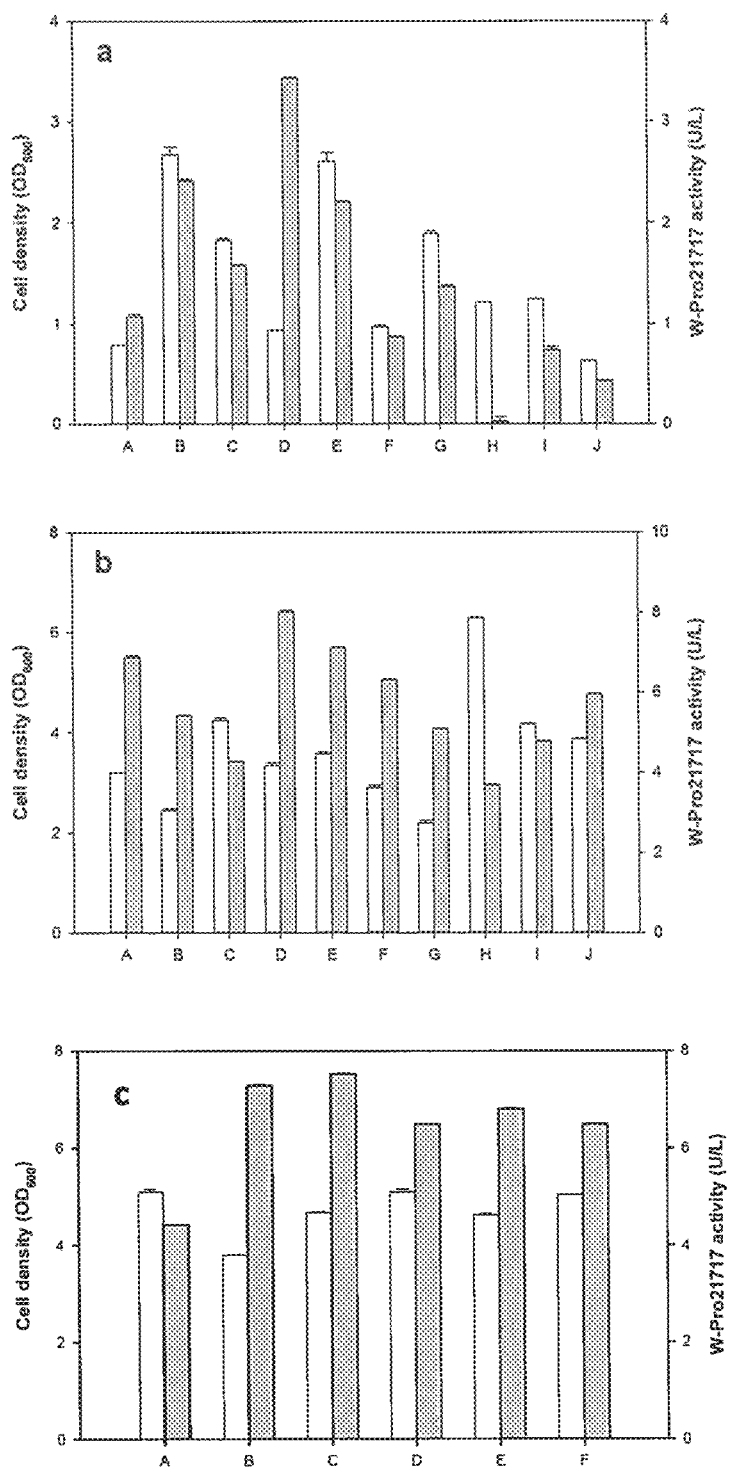
FIG. 5 shows the results of measuring the concentration of cells and the activity of W-Pro21717 after 3 hours of culture in order to examine the effects of carbon and nitrogen on medium optimization. (A): the effect of a carbon source on a skim milk-containing medium; (B) the effect of a carbon source on a medium containing no skim milk (A: control, B: glucose, C: galactose, D: fructose, E: lactose, F: sucrose, G: maltose, H: glycerol, I: starch, J: cellulose); and (C): the effect of nitrogen on a skim milk-containing medium (A: control, B: peptone, C: tryptone, D: yeast extract, E: soy peptone, F: tryptic soy broth)
Figure 6:
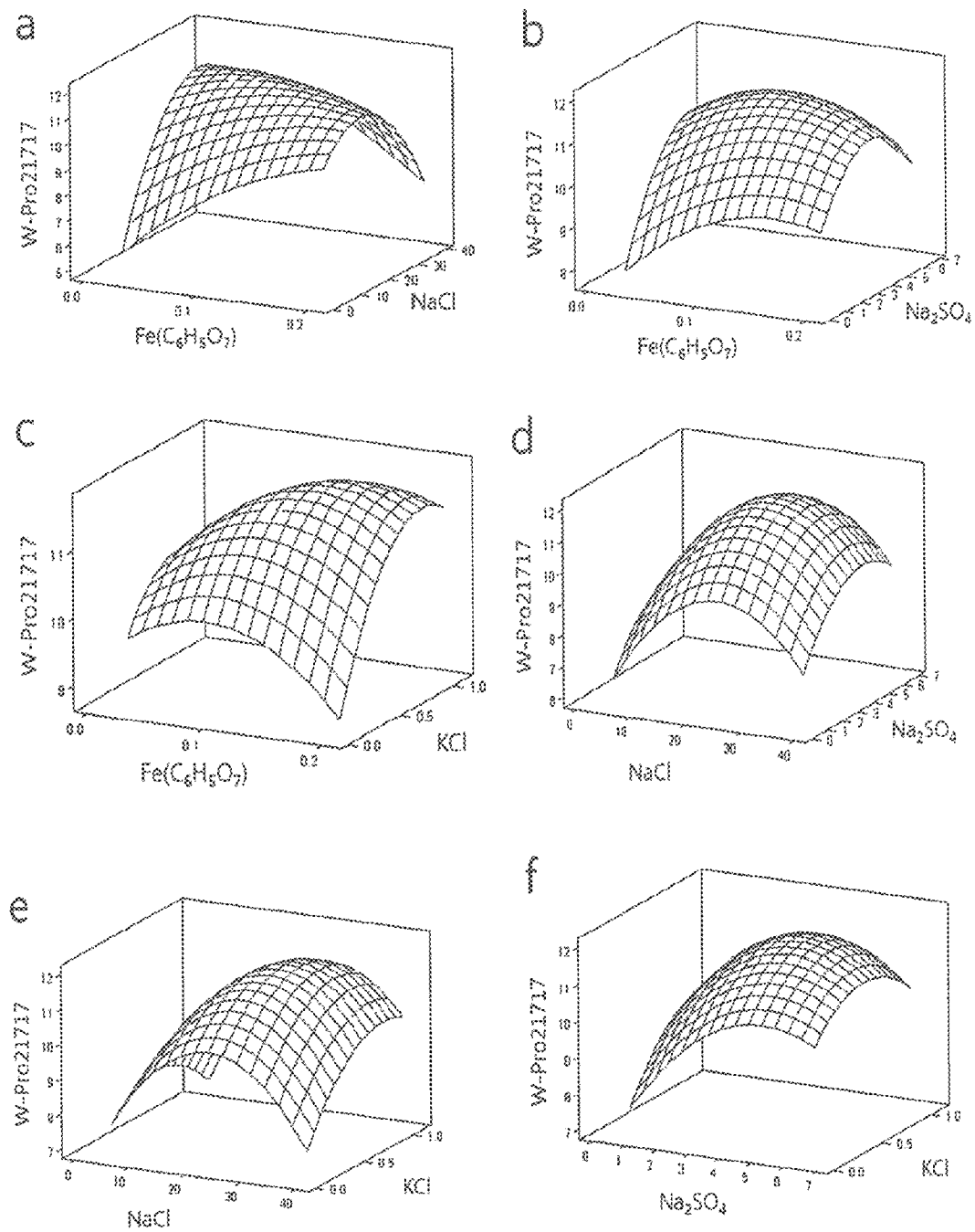
FIG. 6 depicts three-dimensional reaction plots showing the effects of minerals on the optimization of production medium. (A): $Fe(C_6H_5O_7)$ and NaCl; (B): $Fe(C_6H_5O_7)$ and $Na_2SO_4$; (C): $Fe(C_6H_5O_7)$ and KCl; (D): NaCl and $Na_2SO_4$; (E) NaCl and KCl; and (F) $Na_2SO_4$ and KCl.

As a result, fructose was selected as a carbon source, and it was shown that the activity of the enzyme was 8.0 U/L in a skim milk-containing medium and was 3.4 U/L in a medium containing no skim milk, suggesting that skim milk increased the activity of the enzyme by 2.3 times (FIGS. 5A and 5B). Nitrogen sources showed no difference in the activity of the enzyme, but tryptone was selected as a nitrogen source (FIG. 5C), and it was shown that the activity of the enzyme was increased by 3.4 times when $Fe(C_6H_5O_7)$, NaCl, $Na_2SO_4$ and KCl as mineral sources were contained in amounts of 0.1, 24.8, 4.4 and 0.7 g/L, respectively (FIG. 6).

Figure 7:
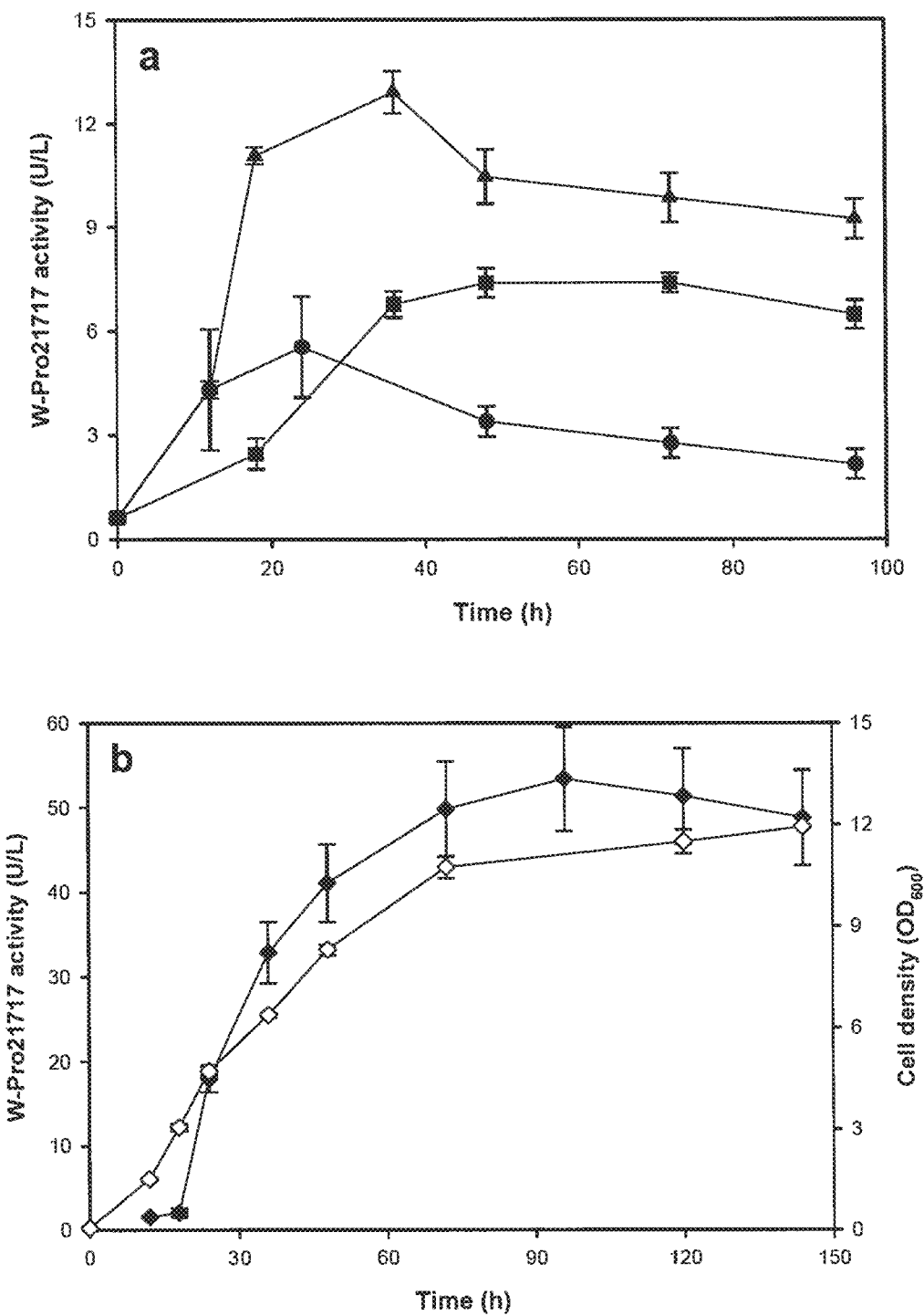
FIG. 7 shows the time-dependent activity of W-Pro21717 in a fed-batch culture process. (A) ●: basal medium containing no skim milk, ■: skim milk-containing basal medium, ▲: optimized mineral medium; (B) ◇: cell concentration, ♦: W-Pro21717 activity.

Fed-batch culture was performed in a medium composition containing 10 g/L skim milk, 0.6 g/L tryptone, 0.1 g/L $Fe(C_6H_5O_7)$, 24.8 g/L NaCl, 5.9 g/L $MgCl_2$, 4.4 g/L $Na_2SO_4$, 1.8 g/L $CaCl_2$, 0.16 g/L $NaHCO_3$ and 0.08 g/L KBr at 15° C. The activity of W-Pro21717 induced in the culture medium was 53.4 U/L, which was at least 15 times higher than that in the non-optimized culture medium (FIGS. 7A and 7B).

Example 4

Construction of Recombinant Protease (R-Pro21717) Based on Genetic Information of W-Pro21717

4-1: Vector Containing W-Pro21717-Encoding Gene

In this Example, the genomic library of *Pseudoalteromonas arctica* PAMC 21717 was constructed using the Copy- Control Fosmid Library Production Kit (Epicentre). Among 13 clones having proteolytic activity, EPI-P38 was selected and cleaved with 8 different restriction enzymes, after which it was introduced into a pUC19 vector, thereby obtaining the clone Rosetta-P38-4 having proteolytic activity.

The W-Pro21717 gene encoding the cold-adapted protease was amplified with the following primers, and then inserted into the expression vector pEXP5-CT/TOPO, thereby constructing and selecting plasmids having excellent proteolytic activity.

The W-Pro21717 gene was amplified by PCR using the chromosomal DNA of the *Pseudoalteromonas arctica* PAMC 21717 strain as a template and a primer set of SEQ ID NOs: 1 and 2 for pDOC122, a primer set of SEQ ID NOs: 3 and 6 for pDOC125, a primer set of SEQ ID NOs: 5 and 6 for pDOC128, or a primer set of SEQ ID NOs: 7 and 8 for pDOC131.

```
pDOC122
SEQ ID NOs: 1:
5'-ATGACAACAAGTAAAACTTTTAAAAGATGCGC-3'

SEQ ID NOs: 2:
5'-CACTTAGCGGACAATACCAACCG-3' pDOC122
SEQ ID NOs: 3:
5'-ATGCAATCAGTTTCAAGTTCAATGGC-3'

SEQ ID NOs: 4:
5'-CACTTAGCGGACAATACCAACCG-3' pDOC128
SEQ ID NOs: 5:
5'-ATGACAACAAGTAAAACTTTTAAAAGATGCGC-3'

SEQ ID NOs: 6:
5'-GCAGCTGTTGCAGCAGCAAGT-3' pDOC131
SEQ ID NOs: 7:
5'-ATGCAATCAGTTTCAAGTTCAATGGC-3'

SEQ ID NOs: 8:
5'-GCAGCTGTTGCAGCAGCAAGT-3'
```

4-2: Expression and Purification of R-Pro21717

In this Example, the function of the recombinant protein R-Pro21717 of the protease (W-Pro21717) derived from *Pseudoalteromonas arctica* PAMC 21717 was analyzed.

The four plasmids constructed in Example 4-1 were overexpressed, and the inclusion body (IB) of R-Pro21717 was analyzed by zymogram on 10% SDS-PAGE gel.

As a result, the protein expression of 72.6 kDa pDOC122 and 49.7 kDa pDOC128 was not observed. However, the expression of 69.9 kDa pDOC125 and 47 kDa pDOC131 was observed (FIG. 8A). pDOC131 that showed a significantly high proteolytic activity in zymogram analysis was finally selected.

pDOC131-containing *E. coli* BL21 star(DE3)pLysS was cultured in ampicillin-containing LB medium. When an $OD_{600}$ of 1.0 was reached, IPTG was added to the cells, which were then cultured for 24 hours, thereby inducing the expression of the R-Pro21717 recombinant protein. The cells were centrifuged, and the unfolded IB (inclusion body) was washed with an unfolding buffer. The unfolded protein solution was diluted with a refolding buffer, and it was dialyzed and purified by FPLC. The purified protein was the Pro21717 recombinant protein having proteolytic activity.

Figure 8:
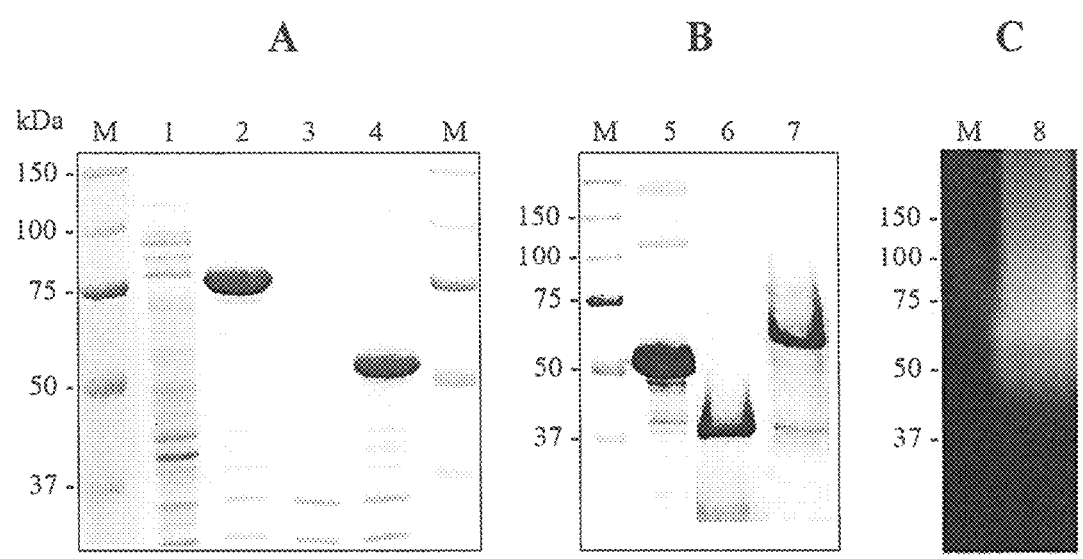
FIG. 8 shows the results of SDS-PAGE and zymogram analysis of recombinant protease R-Pro21717. (A): a recombinant protein expressed from a pDOC vector; (B) a recombinant protein during a refolding process; (C) recombinant protease R-Pro21717 purified after refolding. (1 to 5: inclusion bodies after washing of pDOC122, pDOC125, pDOC128, pDOC131 and pDOC131, respectively, 6: pDOC131 after 48 hours of refolding, 7: pDOC131 after 72 hours of refolding, 8: the expression product R-Pro21717 of pDOC131 purified by chromatography after refolding).

The expression of the insoluble portion other than water-soluble portion of the recombinant protein could be observed, the shift of the size occurred during the refolding process. The protein changed from 50 kDa to 37 kDa after 48 hours of refolding and changed to 63 kDa after 72 hours of refolding (FIG. 8B). It can be seen that the enzymatic activity of W-Pro21717 was 42.1±3.5 U/mg, but the enzymatic activity of the R-Pro21717 recombinant protein was 116.4±2.7 U/mg, which was 2.8 times higher than that of W-Pro21717. The refolded protease was purified by size exclusion chromatography, thereby constructing an R-Pro21717 recombinant protein showing an enzymatic activity of 268.6±7.5 U/mg, which was 6.4 times higher than that of W-Pro21717 (FIG. 8C).

Example 5

Activity and Stability of Recombinant Protease (R-Pro21717)

5-1: Influence of Temperature and pH

In this Example, the activity and stability of R-Pro21717 at low temperatures and high pHs were analyzed.

In order to determine a temperature optimal for the activity of the protease, R-Pro21717 was allowed to react at varying temperatures of 0~70° C., and then analyzed. The stability of R-Pro21717 against temperature was analyzed by allowing R-Pro21717 at varying temperatures of 0~70° C. for 1 hour, and then allowing R-Pro21717 to react a 0.65% azocasein-containing standard buffer at 30° C. for 30 minutes. As a control enzyme, Carlsberg subtilisin was used.

In order to determine a pH optimal for the activity of the protease, R-Pro21717-containing buffers having varying pHs were allowed to react at 30° C., and then analyzed. The stability of R-Pro21717 against pH was analyzed by allowing R-Pro21717-containing buffers having varying pHs to react on ice for 1 hour, and then reacting R-Pro21717 in 0.65% azocasein-containing standard buffer at 30° C. for 30 minutes. Carlsberg subtilisin was used as a control enzyme and analyzed at a reaction temperature of 40° C.

Figure 9:
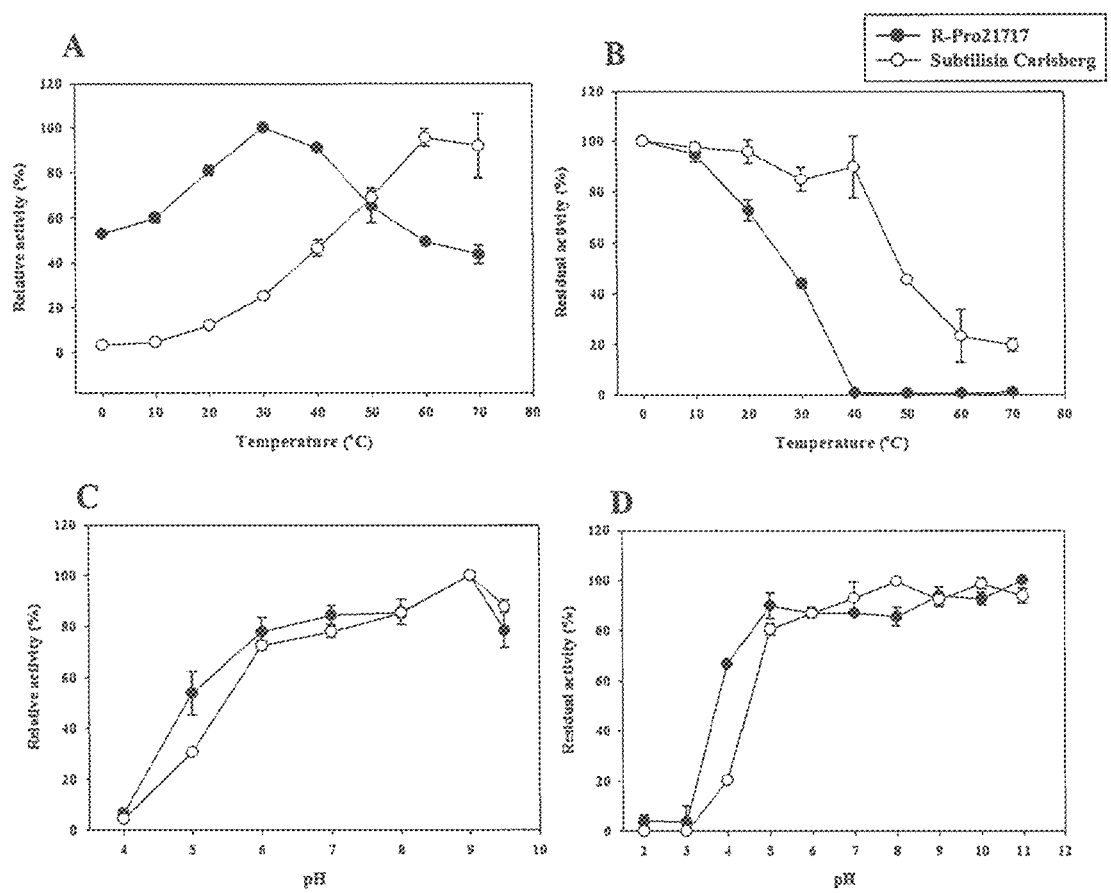
FIG. 9 shows the results of analyzing the activity and stability of recombinant R-Pro21717 as a function of temperature and pH. (A): a temperature optimal for the activity of R-Pro21717; (B): a temperature optimal for the stability of R-Pro21717; (C): a pH optimal for the activity of R-Pro21717; and (D): a pH optimal for the stability of R-Pro21717.

As a result, it was shown that the R-Pro21717 protease showed the highest activity at a temperature ranging from 30 to 40° C., and a temperature optimal for the activity of the R-Pro21717 protease was 30° C., and at or, the R-Pro21717 protease showed a proteolytic activity of 50% of the highest activity at 30° C. (FIG. 9A). However, the control enzyme Carlsberg subtilisin showed the highest activity at 60° C., and did not show proteolytic activity at or compared to 60° C. at which it showed the highest activity. In addition, it was shown that the stability of the R-Pro21717 protease against temperature decreased at 20° C. or higher (FIG. 9B), and the control enzyme Carlsberg subtilisin showed a decrease in enzymatic activity at 50° C. or higher.

In addition, it was shown that the R-Pro21717 protease showed the highest activity at a pH of 9.0 (FIG. 9C) and that a pH optimal for the stability of the enzyme was 5.0-11.0 (FIG. 9D), and the control enzyme Carlsberg subtilisin, a basic enzyme, also showed the same results as those of R-Pro21717.

5-2: Influence of Metal Ions and Surfactants

In this Example, the activity and stability of the R-Pro21717 protease in the presence of metal ions and surfactants were analyzed.

Figure 10:
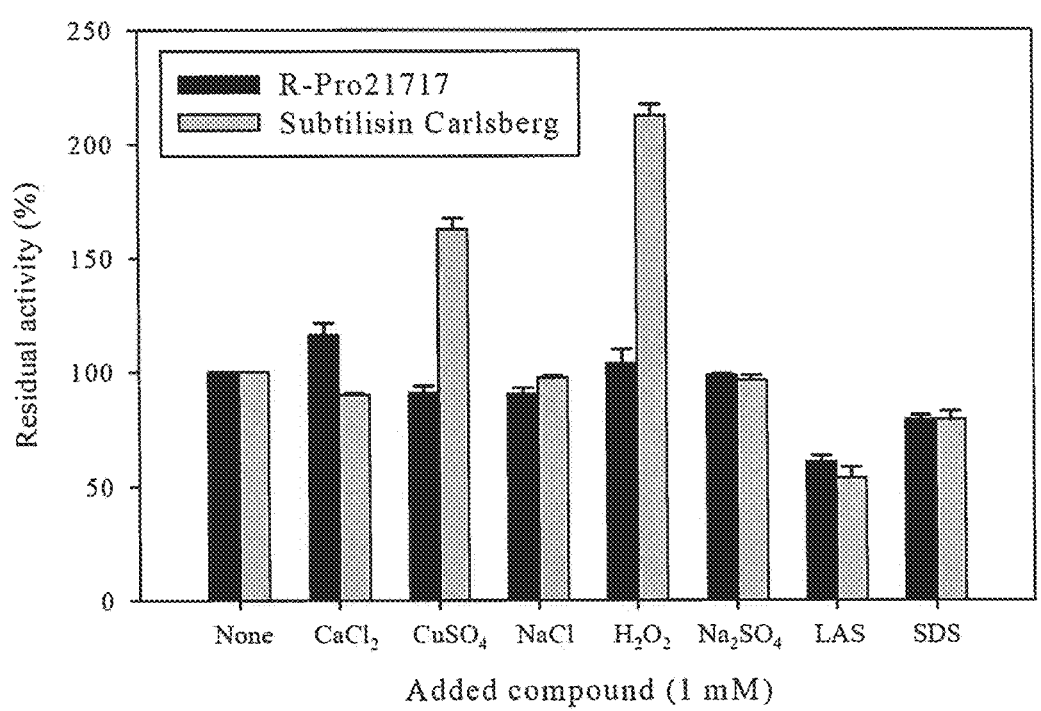
FIG. 10 shows the results of analyzing the activity and stability of recombinant R-Pro21717 in the presence of metal ions and surfactants. The activity was measured after adding R-Pro21717 to a standard buffer containing 1 mM of each material, and then allowing the R-Pro21717 on ice for 1 hour.

The analysis was performed by adding R-Pro21717 to a standard buffer containing $CaCl_2$, $CuSO_4$, NaCl, $N_2SO_4$, LAS, SDS, PMSF or 1% $H_2O_2$, allowing the mixture to react on ice for 1 hour, and then adding 0.65% azocasein thereto (FIG. 10).

As a result, it was shown that the activity and stability of the R-Pro21717 protease in the presence of metal ions and surfactants were better than those of general detergent enzymes, like the control enzyme Carlsberg subtilisin.

5-3: Substrate Specificity

In this Example, the activity of the R-Pro21717 protease in the presence of synthetic peptide substrates was analyzed. As a result, it was shown that the R-Pro21717 protease showed activity similar to that of the control enzyme Carlsberg subtilisin, and showed relatively low activities in the presence of complex substrates including collagen and keratin (Table 4).

Accordingly, it was found that the cold-adapted protease derived from *Pseudoalteromonas arctica* PAMC 21717 according to the present invention shows high activity at low temperatures, and securely maintains its enzymatic activity even in the presence of various metal ions and surfactants that are contained in detergent compositions. This suggests that the cold-adapted protease derived from *Pseudoalteromonas arctica* PAMC 21717 can be used in various industrial applications.

TABLE 4

| Substrate | | Relative activity (%) | |
|---|---|---|---|
| Substrate | | R-Pro21717 | Subtilisin Carlsberg |
| Macro molecule | Collagen | 8.3 ± 2.8 | 6.7 ± 1.2 |
| Macro molecule | Keratin | 14.1 ± 0.3 | 30.2 ± 5.6 |
|  | Azocasein | 100 | 100 |
|  | Skim milk | 41.7 ± 2.5 | 67.7 ± 5.7 |
| Oligo molecule | AAV | 2.4 ± 1.4 | 7.9 ± 3.9 |
| Oligo molecule | AAPL | 41.7 ± 0.2 | 57.1 ± 10.1 |
|  | AAA | 2.1 ± 0.8 | 10.2 ± 1.9 |
|  | GGF | 11.2 ± 7.4 | 16.2 ± 2.1 |
|  | TLV | 3.8 ± 0.1 | 11.9 ± 1.1 |
|  | AAPF | 100 | 100 |
|  | AAVA | 6.4 ± 2.1 | 12.9 ± 0.6 |

Example 6

Culture Optimization for Production of Recombinant Protease (R-Pro21717)

In this Example, for optimization of the production of the recombinant protease R-Pro21717, the optimum conditions for the production of R-Pro21717 in the recombinant microorganism prepared in Example 4 were established through batch-type culture and fed-batch culture.

Culture was performed in a medium containing glucose, $KH_2PO_4$, $(NH_4)_2PO_4$, citric acid, $MgSO_4 \cdot 7H_2O$, thiamine, an antibiotic and a trace metal element at 37° C., and then when the pH and DO of the medium rose due to complete consumption of glucose, pH-stat fed-batch was performed for at least 15 hours while a predetermined amount of a medium containing glucose, a yeast extract, $(NH_4)_2PO_4$, $MgSO_4 \cdot 7H_2O$ and an antibiotic was fed, thereby expressing a cold-adapted protease. In this way, the production of R-Pro21717 was optimized.

Example 7

Crystallization and Structural Analysis of Cold-Adapted Protease

A purified protease was concentrated to a concentration of 250 mg/ml, and then crystallized at 20° C. using the sitting drop vapor diffusion method. For crystallization, a protein solution 0.81 µl of a protein solution (containing 250 mg/ml protein, 20 mM Tris-HCl (pH 8.0) and 150 mM NaCl) and 0.81 µl of a preservative solution (0.1 M sodium acetate (pH 4.4) and 3 M sodium chloride) were used. The single crystal grew in the form of needles so that the longest axis had a length of about 0.5 mm or less after 2 days. For a cryogenic experiment, the protease crystal was immersed in paratone oil, and after 2 minutes, immersed in liquid nitrogen. X-ray diffraction data were analyzed at a resolution of 1.4 Å at the 7 A beamline of the Pohang Accelerator Laboratory (Pohang, Republic of Korea), and indexed using the HKL2000 program.

As a result, it was shown that the protease crystal had a space group of $P2_12_12_1$ with unit cell dimensions of a=47.9 Å, b=74.6 Å and c=83.0 Å. The protease crystal had the atomic coordinates shown in Table 5 below and Table 1 above.

In addition, the structure of the crystal was analyzed by a molecular replacement method using the MOLREP program and an AprV2 structure (PDB code 3LPA) as a template, and the refinement of the structure was performed using REFMAC5 and the Coot program.

Figure 11:
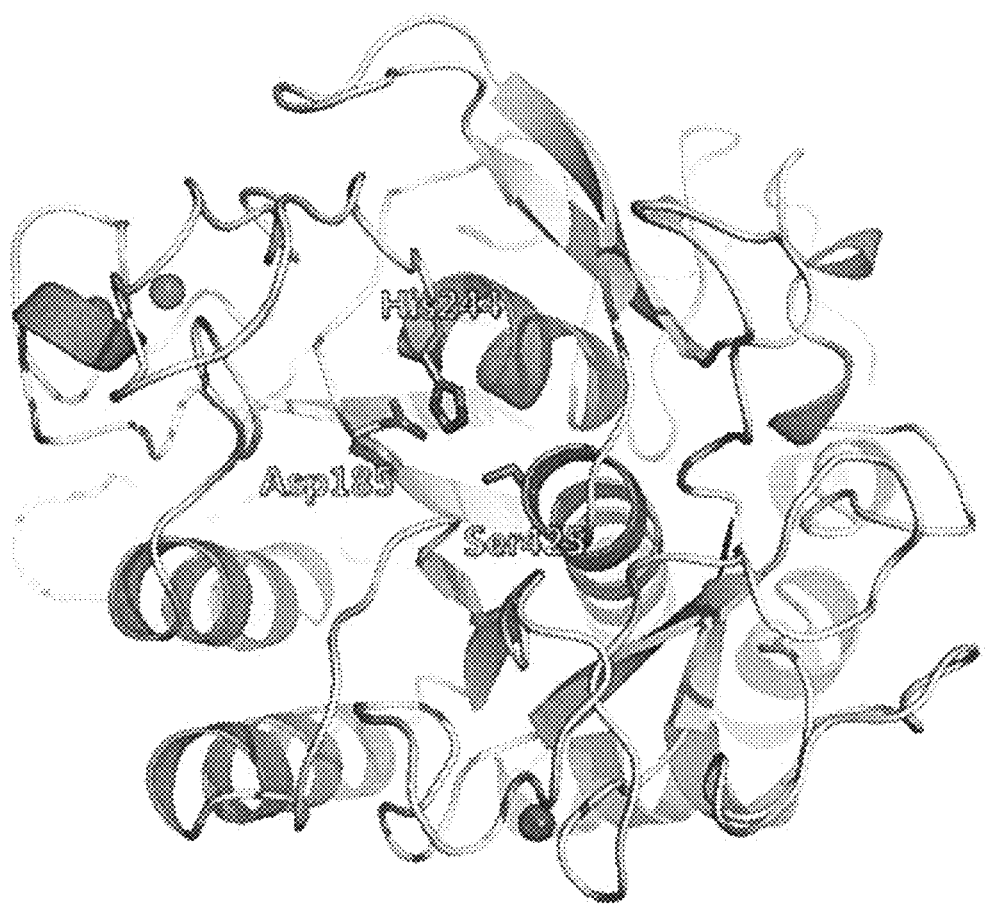
FIG. 11 shows the three-dimensional crystalline structure of a cold-adapted protease (R-Pro21717) that has four calcium ion bonds and an active site consisting of a catalytic triad composed of Asp185, His244 and Ser425.

The overall structure of the protease has a subtilisin-like fold and is composed of ten α-helices which surround the central 6 β-strands and two β-strands. The enzymatic active site is composed of a catalytic triad consisting of three residues (Asp159, His218 and Ser399). Thus, it could be found from the structural information of the protease that the protease is a serine-based protease. In addition, the protease has four calcium ion bonds that assist in the stabilization of the protease (FIG. 11).

TABLE 5

| Data set | |
|---|---|
| X-ray source | Beamline 7A, PAL |
| Space group | $P2_12_12_1$ |
| Wavelength (Å) | 0.97934 |
| Resolution range (Å) | 30.00-1.40 (1.42-1.40) |
| No. of observed reflections | 804441 |
| No. of unique reflections | 58245 (2849) |
| $R_{sym}$ $^a$(%) | 6.6 (15.0) |
| Average I/σ | 69.0 (36.3) |
| Completeness (%) | 98.0 (98.2) |
| Multiplicity | 13.8 (14.3) |
| Refinement | |
| Resolution (Å) | 55.47-1.40 (1.44-1.40) |
| No. of reflections in working set | 55253 (4010) |
| No. of reflections in test set | 2939 (207) |
| No. of residues | 339 |
| No. of water molecules | 579 |
| No. of calcium ions | 4 |
| $R_{cryst}$ $^b$total(%) | 13.72 (14.3) |
| $R_{free}$ $^c$total(%) | 16.09 (16.5) |
| R.m.s. bond length (Å) | 0.028 |
| R.m.s. bond angle (°) | 2.42 |
| Average B value (Å$^2$) | 10.769 |

$^a$ $R_{sym} = \Sigma |<I> - I|/\Sigma<I>$.
$^b$ $R_{cryst} = \Sigma|Fo| - |Fc||/\Sigma|Fo|$.
$^c$ $R_{free}$ calculated with 10% of all reflections excluded from refinement stages using high resolution data.
Values in parentheses refer to the highest resolution shells.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

DEPOSIT OF MICROORGANISMS

Depository Institution: Korean Collection for Type Cultures (KCTC), Korea Research Institute of Bioscience and Biotechnology (KRIBB), 125 Gwahak-ro, Yuseong-gu, Daejeon 305-806, Republic of Korea;

Taxonomic Identification: *Pseudoalteromonas arctica* PAMC 21717;

Accession Number: KCTC12482BP;

Deposit Date: Sep. 3, 2013.

What is claimed is:

1. A crystal of a cold-adapted protease prepared by expressing a gene in a recombinant *E. coli*, said gene obtained by PCR using a template of DNA derived from *Pseudoalteromonas arctica* PAMC 21717 and a set of primers of SEQ ID NOs: 7 and 8, wherein the crystal of the cold-adapted protease has the following crystal structure:
   (i) a subtilisin-like fold;
   ii) four calcium ions and two disulfide bonds (Cys439-Cys442 and Cys207-Cys254);
   (iii) a three-dimensional structure including ten α-helices which surround the central 6 β-strands and two β-strands; and
   (iv) a structure crystallized with $P2_12_12_1$ space group either unit cell parameters of a=47.9 Å, b=74.6 Å, c=83.0 Å, α=β=γ=90° or 2374 atomic coordinates (including 4 calcium ions) set forth in Table 1.

2. The crystal of the cold-adapted protease of claim 1, comprising an enzymatic active site consisting of a catalytic triad of amino acid residues Asp185, His244 and Ser425.

3. A disinfectant composition for a surgical or therapeutic device, the composition containing a crystal of the cold-adapted protease of claim 1.

4. A detergent composition containing a crystal of the cold-adapted protease of claim 1.

5. A feed additive composition containing a crystal of the cold-adapted protease of claim 1.

6. A food additive composition containing a crystal of the cold-adapted protease of claim 1.

7. A fiber or leather processing composition containing a crystal of the cold-adapted protease of claim 1.

8. The crystal of the cold-adapted protease of claim 1, having a space group of $P2_12_12_1$ with unit cell dimensions of a=47.9 Å, b=74.6 Å and c=83.0 Å.

9. The crystal of the cold-adapted protease of claim 1, having the 2374 atomic coordinates (including 4 calcium ions) set forth in Table 1.

10. A crystal of a *Pseudoalteromonas artica* cold-adapted protease comprising SEQ ID NO: 10, wherein said crystal is characterized by having $P2_12_12_1$ space group with unit cell parameters of a=47.9 Å, b=74.6 Å, c=83.0 Å, α=β=γ=90°, wherein said protease structure is characterized by: (i) subtilisin-like fold; (ii) four calcium ions and two disulfide bonds (Cys439-Cys442 and Cys207-Cys254); (iii) ten alpha-helices which surround the central six central β-strands and two additional β-strands; and (iv) the atomic coordinates as set forth in Table 1.

11. A method for crystallizing a cold-adapted protease derived from *Pseudoalteromonas arctica* PAMC 21717 or a recombinant cold-adapted protease obtained by expressing a gene encoding the cold-adapted protease in *E. coli*, wherein the gene is obtained by PCR using a template of DNA derived from *Pseudoalteromonas arctica* PAMC 21717 and a set of primers of SEQ ID NO: 7 and 8, and wherein the method comprises crystallizing at 20° C. using a protein solution containing 20 mM Tris-HCl (pH 8.0) and 150 mM NaCl, and a preservative solution containing 0.1 M sodium acetate (pH 4.4) and 3 M sodium chloride.

* * * * *

UNITED STATES PATENT AND TRADEMARK OFFICE
CERTIFICATE OF CORRECTION

PATENT NO. : 9,574,185 B2
APPLICATION NO. : 14/583557
DATED : February 21, 2017
INVENTOR(S) : Joung Han Yim et al.

Page 1 of 1

It is certified that error appears in the above-identified patent and that said Letters Patent is hereby corrected as shown below:

In the Specification

Column 73, Line 28: "In addition, at about or," should be --In addition, at about 0° C.,--.

Column 73, Line 50: "of 10° C. or and 30° C." should be --of 10° C. and 30° C.--.

Column 76, Line 45: "and at or, the R-Pro21717" should be --and at 0° C., the R-Pro21717--.

Column 76, Line 49: "activity at or compared to" should be --activity at 0° C. compared to--.

Signed and Sealed this
Eleventh Day of April, 2017

Michelle K. Lee
*Director of the United States Patent and Trademark Office*